United States Patent
Bradbury et al.

(10) Patent No.: US 8,044,204 B2
(45) Date of Patent: Oct. 25, 2011

(54) 8-METHOXY-9H-ISOTHIAZOLO[5,4-B] QUINOLINE-3,4-DIONES AND RELATED COMPOUNDS AS ANTI-INFECTIVE AGENTS

(75) Inventors: Barton James Bradbury, Wallingford, CT (US); Jason Allan Wiles, Hamden, CT (US); Qiuping Wang, Bethany, CT (US); Akhiro Hashimoto, Branford, CT (US); Edlaine Lucien, New Haven, CT (US); Godwin Clarence Gilroy Pais, Hampden, CT (US); Milind Deshpande, Madison, CT (US); Michael John Pucci, Kensington, CT (US); Ha Young Kim, Cheshire, CT (US)

(73) Assignee: Achillion Pharmaceuticals, Inc., New Haven, CT (US)

( * ) Notice: Subject to any disclaimer, the term of this patent is extended or adjusted under 35 U.S.C. 154(b) by 1291 days.

(21) Appl. No.: 11/494,205

(22) Filed: Jul. 27, 2006

(65) Prior Publication Data

US 2007/0049586 A1     Mar. 1, 2007

Related U.S. Application Data

(60) Provisional application No. 60/702,811, filed on Jul. 27, 2005.

(51) Int. Cl.
    *C07D 417/04* (2006.01)
    *C07D 409/04* (2006.01)
    *A61K 31/4365* (2006.01)
(52) U.S. Cl. .................................. 546/83; 514/290
(58) Field of Classification Search ............. 546/83; 514/290
    See application file for complete search history.

(56) References Cited

U.S. PATENT DOCUMENTS

| | | | |
|---|---|---|---|
| 4,767,762 A | 8/1988 | Chu | |
| 5,071,848 A | 12/1991 | Chu et al. | |
| 5,087,621 A | 2/1992 | Pinol et al. | |
| 5,387,748 A | 2/1995 | Demuth et al. | |
| 5,519,016 A | 5/1996 | Kimura et al. | |
| 5,580,872 A | 12/1996 | Chu et al. | |
| 5,631,256 A | 5/1997 | Demuth, Jr. et al. | |
| 5,646,163 A | 7/1997 | Demuth, Jr. et al. | |
| 5,688,791 A | 11/1997 | Kimura et al. | |
| 6,288,081 B1 | 9/2001 | Petersen et al. | |
| 2004/0029882 A1 | 2/2004 | Ledoussal et al. | |
| 2005/0075363 A1* | 4/2005 | Bradbury et al. ........... 514/292 |
| 2006/0100215 A1* | 5/2006 | Bradbury et al. ........ 514/253.03 |
| 2006/0235041 A1* | 10/2006 | Bradbury et al. ........... 514/292 |

FOREIGN PATENT DOCUMENTS

| | | |
|---|---|---|
| EP | 0394120 A1 | 4/1990 |
| EP | 0227088 B1 | 8/1991 |
| EP | 0878194 A1 | 11/1998 |
| JP | 01160985 A | 6/1989 |
| JP | 01193275 A | 8/1989 |
| JP | 01265092 A | 10/1989 |
| JP | 02174784 A | 7/1990 |
| JP | 02243692 A | 9/1990 |
| JP | 02255687 A | 10/1990 |
| JP | 03058992 A | 3/1991 |
| JP | 03209367 A | 9/1991 |
| JP | 09288105 A | 11/1997 |
| JP | 10130149 A | 5/1998 |
| WO | 95/29894 A1 | 11/1995 |
| WO | 02/48138 A1 | 6/2002 |
| WO | 2005/019228 A1 | 3/2005 |

OTHER PUBLICATIONS

Wierenga, W., et al., "General, Efficient, One-Step Synthesis of Beta-Keto Esters," J. Org. Chem., (1979) 44: 310-311.

(Continued)

*Primary Examiner* — Rita Desai
(74) *Attorney, Agent, or Firm* — Cantor Colburn LLP

(57) ABSTRACT

The invention provides compound and salts of Formula I and II, disclosed herein, which includes compounds of Formula A and Formula B:

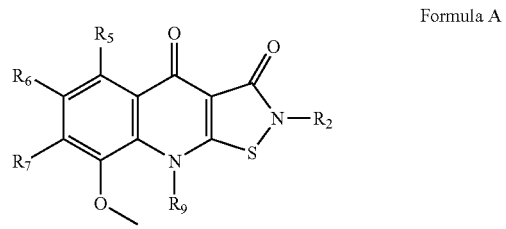

Formula A

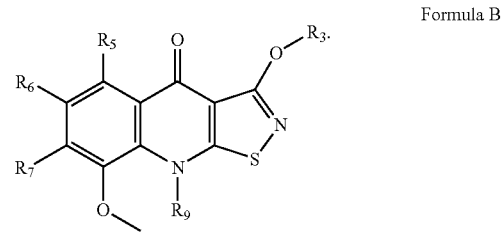

Formula B

Such compounds possess useful antimicrobial activity. The variables $R_2$, $R_3$, $R_5$, $R_6$, $R_7$, and $R_9$ shown in Formula A and B are defined herein.

Certain compounds of Formula I and Formula II disclosed herein are potent and/or selective inhibitors of bacterial DNA synthesis and bacterial replication. The invention also provides antimicrobial compositions, including pharmaceutical compositions, containing one or more compounds of Formula I or Formula II and one or more carriers, excipients, or diluents. Such compositions may contain a compound of Formula I or Formula II as the only active agent or may contain a combination of a compound of Formula I or Formula II and one or more other active agents. The invention also provides methods for treating microbial infections in animals.

22 Claims, No Drawings

OTHER PUBLICATIONS

Chu, D.T.W., et al., "Structure-Activity Relationships in Quinolone Antibacterials: Design, Sythesis and Biological Activities of Novel Isothiazoloquinolones," Drugs Exptl. Clin. Research, (1988) 14(6): 379-83.

Shen, L.L., et al., "Mechanism of Inhibition of DNA Gyrase by Quinolone Antibacterials: A Cooperative Drug-DNA Binding Model," Biochemistry, (1989) 28: 3886-3894.

Chu, D.T.W., et al. "Practical Synthesis of Iminochlorothioformates: Application of Iminochlorothioformates in the Synthesis of Novel 2,3,4,9-Tetrahydroisothiazolo[5,4-b][1,8]naphthyridine-3,4-diones and 2,3,4,9-Tetrahydroisothiazolo [5,4-b]quinoline-3,4-dione Derivatives," J. Heterocyclic Chem., (1990) 27: 1191-1195.

Chu, D.T.W., "Syntheses of 6-Fluoru-7-piperazin-1-yl-9-cyclopropyl-2,3,4,9-tetrahydroisothiazolo[5,4-b]quinoline-3,4-dione and 6-Fluoro-7-piperazin-1-yl-9p-fluorophenyl-2,3,4,9-tetrahydroisothiazolo[5,4-b]quinoline-3,4-dione [1]," J. Heterocyclic Chem., (1990) 27: 839-843.

Kohlbrenner, W.E, et al., "Induction of Calf Thymus Topoisomerase II-Mediated DNA Breakage by the Antibacterial Isothiazoloquinolones A-65281 and A-65282," Antimicrobial Agents and Chemotherapy, (1991) 36(1): 81-86.

Frigola, J., et al. "7-Azetidinylquinolones as Antibacterial Agents. Synthesis and Structure-Activity Relationships," J. Med. Chem, (1993) 36(7): 801-810.

Chung, S.K. et al., "Geometry Mapping of N(1)-Substituents of Quinolone Antibacterials and the Antibacterial Mode of Actions," Korean J. of Med. Chem., (1993) 3(2): 148-161.

Nahm, K. et al., "Quinolone Compounds with Carboxylic Equivalents and Semiempirical Calculations on their Tautomers," Biorganic & Medicinal Chemistry Letters, (1993) 3(12): 2631-2634.

Frigola, J., et al., "7-Azetidinylquinolones as Antibacterial Agents. 2. 1 synthesis and Biological Activity of 7-92,3-Disubstituted-1-azetidinyl)-4-oxoquinoline- and 1,8-naphthyridine-3-carboxylic Acids. Properties and Structure—Activity Relationships of Quinolones with an Azetidine Moiety," J. Med. Chem., (1994) 37(24): 4195-4210.

Lenoir, E.A., et al., "An Efficient Method for the Synthesis of (R)-3-(1-Amino-1-methylethyl)pyrrolidines for the Antiinfective Agent, PD 138312," Tetrahedron: Asymmetry, (1994), 5: 1131-1134.

Reuman, M., et al., "Synthesis and Antibacterial Activity of Some Novel 1-Substituted 1,4-Dihydro-4-oxo-7-pyridinyl-3-quinolinecarboxylic Acids. Potent Antistaphylococcal Agents," J. Med. Chem. (1995) 38: 2531-2540.

Tamao K., and Miyaura, N., "Introduction to Cross-Coupling Reactions," Topics in Current Chemistry (2002) 219: 1-9.

Inagaki, H., et al., "Synthesis and Structure-Activity Relationships of 5-Amino-6-fluoro-1-[(1R,2S)-2fluorocyclopropan-1-yl]-8-methylquinolonecarboxylic Acid Antibacterials Having Fluorinated 7-[(3R)-3-(1-Aminocyclopropan-1-y1) pyrrolidin-1-yl] Substituents", J. Med. Chem., (2003) 46: 1005-1015.

Potemkin, V.A. et al., "Theoretical Investigation of the Antituberculous Activity of Membranotropic Podands," Pharmaceutical Chemistry Journal (translation of Khimiko-Farmatsevticheskii Zhurnal), (2003) 37: 468-472.

* cited by examiner

8-METHOXY-9H-ISOTHIAZOLO[5,4-B] QUINOLINE-3,4-DIONES AND RELATED COMPOUNDS AS ANTI-INFECTIVE AGENTS

CROSS REFERENCE TO RELATED APPLICATION

This application claims priority from U.S. Provisional Application Ser. No. 60/702,811, filed Jul. 27, 2005, which is hereby incorporated by reference in its entirety.

FIELD OF THE INVENTION

The present invention provides 8-methoxy-9H-isothiazolo[5,4-b]quinoline-3,4-diones and related compounds, in which the 7-position substituent is generally an N-linked heterocycloalkyl or heterocycloalkenyl substituent, which possess antimicrobial activity. Certain compounds provided herein possess potent antibacterial, antiprotozoal, or antifungal activity. Particular compounds provided herein are also potent and/or selective inhibitors of prokaryotic DNA synthesis and prokaryotic reproduction. The invention provides anti-microbial compositions, including pharmaceutical compositions, containing one or more carrier, diluents, or excipients. The invention provides pharmaceutical compositions containing a 8-methoxy-9H-isothiazolo[5,4-b]quinoline-3,4-dione or related compound as the only active agent or containing a 8-methoxy-9H-isothiazolo[5,4-b]quinoline-3,4-dione or related compound in combination with one or more other active agent, such as one or more other antimicrobial or antifungal agent. The invention provides methods for treating or preventing microbial infections in animals by administering an effective amount of a 7-substituted-9H-isothiazolo[5,4-b]quinoline-3,4-dione or related compound to an animal suffering from or susceptible to microbial infection. The invention also provides methods of inhibiting microbial growth and survival by applying an effective amount of a 7-substituted-9H-isothiazolo[5,4-b]quinoline-3,4-diones or related compound.

BACKGROUND OF THE INVENTION

Antimicrobial compounds are compounds capable of destroying or suppressing the growth or reproduction of microorganisms, such as bacteria, protozoa, mycoplasma, yeast, and fungi. The mechanisms by which antimicrobial compounds act vary. However, they are generally believed to function in one or more of the following ways: by inhibiting cell wall synthesis or repair; by altering cell wall permeability; by inhibiting protein synthesis; or by inhibiting synthesis of nucleic acids. For example, beta-lactam antibacterials inhibit the essential penicillin binding proteins (PBPs) in bacteria, which are responsible for cell wall synthesis. Quinolones act, at least in part, by inhibiting synthesis of DNA, thus preventing the cell from replicating.

Many attempts to produce improved antimicrobials yield equivocal results. Indeed, few antimicrobials are produced that are truly clinically acceptable in terms of their spectrum of antimicrobial activity, avoidance of microbial resistance, and pharmacology. There is a continuing need for broad-spectrum antimicrobials, and a particular need for antimicrobials effective against resistant microbes.

Pathogenic bacteria are known to acquire resistance via several distinct mechanisms including inactivation of the antibiotic by bacterial enzymes (e.g., beta-lactamases that hydrolyze penicillin and cephalosporins); removal of the antibiotic using efflux pumps; modification of the target of the antibiotic via mutation and genetic recombination (e.g., penicillin-resistance in *Neiserria gonorrhea*); and acquisition of a readily transferable gene from an external source to create a resistant target (e.g., methicillin-resistance in *Staphylococcus aureus*). There are certain Gram-positive pathogens, such as vancomycin-resistant *Enterococcus faecium*, which are resistant to virtually all commercially available antibiotics.

Resistant organisms of particular note include methicillin-resistant and vancomycin-resistant *Staphylococcus aureus*, penicillin-resistant *Streptococcus pneumoniae*, vancomycin-resistant enterococci, fluoroquinolone-resistant *E. coli*, cephalosporin-resistant aerobic gram-negative rods and imipenem-resistant *Pseudomonas aeruginosa*. These organisms are significant causes of nosocomial infections and are clearly associated with increasing morbidity and mortality. The increasing numbers of elderly and immunocompromised patients are particularly at risk for infection with these pathogens. Therefore, there is a large unmet medical need for the development of new antimicrobial agents. In recent years Methicillin Resistant *Staphylococcus Aureus* (MRSA) infections have become more common, particularly in institutional and hospital settings. Up to 60% of *staphylococcus* infections are attributable to methicillin resistant strains in some parts of the United States. Some MRSA strains are now resistant to both Vancomycin and Gentamicin, drugs once considered the last defense against *staphylococcus* infections. Thus, there is a particularly urgent need for drugs effective against MRSA strains.

The utility of isothiazoloquinolines as pharmaceutical agents has been discussed in the literature. For example, Pinol, et al discussed the use of isothiazoloquinolines as medical bactericides in U.S. Pat. No. 5,087,621, including

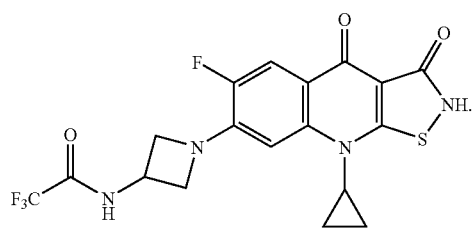

The Proctor & Gamble Company discussed antimicrobial quinolones including the following compound:

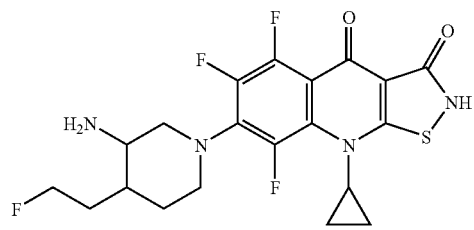

in published application no. US 2003008894.

The use of isothiazoloquinoline compounds as TNF production inhibitors has also been discussed, for example by Sankyo Co., Ltd. in JP1010149, which includes the following compound

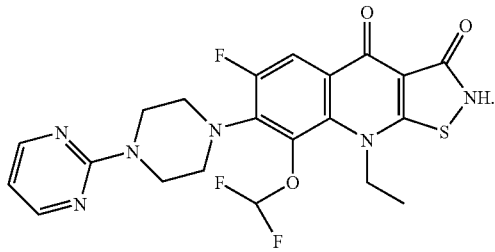

Bayer Aktiengesellschaft has discussed bicycle[3.3.0]oct-7-yl containing compounds useful for treating *H. pylori* infections in WO 98/26768, including isothiazoloquinolines, having the general structure shown below in which Y may be sulfur joined to the carboxamide group to form a 5-membered ring

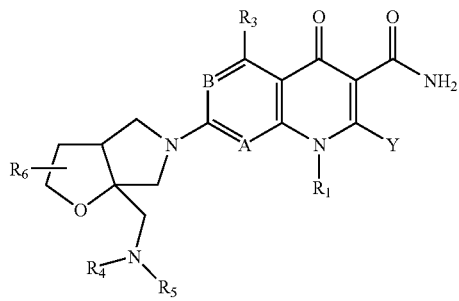

Otsuka Pharmaceutical Co., Ltd. has discussed the use of isothiazoloquinolines as antibacterial agents in JP 01193275, including the following carbamate-containing compound

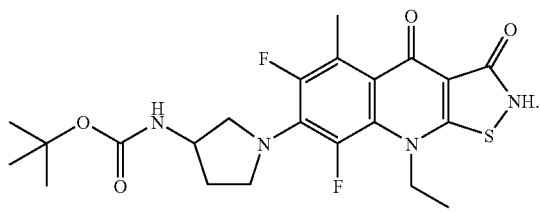

Abbott Laboratories has discussed the use of isothiazoloquinolines as anti-neoplastic agents in U.S. Pat. No. 5,071,848 and has discussed the use of tricyclic quinolones as antibacterial agents in U.S. Pat. No. 4,767,762. The Abbott compounds have hydrogen, halogen, or lower alkyl as substituents at the 6- and 8-positions of the isothiazoloquinoline core.

The present invention fulfills the need for drugs effective against MRSA bacterial strains, and provides further related advantages that are disclosed herein.

SUMMARY OF THE INVENTION

The invention provides compounds of Formula I and Formula II (shown below) and includes 8-methoxy-9H-isothiazolo[5,4-b]quinoline-3,4-diones and related compounds of Formula I and II, which possess antimicrobial activity. The invention provides compounds of Formula I and Formula II, which possess potent and/or selective antibacterial, antiprotozoal, or antifungal activity. The invention also provides compositions containing one or more compounds of Formula I or Formula II, or a salt, solvate, or prodrug, such as an acylated prodrug of such a compound, and one or more carriers, excipients, or diluents.

The invention further comprises methods of treating and preventing microbial infections, particularly bacterial and protozoal infections by administering an effective amount of a compound of Formula I or Formula II to an animal suffering from or susceptible to a microbial infection. These microbial infections include bacterial infections, for example *E. coli* infections, *Staphylococcus* infections, including Methicillin Resistant *Staphylococcus Aureus* infections, *Salmonella* infections and protozoal infections, for example *Chlamydia* infections. The invention is particularly includes methods of preventing or treating microbial infections in mammals, including humans, but also encompasses methods of preventing or treating microbial infections in other animals, including fish, birds, reptiles, and amphibians.

Methods of treatment include administering a compound of Formula I or Formula II as the single active agent or administering a compound of Formula I or Formula II in combination with one or more other therapeutic agent, such as an antibacterial, an antifungal, an antiviral, an interferon or other immune system modulator, an efflux-pump inhibitor, a beta-lactamase inhibitor, an anti-inflammatory, or another compound of Formula I or Formula II.

The invention also provides methods of inhibiting microbial growth and survival by applying an effective amount of an 8-methoxy-9H-isothiazolo[5,4-b]quinoline-3,4-dione or related compound. The invention includes, for example, methods of inhibiting microbial growth and survival on medical instruments or on surfaces used for food preparation by applying a composition containing a compound of Formula I or Formula II.

Thus, the invention include compounds and pharmaceutically acceptable salts of Formula I and Formula II, shown in the Detailed Description section, and includes certain preferred compounds of Formula A and B

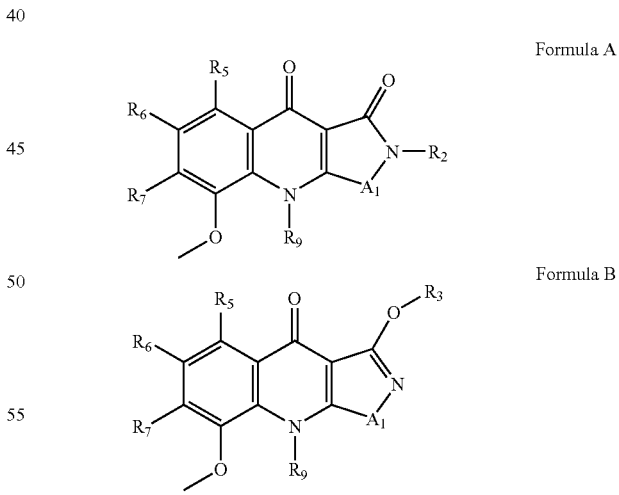

Within Formula A and Formula B the variables (e.g. $A_1$, $A_8$, $R_2$, $R_3$, and $R_5$ to $R_9$) carry the definitions, which follow.

$A_1$ is S, O, SO, or $SO_2$.

$R_2$ is hydrogen.

Or, $R_2$ is $C_1$-$C_8$alkyl, $C_2$-$C_6$alkenyl, $C_2$-$C_6$alkynyl, ($C_3$-$C_7$cycloalkyl)$C_0$-$C_4$carbohydryl, ($C_4$-$C_7$cycloalkenyl)$C_0$-$C_4$carbohydryl, (aryl)$C_0$-$C_4$carbohydryl, or ($C_2$-$C_6$heterocycloalkyl)$C_0$-$C_4$carbohydryl, each of which is substituted with 0 to 5 substituents independently chosen from halogen, hydroxy, amino, cyano, nitro, $C_1$-$C_4$alkyl, $C_1$-$C_4$alkoxy, $C_1$-$C_2$haloalkyl, $C_1$-$C_2$haloalkoxy, mono- and di-$C_1$-$C_4$alkylamino, $C_2$-$C_4$alkanoyl, $C_1$-$C_4$alkylthio, =$NOR_{10}$, =$NR_{10}$, —O(C=O)$R_{10}$, —(C=O)$NR_{10}R_{11}$, —O(C=O)$NR_{10}R_{11}$, —(C=O)$OR_{10}$, —(C=O)$NR_{10}OR_{11}$, —$NR_{10}$(C=O)$R_{11}$, —$NR_{10}$(C=O)$OR_{11}$, —$NR_{10}$(C=O)$NR_{11}R_{12}$, —$NR_{10}$(C=S)$NR_{11}R_{12}$, —$NR_{10}NR_{11}R_{12}$, —$SO_3R_{10}$, —(S=O)$OR_{10}$, —$SO_2R_{13}$, —$SO_2NR_{10}R_{11}$, and —$NR_{10}SO_2R_{13}$; where $R_{10}$, $R_{11}$, and $R_{12}$ are independently hydrogen, $C_1$-$C_4$alkyl, or aryl, and $R_{13}$ is $C_1$-$C_4$alkyl or aryl.

$R_3$ is hydrogen, $C_1$-$C_6$alkyl, $C_2$-$C_6$alkanoyl, mono- or di-$C_1$-$C_6$alkylcarbamate, or $C_1$-$C_6$alkylsulfonate; each of which is substituted with 0 to 3 substituents independently chosen from halogen, hydroxy, amino, cyano, nitro, $C_1$-$C_4$alkoxy, mono- and di-$C_1$-$C_4$alkylamino, $C_1$-$C_2$haloalkyl, and $C_1$-$C_2$haloalkoxy.

$R_5$ is hydrogen, halogen, hydroxy, amino, cyano, nitro, or —$NHNH_2$, or $R_5$ is $C_1$-$C_4$alkyl, $C_1$-$C_4$alkoxy, mono- or di-($C_1$-$C_4$alkyl)amino, mono-, di- or tri-$C_1$-$C_4$ alkylhydrazinyl, $C_2$-$C_4$alkanoyl, $C_1$-$C_4$alkylester, $C_1$-$C_2$haloalkyl, or $C_1$-$C_2$haloalkoxy; each of which is substituted with 0 to 3 substituents independently chosen from hydroxy, amino, halogen, oxo, $C_1$-$C_4$alkoxy, $C_1$-$C_2$haloalkyl, $C_1$-$C_2$haloalkoxy, and mono- and di-$C_1$-$C_4$alkylamino.

$R_6$ is hydrogen, halogen, hydroxy, amino, cyano, $C_1$-$C_4$alkyl, $C_1$-$C_4$alkoxy, mono- or di-($C_1$-$C_4$alkyl)amino, —$SO_3R_{10}$, —$SO_2R_{10}$, or —$SO_2NR_{10}R_{11}$.

$R_7$ is a nitrogen-linked heterocycloalkyl group, which has 4 to 8 ring members, including 0, 1, or 2 additional ring heteroatoms independently chosen from N, O, and S.

Or, $R_7$ is a nitrogen-linked $C_1$-$C_4$alkylamino substituted with a 5 or 6-membered heteroaryl group having 1 or 2 heteroatoms independently chosen from N, O, and S, or substituted with a heterocycloalkyl group, which has 4 to 8 ring members, including 1 or 2 ring heteroatoms independently chosen from N, O, and S.

Or, $R_7$ is a nitrogen-linked heterocycloalkyl or heterocycloalkenyl group, each of which has 4 to 8 ring members, including 0, 1, or 2 additional ring heteroatoms independently chosen from N, O, and S, forming part of a bicyclic system with a 3- to 8-membered cycloalkyl or heterocycloalkyl ring in fused or spiro orientation.

Or, $R_7$ is a nitrogen-linked 6-membered heterocycloalkyl group, 0, 1 or 2 additional ring heteroatoms independently chosen from N, O, and S, and bridged with a methylene or ethylene bridge.

Each of which $R_7$ is substituted with 0 or 1 or more substituents independently chosen from (a) and 0 or 1 substituents chosen from (b); wherein (a) is chosen from halogen, hydroxy, amino, nitro, $C_1$-$C_4$alkyl, $C_1$-$C_4$alkoxy, $C_1$-$C_2$haloalkyl, and $C_1$-$C_2$haloalkoxy, and (b) is oxo, amino, cyano, hydroxy$C_1$-$C_4$alkyl, amino$C_1$-$C_4$alkyl, $C_1$-$C_6$alkylthio, $C_2$-$C_6$alkanoyl, (mono- or di-$C_1$-$C_4$alkyl)amino$C_0$-$C_4$alkyl, ($C_3$-$C_7$cycloalkyl)$C_0$-$C_4$alkyl, ($C_3$-$C_7$cycloalkylamino)$C_0$-$C_4$alkyl, ($C_3$-$C_7$cycloalkyl)($C_1$-$C_4$alkyl)amino$C_0$-$C_4$alkyl, (heterocycloalkyl)$C_0$-$C_4$alkyl, or (aryl)$C_0$-$C_4$alkyl, where each of (b) other than oxo and cyano is substituted with 0 to 2 substituents independently chosen from halogen, hydroxy, amino, cyano, nitro, oxo, —COOH, —$CONH_2$, $C_1$-$C_4$alkyl, $C_2$-$C_4$alkenyl, $C_2$-$C_4$alkynyl, $C_1$-$C_4$alkoxy, mono- and di-($C_1$-$C_4$alkyl)amino, $C_1$-$C_2$haloalkyl, and $C_1$-$C_2$haloalkoxy.

$R_9$ is $C_1$-$C_8$alkyl, ($C_3$-$C_7$cycloalkyl)$C_0$-$C_4$alkyl, or phenyl, each of which is substituted with 0 to 3 substituents independently chosen from halogen, hydroxy, amino, cyano, nitro, —COOH, —$CONH_2$, $C_1$-$C_4$alkyl, $C_2$-$C_4$alkenyl, $C_2$-$C_4$alkynyl, $C_1$-$C_4$alkoxy, ($C_3$-$C_7$cycloalkyl)$C_0$-$C_4$alkyl, ($C_3$-$C_7$cycloalkyl)$C_0$-$C_4$alkoxy, mono- and di-($C_1$-$C_4$alkyl)amino, $C_1$-$C_2$haloalkyl, $C_1$-$C_2$haloalkoxy, and $C_2$-$C_4$alkanoyl.

DETAILED DESCRIPTION OF THE INVENTION

Chemical Description and Terminology

Prior to setting forth the invention in detail, it may be helpful to provide definitions of certain terms to be used herein. Compounds of the present invention are generally described using standard nomenclature.

In certain situations, the compounds of Formula I and Formula II may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms, with all isomeric forms of the compounds being included in the present invention. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column.

Where a compound exists in various tautomeric forms, the invention is not limited to any one of the specific tautomers, but rather includes all tautomeric forms.

The present invention is intended to include all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

Certain compounds are described herein using a general formula that includes variables, e.g. $A_1$, $R_2$, $R_3$, $R_5$, $R_6$, $R_7$, $A_8$, and $R_9$. Unless otherwise specified, each variable within such a formula is defined independently of other variables. Thus, if a group is said to be substituted, e.g. with 0-2 R*, then said group may be substituted with up to two R* groups and R* at each occurrence is selected independently from the definition of R*. Also, combinations of substituents and/or variables are permissible only if such combinations result in stable compounds. When a group is substituted by an "oxo" substituent a carbonyl bond replaces two hydrogen atoms on a carbon. An "oxo" substituent on an aromatic group or heteroaromatic group destroys the aromatic character of that group, e.g. a pyridyl substituted with oxo is a pyridone.

The term "substituted," as used herein, means that any one or more hydrogens on the designated atom or group is replaced with a selection from the indicated group, provided that the designated atom's normal valence is not exceeded. When a substituent is oxo (i.e., =O), then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent. Unless otherwise specified substituents are named into the core structure. For example, it is to be understood that when (cycloalkyl)alkyl is listed as a possible substituent the point of attachment of this substituent to the core structure is in the alkyl portion.

The exception to naming substituents into the ring is when the substituted is listed with a dash ("-") or double bond ("=") that is not between two letters or symbols. In that case the dash or double bond symbol is used to indicate a point of attachment for a substituent. For example, —$CONH_2$ is attached through the carbon atom.

As used herein, "alkyl" is intended to include both branched and straight-chain saturated aliphatic hydrocarbon groups, having the specified number of carbon atoms. Thus, the term $C_1$-$C_6$ alkyl as used herein includes alkyl groups having from 1 to about 6 carbon atoms. When $C_0$-$C_n$ alkyl is used herein in conjunction with another group, for example, (aryl)$C_0$-$C_4$ alkyl, the indicated group, in this case aryl, is either directly bound by a single covalent bond ($C_0$), or attached by an alkyl chain having the specified number of carbon atoms, in this case from 1 to about 4 carbon atoms. Examples of alkyl include, but are not limited to, methyl, ethyl, n-propyl, isopropyl, n-butyl, t-butyl, n-pentyl, and sec-pentyl.

"Alkenyl" as used herein, indicates a hydrocarbon chain of either a straight or branched configuration having one or more carbon-carbon double bond bonds, which may occur at any stable point along the chain. Examples of alkenyl groups include ethenyl and propenyl.

"Alkynyl" as used herein, indicates a hydrocarbon chain of either a straight or branched configuration having one or more triple carbon-carbon bonds that may occur in any stable point along the chain, such as ethynyl and propynyl.

"Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. An "(alkoxy)alkyl group is an alkoxy group as defined herein attached through its oxygen atom to an alkyl bridge where the point of attachment to the substituted group is in the alkyl group.

"Alkanoyl" indicates an alkyl group as defined above, attached through a keto (—(C=O)—) bridge. Alkanoyl groups have the indicated number of carbon atoms, with the carbon of the keto group being included in the numbered carbon atoms. For example a $C_2$alkanoyl group is an acetyl group having the formula $CH_3(C=O)$—.

As used herein, the terms "mono- or di-alkylamino" and "mono- and di-alkylamino" indicate secondary or tertiary alkyl amino groups, wherein the alkyl groups are as defined above and have the indicated number of carbon atoms. The point of attachment of the alkylamino group is on the nitrogen. Examples of mono- and di-alkylamino groups include ethylamino, dimethylamino, and methyl-propyl-amino. A mono- or di-($C_3$-$C_6$alkyl)($C_0$-$C_4$alkyl)amino group is an alkyl amino substituent in which a first alkyl group is chosen from $C_3$-$C_6$alkyl and an second alkyl group is chosen from $C_0$-$C_4$alkyl, wherein $C_0$ indicates the absence of a second alkyl group, i.e. a mono-$C_3$-$C_6$alkylamino.

The term "mono- or di-alkylcarbamate" indicates 1 or 2 independently chosen alkyl groups, as define above, attached through a carbamate (—O(C=O)NRR) linkage where R represents the alkyl groups. Mono-alkylcarbamate groups have the formula (—O(C=O)NHR).

The term "alkylester" indicates an alkyl group as define above attached through an ester linkage. The ester linkage may be in either orientation, e.g. a group of the formula —O(C=O)alkyl or a group of the formula —C=O)Oalkyl.

The term "mono-, di-, or tri-alkylhydrazinyl" indicates from 1 to 3 independently chosen alkyl groups as defined above attached through a single-bonded nitrogen-nitrogen linkage. At least one of the alkyl groups is attached to the terminal nitrogen (the nitrogen not bound to the core structure). When the term mono- or di-alkylhydrazinyl is used only the terminal nitrogen is alkyl substituted. Examples of alkylhydrazinyl groups include 2-butyl-1-hydrazinyl, 2-butyl-2-methyl-1-hydrazinyl, and 1,2-dimethyl-2-propyl-1-hydrazinyl.

The term "alkylsulfonate" indicates an alkyl group as defined above attached through a sulfonate linkage (e.g. a group of the —S(=O)$_2$O-alkyl).

The term "alkylthio" indicates an alkyl group as defined above attached through a sulfur linkage, i.e. a group of the formula alkyl-S—. Examples include ethylthio and pentylthio.

As used herein, the term "aminoalkyl" indicates an alkyl group as defined above substituted with at least one amino substituent. Similarly, the term "hydroxyalkyl" indicates an alkyl group as defined above, substituted with at least one hydroxyl substituent. In certain instances the alkyl group of the aminoalkyl or hydroxyalkyl group may be further substituted.

As used herein, the term "aryl" indicates aromatic groups containing only carbon in the aromatic ring or rings. Typical aryl groups contain 1 to 3 separate, fused, or pendant rings and from 6 to about 18 ring atoms, without heteroatoms as ring members. When indicated, such aryl groups may be further substituted with carbon or non-carbon atoms or groups. Such substitution may include fusion to a 5 to 7-membered saturated cyclic group that optionally contains 1 or 2 heteroatoms independently chosen from N, O, and S, to form, for example, a 3,4-methylenedioxy-phenyl group. Aryl groups include, for example, phenyl, naphthyl, including 1-naphthyl and 2-naphthyl, and bi-phenyl.

In the term "(aryl)alkyl," aryl and alkyl are as defined above, and the point of attachment is on the alkyl group. This term encompasses, but is not limited to, benzyl, phenylethyl, and piperonyl. Likewise, in the term (aryl)carbohydryl, aryl and carbohydryl are as defined above and the point of attachment is on the carbohydryl group, for example a phenylpropen-1-yl group. Similarly, in the term (aryl)alkoxy, aryl and alkoxy are as defined above and the point of attachment is through the oxygen atom of the alkoxy group; if the alkoxy is a $C_0$alkoxy the aryl is attached through an oxygen bridge.

"Carbohydryl" as used herein, includes both branched and straight-chain hydrocarbon groups, which are saturated or unsaturated, having the specified number of carbon atoms. When $C_0$-$C_n$carbohydryl is used herein in conjunction with another group, for example, (cycloalkyl)$C_0$-$C_4$carbohydryl, the indicated group, in this case cycloalkyl, is either directly bound by a single covalent bond ($C_0$), or attached by a carbohydryl chain, such as an alkyl chain, having the specified number of carbon atoms, in this case from 1 to about 4 carbon atoms. Examples of carbohydryl groups include $C_1$-$C_6$alkyl, such as methyl, or 5-butyl, $C_2$-$C_6$alkynyl such and hexynyl, and $C_2$-$C_6$ alkenyl, such as 1-propenyl.

"Cycloalkyl" as used herein, indicates a saturated hydrocarbon ring group, having only carbon ring atoms and having the specified number of carbon atoms, usually from 3 to about 8 ring carbon atoms, or from 3 to about 7 carbon atoms.

Examples of cycloalkyl groups include cyclopropyl, cyclobutyl, cyclopentyl, or cyclohexyl as well as bridged or caged saturated ring groups such as norborane or adamantane.

"Cycloalkenyl" as used herein, indicates an unsaturated, but not aromatic, hydrocarbon ring having at least one carbon-carbon double bond. Cycloalkenyl groups contain from 4 to about 8 carbon atoms, usually from 4 to about 7 carbon atoms. Examples include cyclohexenyl and cyclobutenyl.

In the terms "(cycloalkyl)alkyl," "(cycloalkyl)carbohydryl)," and "(cycloalkyl)alkoxy" the terms cycloalkyl, alkyl, carbohydryl, and alkoxy are as defined above, and the point of attachment is on the alkyl, carbohydryl, or alkoxy group respectively. These terms include examples such as cyclopropylmethyl, cyclohexylmethyl, cyclohexylpropenyl, and cyclopentylethyoxy.

In the terms "(cycloalkenyl)alkyl" and "(cycloalkenyl)carbohydryl" the terms cycloalkenyl, alkyl, and carbohydryl are as defined above, and the point of attachment is on the alkyl or carbohydryl group respectively. These terms include examples such as cyclobutenylmethyl, cyclohexenylmethyl, and cyclohexylpropenyl.

"Haloalkyl" indicates both branched and straight-chain saturated aliphatic hydrocarbon groups having the specified number of carbon atoms, substituted with 1 or more halogen atoms, generally up to the maximum allowable number of halogen atoms. Examples of haloalkyl include, but are not limited to, trifluoromethyl, difluoromethyl, 2-fluoroethyl, and penta-fluoroethyl.

"Haloalkoxy" indicates a haloalkyl group as defined above attached through an oxygen bridge.

"Halo" or "halogen" as used herein refers to fluoro, chloro, bromo, or iodo.

As used herein, "heteroaryl" indicates a stable 5- to 7-membered monocyclic or 7- to 10-membered bicyclic heterocyclic ring which contains at least 1 aromatic ring that contains from 1 to 4, or preferably from 1 to 3, heteroatoms chosen from N, O, and S, with remaining ring atoms being carbon. When the total number of S and O atoms in the heteroaryl group exceeds 1, these heteroatoms are not adjacent to one another. It is preferred that the total number of S and O atoms in the heteroaryl group is not more than 2. It is particularly preferred that the total number of S and O atoms in the heteroaryl group is not more than 1. A nitrogen atom in a heteroaryl group may optionally be quaternized. When indicated, such heteroaryl groups may be further substituted with carbon or non-carbon atoms or groups. Such substitution may include fusion to a 5 to 7-membered saturated cyclic group that optionally contains 1 or 2 heteroatoms independently chosen from N, O, and S, to form, for example, a [1,3]dioxolo[4,5-c]pyridyl group. Examples of heteroaryl groups include, but are not limited to, pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, benz[b]thiophenyl, isoquinolinyl, quinazolinyl, quinoxalinyl, thienyl, isoindolyl, and 5,6,7,8-tetrahydroisoquinoline.

In the terms "(heteroaryl)alkyl" and "(heteroaryl)carbohydryl," heteroaryl, alkyl, and carbohydryl are as defined above, and the point of attachment is on the alkyl or carbohydryl group respectively. These terms include such examples as pyridylmethyl, thiophenylmethyl, and (pyrrolyl)1-ethyl.

The term "heterocycloalkyl" indicates a saturated cyclic group containing from 1 to about 3 heteroatoms chosen from N, O, and S, with remaining ring atoms being carbon. Heterocycloalkyl groups have from 3 to about 8 ring atoms, and more typically have from 5 to 7 ring atoms. Examples of heterocycloalkyl groups include morpholinyl, piperazinyl, piperidinyl, and pyrrolidinyl groups. A nitrogen in a heterocycloalkyl group may optionally be quaternized.

The term "heterocyclic group" indicates a 5-6 membered saturated, partially unsaturated, or aromatic ring containing from 1 to about 4 heteroatoms chosen from N, O, and S, with remaining ring atoms being carbon or a 7-10 membered bicyclic saturated, partially unsaturated, or aromatic heterocylic ring system containing at least 1 heteroatom in the two ring system chosen from N, O, and S and containing up to about 4 heteroatoms independently chosen from N, O, and S in each ring of the two ring system. Unless otherwise indicated, the heterocyclic ring may be attached to its pendant group at any heteroatom or carbon atom that results in a stable structure. When indicated the heterocyclic rings described herein may be substituted on carbon or on a nitrogen atom if the resulting compound is stable. A nitrogen atom in the heterocycle may optionally be quaternized. It is preferred that the total number of heteroatoms in a heterocyclic groups is not more than 4 and that the total number of S and O atoms in a heterocyclic group is not more than 2, more preferably not more than 1. Examples of heterocyclic groups include, pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, benz[b]thiophenyl, isoquinolinyl, quinazolinyl, quinoxalinyl, thienyl, isoindolyl, dihydroisoindolyl, 5,6,7,8-tetrahydroisoquinoline, pyridinyl, pyrimidinyl, furanyl, thienyl, pyrrolyl, pyrazolyl, pyrrolidinyl, morpholinyl, piperazinyl, piperidinyl, and pyrrolidinyl.

Additional examples heterocyclic groups include, but are not limited to, phthalazinyl, oxazolyl, indolizinyl, indazolyl, benzothiazolyl, benzimidazolyl, benzofuranyl, benzoisoxolyl, dihydro-benzodioxinyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanonyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, 5 pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromanyl, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N oxide, indazolyl N-oxide, benzothiazolyl N-oxide, benzimidazolyl N-oxide, pyrrolyl N-oxide, oxadiazolyl N-oxide, thiadiazolyl N-oxide, tetrazolyl N-oxide, benzothiopyranyl S-oxide, and benzothiopyranyl S,S-dioxide.

As used herein "Active agents" are compounds that have pharmaceutical utility, e.g. may be used to treat a patient suffering from a disease or condition, or may be used prophylactically to prevent the onset of a disease or condition in a patient, or that may be used to enhance the pharmaceutical activity of other compounds.

"Pharmaceutical compositions" are compositions comprising at least one active agent, such as a compound or salt of Formula I or Formula II, and at least one other substance, such as a carrier, excipient, or diluent. Pharmaceutical compositions meet the U.S. FDA's GMP (good manufacturing practice) standards for human or non-human drugs.

"Salts" of the compounds of the present invention include inorganic and organic acid and base addition salts. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Salts of the present compounds further include solvates of the compounds and of the compound salts.

"Pharmaceutically acceptable salts" include derivatives of the disclosed compounds wherein the parent compound is modified by making non-toxic acid or base salts thereof, and further refers to pharmaceutically acceptable solvates of such compounds and such salts. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. Lists of additional suitable salts may be found, e.g., in *Remington's Pharmaceutical Sciences*, 17th ed., Mack Publishing Company, Easton, Pa., p. 1418 (1985).

The term "prodrugs" includes any compounds that become compounds of Formula I when administered to a mammalian subject, e.g., upon metabolic processing of the prodrug. Examples of prodrugs include, but are not limited to, acetate, formate and benzoate and like derivatives of functional groups (such as alcohol or amine groups) in the compounds of Formula I and Formula II.

The term "therapeutically effective amount" of a compound of this invention means an amount effective, when administered to a human or non-human patient, to provide a therapeutic benefit such as an amelioration of symptoms, e.g., an amount effective to decrease the symptoms of a microbial infection, and or an amount sufficient to reduce the symptoms of a bacterial, fungal, or protozoal infection. In certain circumstances a patient suffering from a microbial infection may not present symptoms of being infected. Thus a therapeutically effective amount of a compound is also an amount sufficient to prevent a significant increase or significantly reduce the detectable level of microorganism or antibodies against the microorganism in the patient's blood, serum, other bodily fluids, or tissues. The invention also includes using compounds of Formula I and Formula II in prophylactic therapies. In the context of prophylactic or preventative treatment a "therapeutically effective amount" is an amount sufficient to significantly decrease the treated animal's risk of contracting a microorganism infection. A significant reduction is any detectable negative change that is statistically significant, for example statistical significance can be measured in a standard parametric test of statistical significance such as Student's T-test, where $p<0.05$.

Antimicrobial Compounds

For the purposes of this document, the following numbering system will apply to the core 9H-isothiazolo[5,4-b]quinoline-3,4-dione (when $A_1$=sulfur) structure or core 9H-isoxazolo[5,4-b]quinoline-3,4-dione (when $A_1$=oxygen) structure. The numbers 1 through 9 refer specifically to positions within the tricyclic ring system whereas the letters A, B and C refer to the specific six (rings A and B) or five (ring C) member rings as shown below.

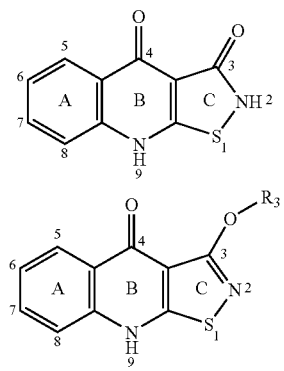

In addition to the compounds of Formula A and Formula B, described above the invention also includes compounds of Formula I and Formula II and the pharmaceutically acceptable salts thereof, in which the 8-position of the tricyclic structure is not required to be an aromatic carbon atom substituted with a methoxy, but is $A_8$.

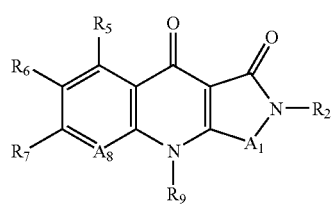

Formula I

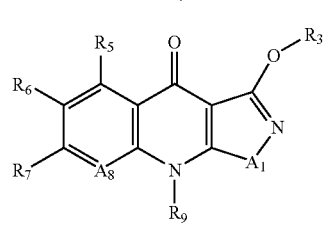

Formula II

Within Formula I and Formula II, $A_8$ is a nitrogen atom or $CR_8$ and $R_8$ is hydrogen, halogen, hydroxy, amino, cyano, nitro, or —$NHNH_2$, or $R_8$ is $C_1$-$C_4$alkyl, $C_1$-$C_4$alkoxy, mono- or di-($C_1$-$C_4$alkyl)amino, mono-, di-, or tri-$C_1$-$C_4$ alkylhydrazinyl, $C_2$-$C_4$alkanoyl, $C_1$-$C_4$alkylester, $C_1$-$C_2$haloalkyl, or $C_1$-$C_2$haloalkoxy; each of which is substituted with 0 to 3 substituents independently chosen from hydroxy, amino, halogen, oxo, $C_1$-$C_4$alkoxy, $C_1$-$C_2$haloalkyl, $C_1$-$C_2$haloalkoxy, and mono- and di-$C_1$-$C_4$alkylamino. Thus compounds of Formula A and B are preferred compounds of Formula I and Formula II in which $A_8$ is $CR_8$ and $R_8$ is methoxy. At each occasion "Formula I and/or Formula II" includes compounds of Formula A and Formula B.

The variables $A_1$, $A_8$, and $R_1$ to $R_9$ carry the definitions which follow.

$A_1$ is S, O, SO, or $SO_2$.

$R_2$ is hydrogen, or $R_2$ is $C_1$-$C_8$alkyl, $C_2$-$C_6$alkenyl, $C_2$-$C_6$alkynyl, $(C_3$-$C_7$cycloalkyl)$C_0$-$C_4$carbohydryl, $(C_4$-$C_7$cycloalkenyl)$C_0$-$C_4$carbohydryl, (aryl)$C_0$-$C_4$carbohydryl, or $(C_2$-$C_6$heterocycloalkyl)$C_0$-$C_4$carbohydryl, each of which is substituted with 0 to 5 substituents independently chosen from halogen, hydroxy, amino, cyano, nitro, $C_1$-$C_4$alkyl, $C_1$-$C_4$alkoxy, $C_1$-$C_2$haloalkyl, $C_1$-$C_2$haloalkoxy, mono- and di-$C_1$-$C_4$alkylamino, $C_2$-$C_4$alkanoyl, $C_1$-$C_4$alkylthio, $=NOR_{10}$, $=NR_{10}$, $-O(C=O)R_{10}$, $-(C=O)NR_{10}R_{11}$, $-O(C=O)NR_{10}R_{11}$, $-(C=O)OR_{10}$, $-(C=O)NR_{10}OR_{11}$, $-NR_{10}(C=O)R_{11}$, $-NR_{10}(C=O)OR_{11}$, $-NR_{10}(C=O)NR_{11}R_{12}$, $-NR_{10}(C=S)NR_{11}R_{12}$, $-NR_{10}NR_{11}R_{12}$, $-SO_3R_{10}$, $-(S=O)OR_{10}$, $-SO_2R_{13}$, $-SO_2NR_{10}R_{11}$, and $-NR_{10}SO_2R_{13}$; where $R_{10}$, $R_{11}$, and $R_{12}$ are independently hydrogen, $C_1$-$C_4$alkyl, or aryl, and $R_{13}$ is $C_1$-$C_4$alkyl or aryl.

$R_3$ is hydrogen, $C_1$-$C_6$alkyl, $C_2$-$C_6$alkanoyl, mono- or di-$C_1$-$C_6$alkylcarbamate, or $C_1$-$C_6$alkylsulfonate; each of which is substituted with 0 to 3 substituents independently chosen from halogen, hydroxy, amino, cyano, nitro, $C_1$-$C_4$alkoxy, mono- and di-$C_1$-$C_4$alkylamino, $C_1$-$C_2$haloalkyl, and $C_1$-$C_2$haloalkoxy.

$R_5$ is hydrogen, halogen, hydroxy, amino, cyano, nitro, or $-NHNH_2$, or $R_5$ is $C_1$-$C_4$alkyl, $C_1$-$C_4$alkoxy, mono- or di-$(C_1$-$C_4$alkyl)amino, mono-, di- or tri-$C_1$-$C_4$ alkylhydrazinyl, $C_2$-$C_4$alkanoyl, $C_1$-$C_4$alkylester, $C_1$-$C_2$haloalkyl, or $C_1$-$C_2$haloalkoxy; each of which is substituted with 0 to 3 substituents independently chosen from hydroxy, amino, halogen, oxo, $C_1$-$C_4$alkoxy, $C_1$-$C_2$haloalkyl, $C_1$-$C_2$haloalkoxy, and mono- and di-$C_1$-$C_4$alkylamino.

$R_6$ is hydrogen, halogen, hydroxy, amino, cyano, $C_1$-$C_4$alkyl, $C_1$-$C_4$alkoxy, mono- or di-$(C_1$-$C_4$alkyl)amino, $-SO_3R_{10}$, $-SO_2R_{10}$, or $-SO_2NR_{10}R_{11}$.

$R_7$ is a nitrogen-linked heterocycloalkyl or heterocycloalkenyl group, each of which has 4 to 8 ring members, including 0, 1 or 2 additional ring heteroatoms independently chosen from N, O, and S, each of which heterocycloalkyl or heterocycloalkenyl group is substituted with at least one group (ii) and is substituted with 0 or 1 or more of (i) and (iii).

Or, $R_7$ is a nitrogen-linked $C_1$-$C_4$alkylamino substituted with a 5 or 6-membered heteroaryl group having 1 or 2 heteroatoms independently chosen from N, O, and S, or substituted with a heterocycloalkyl group or heterocycloalkenyl group, each of which has 4 to 8 ring members, including 1 or 2 ring heteroatoms independently chosen from N, O, and S, each of which heteroaryl, heterocycloalkyl, or heterocycloalkenyl group is substituted with 0 or 1 or more substituents independently chosen from (i), (ii), and (iii).

Or, $R_7$ is a nitrogen-linked heterocycloalkyl or heterocycloalkenyl group, each of which has 4 to 8 ring members, including 0, 1, or 2 additional ring heteroatoms independently chosen from N, O, and S, which heterocycloalkyl or heterocycloalkenyl groups forms part of a bicyclic system with a 3- to 8-membered carbocyclic or heterocyclic ring in fused or spiro orientation, and is substituted with 0 or 1 or more substituents independently chosen from (i), (ii), and (iii), wherein $R_7$ is not 5H-furo[2,3-c]pyrrol-5-yl].

Or, $R_7$ is a nitrogen-linked heterocycloalkyl group, having 5 to 8 ring members, including 0, 1 or 2 additional ring heteroatoms independently chosen from N, O, and S, and bridged with a methylene or ethylene bridge, with the proviso that when $R_7$ is a 2,5 methylene bridged piperazine it is substituted with at least one group (ii) or (iii).

Where:

(i) is chosen from halogen, hydroxy, amino, nitro, $C_1$-$C_2$alkyl, hydroxy$C_1$-$C_2$alkyl, amino$C_1$-$C_2$alkyl, mono- and di-$(C_1$-$C_2)$alkylamino, and $-CH_2CH_2F$, (ii) is chosen from oxo, cyano, $C_3$-$C_6$alkyl, $C_2$-$C_6$alkenyl, $C_2$-$C_6$alkynyl, $(C_1$-$C_6$alkoxy)$C_0$-$C_4$alkyl, mono- and di-$(C_3$-$C_6$alkyl)$(C_0$-$C_4$alkyl)amino, di-$(C_1$-$C_4$alkyl)amino$C_1$-$C_4$alkyl, mono- and di-alkylamino(branched $C_2$-$C_4$alkyl), $(C_3$-$C_7$cycloalkylamino)$C_1$-$C_4$alkyl, $C_1$-$C_2$haloalkyl other than $-CH_2CH_2F$, $C_1$-$C_2$haloalkoxy, $(C_3$-$C_7$cycloalkyl)$C_0$-$C_4$carbohydryl, $(C_3$-$C_7$cycloalkyl)$C_0$-$C_4$carbohydryl-O—, $(C_4$-$C_7$cycloalkenyl)$C_0$-$C_4$carbohydryl, (aryl)$C_0$-$C_6$carbohydryl, (aryl)$C_1$-$C_4$alkoxy, $(C_2$-$C_6$heterocycloalkyl)$C_0$-$C_4$carbohydryl, (heteroaryl)$C_0$-$C_6$carbohydryl other than unsubstituted pyrimidin-2-yl, $C_1$-$C_6$alkylthio, $=NR_{10}$, $-(C_0$-$C_4$alkyl)(C=O)$R_{10}$, $-(C_0$-$C_4$alkyl)O(C=O)$R_{10}$, $-(C_0$-$C_4$alkyl)(C=O)$NR_{10}R_{11}$, $-(C_0$-$C_4$alkyl)O(C=O)$NH_2$, $-(C_0$-$C_4$alkyl)O(C=O)$NR_{10}(C_1$-$C_4$alkyl), $-(C_0$-$C_4$alkyl)(C=O)$OR_{10}$, $-(C_0$-$C_4$alkyl)$NR_{10}(C=O)$R_{11}$ other than $-N(CH_2CH_3)(C=O)CF_3$, $-(C_0$-$C_4$alkyl)$NR_{10}(C=O)OR_{11}$ other than $-NH(C=O)OC_1$-$C_6$alkyl), $-(C_0$-$C_4$alkyl)$NR_{10}(C=O)NR_{11}R_{12}$, $-(C_0$-$C_4$alkyl)$NR_{10}(C=O)(C_1$-$C_4$alkyl)$NR_{11}(C=O)O$-$R_{12}$, $-(C_0$-$C_4$alkyl)$NR_{10}(C=S)NR_{11}R_{12}$, $-(C_0$-$C_4$alkyl)$NR_{10}NR_{11}R_{12}$, $-(C_0$-$C_4$alkyl)N$=NR_{13}$, $-(C_0$-$C_4$alkyl)$SO_3R_{10}$, $-(C_0$-$C_4$alkyl)$(S=O)OR_{10}$, $-(C_0$-$C_4$alkyl)$SO_2R_{13}$, $-(C_0$-$C_4$alkyl)$SO_2NR_{10}R_{11}$, and $-(C_0$-$C_4$alkyl)$NR_{10}SO_2R_{13}$; and (iii) is chosen from $-OR_D$, $-(C=O)R_D$, $-SO_2R_D$, $-SO_3R_D$, $-NR_{10}SO_2R_D$, where $R_D$ is $C_1$-$C_4$alkyl, $(C_3$-$C_7$cycloalkyl)$C_0$-$C_2$alkyl, $(C_2$-$C_6$heterocycloalkyl)$C_0$-$C_2$alkyl, (aryl)$C_0$-$C_2$alkyl, or (heteroaryl)$C_0$-$C_2$alkyl; where each of (ii) other than oxo and cyano and each of (iii) is substituted with 0 to 3 substituents independently chosen from hydroxy, amino, cyano, nitro, oxo, $-COOH$, $-CONH_2$, $C_1$-$C_4$alkyl, $C_2$-$C_4$alkenyl, $C_2$-$C_4$alkynyl, $C_1$-$C_4$alkoxy, $C_1$-$C_4$alkoxycarbonyl, $(C_3$-$C_7$cycloalkyl)$C_0$-$C_4$carbohydryl, $(C_3$-$C_7$cycloalkyl)$C_0$-$C_4$alkoxy, $(C_3$-$C_7$cycloalkyl)$C_0$-$C_2$alkylamino, (heterocycloalkyl)$C_0$-$C_2$alkylamino, mono- and di-$(C_1$-$C_4$alkyl)amino, $C_1$-$C_2$haloalkyl, $C_1$-$C_2$haloalkoxy, $C_2$-$C_4$alkanoyl, and phenyl.

$A_8$ is N or $CR_8$.

$R_8$ is hydrogen, halogen, hydroxy, amino, cyano, nitro, or $-NHNH_2$.

Or, $R_8$ is $C_1$-$C_4$alkyl, $C_1$-$C_4$alkoxy, mono- or di-$(C_1$-$C_4$alkyl)amino, mono-, di-, or tri-$C_1$-$C_4$ alkylhydrazinyl, $C_2$-$C_4$alkanoyl, $C_1$-$C_4$alkylester, $C_1$-$C_2$haloalkyl, or $C_1$-$C_2$haloalkoxy; each of which is substituted with 0 to 3 substituents independently chosen from hydroxy, amino, halogen, oxo, $C_1$-$C_4$alkoxy, $C_1$-$C_2$haloalkyl, $C_1$-$C_2$haloalkoxy, and mono- and di-$C_1$-$C_4$alkylamino.

$R_9$ is $C_1$-$C_8$alkyl, $(C_3$-$C_7$cycloalkyl)$C_0$-$C_4$alkyl, or phenyl, each of which is substituted with 0 to 3 substituents independently chosen from halogen, hydroxy, amino, cyano, nitro, $-COOH$, $-CONH_2$, $C_1$-$C_4$alkyl, $C_2$-$C_4$alkenyl, $C_2$-$C_4$alkynyl, $C_1$-$C_4$alkoxy, $(C_3$-$C_7$cycloalkyl)$C_0$-$C_4$alkyl, $(C_3$-$C_7$cycloalkyl)$C_0$-$C_4$alkoxy, mono- and di-$(C_1$-$C_4$alkyl)amino, $C_1$-$C_2$haloalkyl, $C_1$-$C_2$haloalkoxy, and $C_2$-$C_4$alkanoyl.

The invention further provides compounds and salts of Formula I and Formula II in which the variables (e.g. $A_1$, $R_2$, $R_3$, $R_4$, etc.) carry definitions other than those set forth above. Embodiments in which one or more of the following conditions is met are included in the invention:

The $A_1$ Variable (1) $A_1$ is S; e.g. compounds and salts of Formula III and Formula IV are included herein.

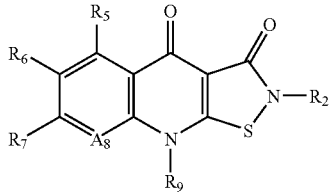
Formula III

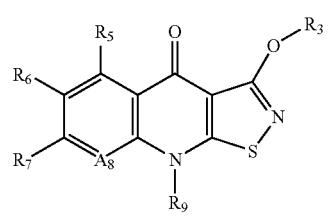
Formula IV (2) $A_1$ is SO; e.g. compounds and salts of Formula V and VI are included herein:

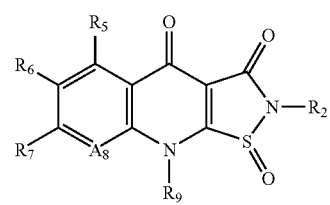
Formula V

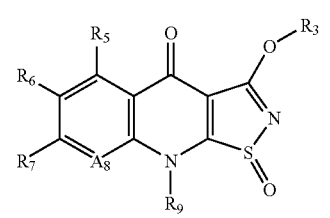
Formula VI (3) $A_1$ is $SO_2$; e.g. compounds and salts of Formula VII and VIII are included herein.

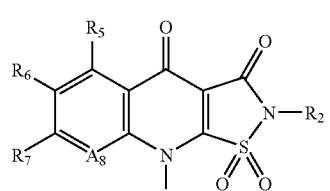
Formula VI

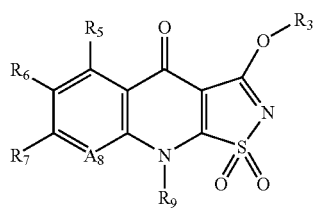
Formula VIII (4) $A_1$ is O; e.g. compounds and salts of Formula IX and X are included herein.

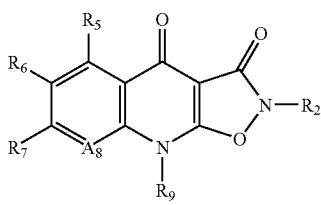
Formula IX

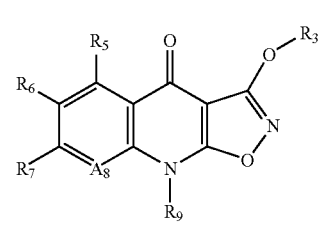
Formula X

The $R_2$ Variable (Compounds and Salts of Formula I):

(1) $R_2$ is hydrogen, or $R_2$ is $C_1$-$C_6$alkyl or ($C_3$-$C_7$cycloalkyl)$C_0$-$C_4$alkyl, each of which is substituted with at least one substituent chosen from hydroxy, amino, —COOH, —(C=O)$NR_{10}OR_{11}$, and —$CONH_2$; and is substituted with 0 to 3 substituents independently chosen from halogen, hydroxy, amino, cyano, nitro, —COOH, —$CONH_2$, $C_1$-$C_4$alkyl, $C_1$-$C_4$alkoxy, $C_1$-$C_2$haloalkyl, $C_1$-$C_2$haloalkoxy, and mono- and di-$C_1$-$C_4$alkylamino, and $C_2$-$C_4$alkanoyl.

(2) $R_2$ is hydrogen.

The $R_3$ Variable (Compounds and Salts of Formula II):

(1) $R_3$ is hydrogen, $C_1$-$C_6$alkyl or $C_2$-$C_6$alkanoyl, each of which is substituted with 0 to 3 substituents independently chosen from halogen, hydroxy, amino, cyano, $C_1$-$C_2$alkoxy, mono- and di-$C_1$-$C_2$alkylamino, $C_1$-$C_2$haloalkyl, and $C_1$-$C_2$haloalkoxy.

(2) $R_3$ is hydrogen, $C_1$-$C_6$alkyl, or $C_2$-$C_6$alkanoyl.

(3) $R_3$ is hydrogen.

(4) $R_3$ is $C_1$-$C_2$ alkyl.

The $R_5$ Variable (1) $R_5$ is hydrogen, hydroxy, amino, $C_1$-$C_2$alkyl, $C_1$-$C_2$alkoxy, mono- or di-($C_1$-$C_4$alkyl)amino, or mono- or di-$C_1$-$C_4$alkylhydrazinyl.

(2) $R_5$ is hydrogen, amino, mono- or di-($C_1$-$C_2$)alkylamino, or mono- or di-$C_1$-$C_2$ alkylhydrazinyl.

(3) $R_5$ is hydrogen.

The $R_6$ Variable (1) $R_6$ is hydrogen, halogen, or amino.

(2) $R_6$ is fluoro or hydrogen.

(3) $R_6$ is fluoro.

(4) $R_6$ is fluoro, and $A_8$ is $CR_8$ wherein $R_8$ is methoxy.

The $R_7$ Variable (1) $R_7$ is a nitrogen-linked heterocycloalkyl or heterocycloalkenyl group, each of which has 4- to 8-ring members, including 0, 1 or 2 additional ring heteroatoms independently chosen from N, O, and S, each of which heterocycloalkyl or heterocycloalkenyl group is substituted with at least one group (ii) and is substituted with 0 or 1 or more (i) or (iii); or $R_7$ is a nitrogen-linked $C_1$-$C_4$alkylamino substituted with a 5 or 6-membered heteroaryl group having 1 or 2 heteroatoms independently chosen from N, O, and S, or substituted with a heterocycloalkyl group, heterocycloalkenyl group, each of which has 4 to 8 ring members, including 1 or 2 ring heteroatoms independently chosen from N, O, and S, each of which heteroaryl, heterocycloalkyl, or heterocycloalkenyl group is substituted with 0 or 1 or more substituents independently chosen from (i), (ii), and (iii); or $R_7$ is a nitrogen-linked heterocycloalkyl or heterocycloalkenyl group, each of which has 4 to 8 ring members, including 0, 1 or 2 additional ring heteroatoms independently chosen from N, O, and S, forming part of a bicyclic system with a 3- to 8-membered carbocyclic or heterocyclic ring in fused or spiro orientation, and is substituted with 0 or 1 or more substituents independently chosen from (i), (ii), and (iii); or $R_7$ is a nitrogen-linked heterocycloalkyl group, having 5 to 8 ring members, including 0, 1, or 2 additional ring heteroatoms independently chosen from N, O, and S, and bridged with a methylene or ethylene bridge, with the proviso that when $R_7$ is a 2,5 methylene bridged piperazine it is substituted with at least one group (ii).

Within this definition of $R_7$ (i) is chosen from halogen, hydroxy, amino, nitro, $C_1$-$C_2$alkyl, mono- and di-$(C_1$-$C_2)$alkylamino, and —$CH_2CH_2F$;

(ii) is chosen from cyano, oxo, $C_3$-$C_6$alkyl, $C_2$-$C_6$alkenyl, $C_2$-$C_6$alkynyl, ($C_1$-$C_4$alkoxy)$C_0$-$C_4$alkyl, mono- and di-$(C_3$-$C_6$alkyl)$(C_0$-$C_4$alkyl)amino, di-$(C_1$-$C_4$alkyl)amino$C_1$-$C_4$alkyl, mono- or di-alkylamino(branched $C_2$-$C_4$alkyl), ($C_3$-$C_7$cycloalkylamino)$C_1$-$C_4$alkyl, $C_1$-$C_2$haloalkyl other than —$CH_2CH_2F$, $C_1$-$C_2$haloalkoxy, ($C_3$-$C_7$cycloalkyl)$C_0$-$C_2$alkyl, ($C_3$-$C_7$cycloalkyl)$C_0$-$C_2$alkoxy, ($C_2$-$C_6$heterocycloalkyl)$C_0$-$C_2$alkyl, $C_1$-$C_6$alkylthio, =$NR_{10}$, —$(C_0$-$C_4$alkyl)(C=O)$R_{10}$; and (iii) is chosen from —$OR_D$, —(C=O)$R_D$, —$SO_2R_D$, —$SO_3R_D$, —$NR_{10}SO_2R_D$, where $R_D$ is $C_1$-$C_4$alkyl, ($C_3$-$C_7$cycloalkyl)$C_0$-$C_2$alkyl, ($C_2$-$C_6$heterocycloalkyl)$C_0$-$C_2$alkyl, (aryl)$C_0$-$C_2$alkyl, or (heteroaryl)$C_0$-$C_2$alkyl. Where each of (ii) and (iii) is substituted with 0 to 3 substituents independently chosen from halogen, hydroxy, amino, cyano, nitro, oxo, —COOH, —$CONH_2$, $C_1$-$C_4$alkyl, $C_2$-$C_4$alkenyl, $C_2$-$C_4$alkynyl, $C_1$-$C_4$alkoxy, ($C_3$-$C_7$cycloalkyl)$C_0$-$C_2$alkyl, ($C_3$-$C_7$cycloalkyl)$C_0$-$C_2$alkylamino, ($C_3$-$C_7$cycloalkyl)$C_0$-$C_4$alkoxy, mono- and di-$(C_1$-$C_4$alkyl)amino, $C_1$-$C_2$haloalkyl, $C_1$-$C_2$haloalkoxy, $C_2$-$C_4$alkanoyl, and phenyl.

(2) $R_7$ is a nitrogen-linked heterocycloalkyl or heterocycloalkenyl group, each of which has 4- to 8-ring members, including 0, 1, or 2 additional ring heteroatoms independently chosen from N, O, and S, each of which is substituted with at least one group (ii) and is substituted with 0 or 1 or more of (i) and (iii).

Within this definition of $R_7$ (i) is chosen from halogen, hydroxy, amino, nitro, $C_1$-$C_2$alkyl, mono- and di-$(C_1$-$C_2)$alkylamino, and —$CH_2CH_2F$;

(ii) is chosen from oxo and cyano, $C_3$-$C_6$alkyl, $C_2$-$C_6$alkenyl, $C_2$-$C_6$alkynyl, ($C_1$-$C_4$alkoxy)$C_0$-$C_4$alkyl, mono- and di-$(C_3$-$C_6$alkyl)$(C_0$-$C_4$alkyl)amino, di-$(C_1$-$C_4$alkyl)amino$C_1$-$C_4$alkyl, mono- and di-alkylamino (branched $C_2$-$C_4$alkyl), ($C_3$-$C_7$cycloalkylamino)$C_1$-$C_4$alkyl, $C_1$-$C_2$haloalkyl other than —$CH_2CH_2F$, $C_1$-$C_2$haloalkoxy, ($C_3$-$C_7$cycloalkyl)$C_0$-$C_2$alkyl, ($C_3$-$C_7$cycloalkyl)$C_0$-$C_2$alkoxy, ($C_2$-$C_6$heterocycloalkyl)$C_0$-$C_2$alkyl, $C_1$-$C_6$alkylthio, =$NR_{10}$, and —$(C_0$-$C_4$alkyl)(C=O)$R_{10}$; and (iii) is chosen from —$OR_D$, —(C=O)$R_D$, —$SO_2R_D$, —$SO_3R_D$, —$NR_{10}SO_2R_D$, where $R_D$ is $C_1$-$C_4$alkyl, ($C_3$-$C_7$cycloalkyl)$C_0$-$C_2$alkyl, ($C_2$-$C_6$heterocycloalkyl)$C_0$-$C_2$alkyl, (aryl)$C_0$-$C_2$alkyl, and (heteroaryl)$C_0$-$C_2$alkyl. Where each of (ii) other than oxo and cyano and each of (iii) is substituted with 0 to 3 substituents independently chosen from halogen, hydroxy, amino, cyano, nitro, oxo, —COOH, —$CONH_2$, $C_1$-$C_4$alkyl, $C_2$-$C_4$alkenyl, $C_2$-$C_4$alkynyl, $C_1$-$C_4$alkoxy, ($C_3$-$C_7$cycloalkyl)$C_0$-$C_2$alkyl, ($C_3$-$C_7$cycloalkyl)$C_0$-$C_2$alkylamino, ($C_3$-$C_7$cycloalkyl)$C_0$-$C_4$alkoxy, mono- and di-$(C_1$-$C_4$alkyl)amino, $C_1$-$C_2$haloalkyl, $C_1$-$C_2$haloalkoxy, $C_2$-$C_4$alkanoyl, and phenyl.

(3) $R_7$ is a 4-, 5-, or 6-membered nitrogen-linked heterocycloalkyl, which has 0 or 1 additional nitrogen atoms, which 4-, 5-, or 6-membered nitrogen-linked heterocycloalkyl is substituted with 0 to 2 substituents independently chosen from (i) and one substituent (ii).

Within this embodiment (i) is chosen from halogen, hydroxy, amino, $C_1$-$C_2$alkyl, hydroxy$C_1$-$C_2$alkyl, amino$C_1$-$C_2$alkyl, and cyano, and (ii) is chosen from oxo, cyano, $C_3$-$C_4$alkyl, $C_2$-$C_6$alkenyl, ($C_1$-$C_4$alkoxy)$C_0$-$C_4$alkyl, mono- and di-$(C_3$-$C_6$alkyl)$(C_0$-$C_4$alkyl)amino, di-$(C_1$-$C_4$alkyl)amino$C_1$-$C_4$alkyl, mono- or di-alkylamino(branched $C_2$-$C_4$alkyl), ($C_3$-$C_7$cycloalkylamino)$C_1$-$C_4$alkyl, $C_1$-$C_2$haloalkyl other than —$CH_2CH_2F$, $C_1$-$C_2$haloalkoxy, ($C_3$-$C_7$cycloalkyl)$C_0$-$C_2$alkyl, ($C_2$-$C_6$heterocycloalkyl)$C_0$-$C_2$alkyl, =$NR_{10}$, and —$(C_0$-$C_4$alkyl)(C=O)$R_{10}$. Where each of (ii) other than oxo and cyano is substituted with substituted with 0 to 3 substituents independently chosen from halogen, hydroxy, amino, cyano, oxo, —$C_1$-$C_4$alkyl, $C_2$-$C_4$alkenyl, $C_1$-$C_4$alkoxy, ($C_3$-$C_7$cycloalkyl)$C_0$-$C_2$alkyl, ($C_3$-$C_7$cycloalkyl)$C_0$-$C_2$alkylamino, mono- and di-$(C_1$-$C_4$alkyl)amino, $C_1$-$C_2$haloalkyl, and $C_1$-$C_2$haloalkoxy.

(4) $R_7$ is a pyrrolidinyl, piperidinyl, piperazinyl, morpholinyl, thiomorpholinyl, or azepanyl group substituted with at least one group (ii) and substituted with 0 or one or more of (i) and (iii). Here (i) and (iii) carry any of the definitions set forth above.

(5) $R_7$ is a pyrrolidinyl or piperazinyl group substituted with one group (ii) and 0, 1, or 2 substituents independently chosen from halogen, hydroxy, trifluoromethyl, or trifluoromethoxy, wherein (ii) is oxo, cyano, $C_2$-$C_4$alkanoyl or (ii) $C_3$-$C_7$cycloalkyl substituted with 0 or 1 $C_1$-$C_2$alkyl or amino substituents, or (ii) is $C_3$-$C_6$alkyl, di-$(C_1$-$C_4$alkyl)amino$C_1$-$C_4$alkyl, mono- or di-alkylamino(branched $C_2$-$C_4$alkyl), or ($C_3$-$C_7$cycloalkylamino)$C_1$-$C_4$alkyl, each of which is substituted with 0, 1 or 2 substituents independently chosen from amino, hydroxy, ($C_3$-$C_7$cycloalkyl)$C_0$-$C_2$alkyl, ($C_3$-$C_7$cycloalkyl)$C_0$-$C_2$alkylamino, and (heterocycloalkyl)$C_0$-$C_2$alkylamino.

(6) $R_7$ is a pyrrolidinyl or piperazinyl group substituted with one group (ii) and optionally substituted with 1 methyl or halogen substituent wherein (ii) is $C_3$-$C_7$cycloalkyl which is unsubstituted or substituted with one amino substituent, or (ii) is $C_3$-$C_6$alkyl substituted with 1 amino, hydroxy, $C_3$-$C_7$cycloalkyl, or ($C_3$-$C_7$cycloalkyl)$C_0$-$C_2$alkylamino substituent, or (ii) is or di-$(C_1$-$C_4$alkyl)amino$C_1$-$C_4$alkyl, mono- or di-alkylamino(branched $C_2$-$C_4$alkyl) or ($C_3$-$C_7$cycloalkylamino)$C_1$-$C_4$alkyl, each of which is substituted with 0 or 1 $C_3$-$C_7$cycloalkyl.

(7) $R_7$ is a group of formula (a)-(e)

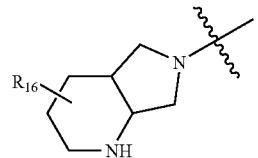

(a)

-continued

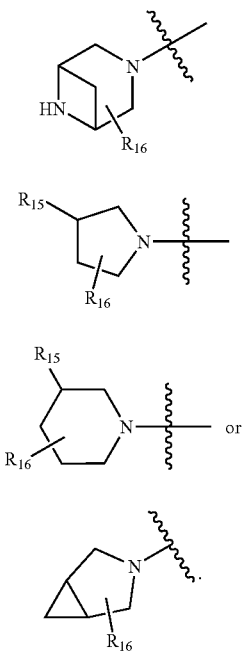

in which $R_{15}$ is (ii); and $R_{16}$ is 0 or 1 or more substituents independently chosen from chloro, fluoro, methyl, methoxy, aminomethyl, aminoethyl, trifluoromethyl, and trifluoromethoxy.

(8) $R_7$ is a group of formula (a)-(e) in which $R_{15}$ is oxo or cyano; or $R_{15}$ is $C_3$-$C_7$cycloalkyl substituted with 0 or 1 $C_1$-$C_2$alkyl or amino substituent, or $R_{15}$ is $C_3$-$C_6$ alkyl, di-($C_1$-$C_4$alkyl)amino$C_1$-$C_4$alkyl, mono- or di-alkylamino(branched $C_2$-$C_4$alkyl), or ($C_3$-$C_7$cycloalkylamino)$C_1$-$C_4$alkyl, each of which is substituted with 0, 1, or 2 substituents independently chosen from amino, hydroxy, and ($C_3$-$C_7$cycloalkyl)$C_0$-$C_2$alkyl; or $R_{15}$ is mono- or di-($C_3$-$C_6$alkyl)($C_0$-$C_4$alkyl)amino, or $R_{15}$ is =$NR_{10}$ or —($C_0$-$C_4$alkyl)(C=O)$R_{10}$, or —($C_0$-$C_4$alkyl)$NCH_3$(C=O)$OR_{11}$, where each $R_{10}$ and $R_{11}$ are hydrogen or $C_1$-$C_4$alkyl.

(9) $R_7$ is a group of formula (a)-(e) in which $R_{15}$ is $C_3$-$C_7$cycloalkyl which is unsubstituted or substituted with one amino substituent, or $R_{15}$ is $C_3$-$C_6$ alkyl, di-($C_1$-$C_4$alkyl)amino$C_1$-$C_4$alkyl, mono- or di-alkylamino (branched $C_2$-$C_4$alkyl) or ($C_3$-$C_7$cycloalkylamino)$C_1$-$C_4$alkyl, each of which is substituted with 0, 1, or 2 substituents independently chosen from amino, hydroxy, and ($C_3$-$C_7$cycloalkyl)$C_0$-$C_2$alkyl.

$R_{16}$ is 0 or 1 substituent chosen from chloro, fluoro, and methyl.

(10) $R_7$ is a group of formula (a)-(e) in which $R_{15}$ is cyclopropyl substituted with amino, or $R_{15}$ is $C_3$-$C_6$ alkyl substituted with amino or $C_3$-$C_5$cycloalkylamino, or $R_{15}$ is mono- or di-($C_1$-$C_4$alkyl)amino$C_1$-$C_4$alkyl.

$R_{16}$ is 0 or 1 substituent chosen from chloro, fluoro, and methyl.

(11) $R_7$ is a group of the formula

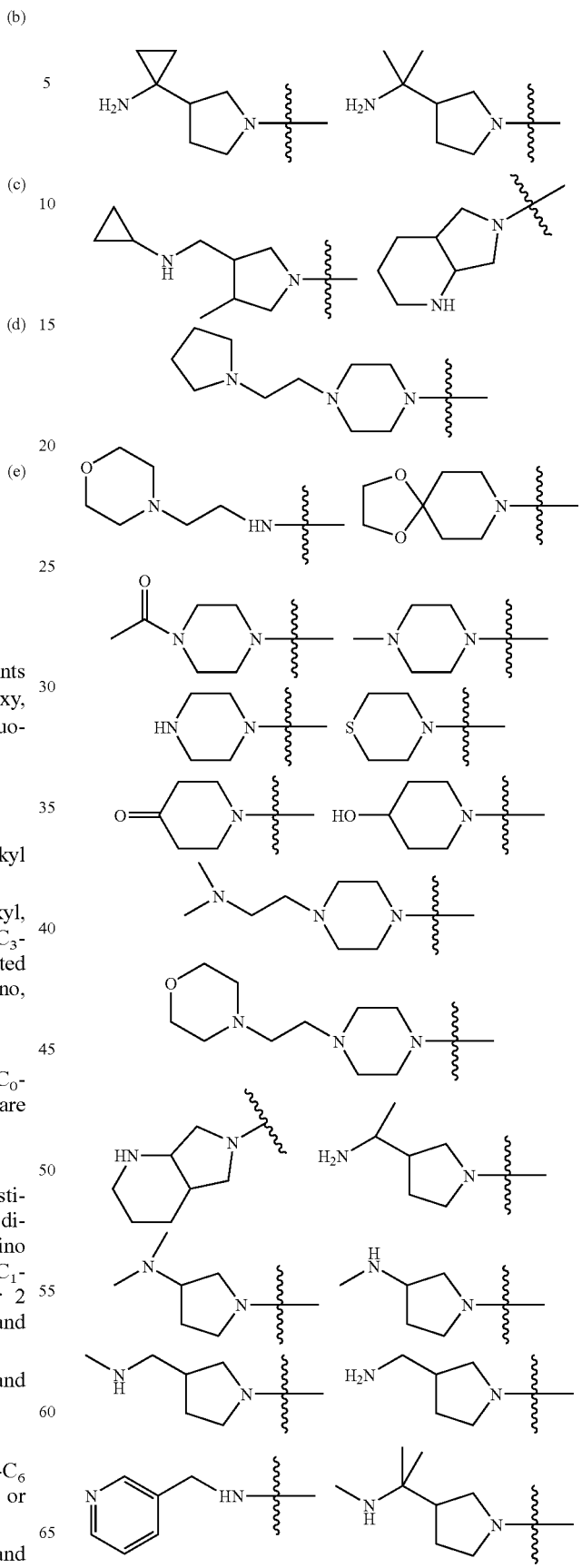

-continued

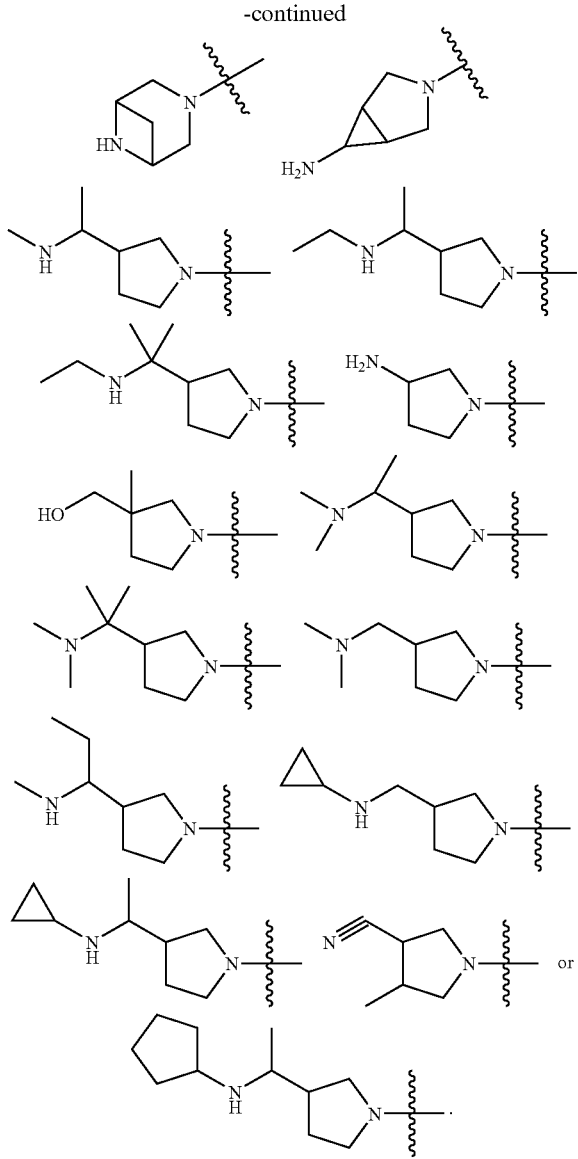

(12) $R_7$ is a nitrogen-linked $C_1$-$C_4$alkylamino substituted with a 5 or 6-membered heteroaryl group having 1 or 2 heteroatoms independently chosen from N, O, and S, or substituted with a heterocycloalkyl group, heterocycloalkenyl group, each of which has 4 to 8 ring members, and 1 or 2 ring heteroatoms independently chosen from N, O, and S, each of which heteroaryl, heterocycloalkyl, or heterocycloalkenyl group is substituted with 0 or 1 or more substituents independently chosen from (i), (ii), and (iii). Here (i), (ii), and (iii) carry any of the definitions set forth above.

(13) $R_7$ is an N-linked $C_1$-$C_4$alkylamino substituted with a 5- or 6-membered heteroaryl group having 1 or 2 heteroatoms independently chosen from N, O, and S, or substituted with a 5- or 6-membered heterocycloalkyl having 1 or 2 ring heteroatoms independently chosen from N, O, and S, each of which heteroaryl or heterocycloalkyl is substituted with 0, 1, or 2 substituents independently chosen from halogen, hydroxy, amino, oxo, cyano, $C_1$-$C_2$alkyl, $C_1$-$C_2$alkoxy, $C_1$-$C_2$haloalkyl, and $C_1$-$C_2$haloalkoxy.

(14) $R_7$ is $C_1$-$C_4$alkylamino substituted with a pyridyl, pyrimidinyl, pyrazinyl, imidazolyl, thienyl, pyrrolidinyl, furanyl, piperazinyl, piperidinyl, morpholinyl, thiomorpholinyl, or pyrrolidinyl, each of which is substituted with 0, 1, or 2 substituents independently chosen from halogen, hydroxy, amino, oxo, cyano, $C_1$-$C_2$alkyl, $C_1$-$C_2$alkoxy, $C_1$-$C_2$haloalkyl, and $C_1$-$C_2$haloalkoxy.

(15) $R_7$ is $C_1$-$C_2$alkylamino substituted with pyridyl, piperazinyl, piperidinyl, or morpholinyl, each of which is substituted with 0, 1, or 2 substituents independently chosen from halogen, methyl, and methoxy.

(16) $R_7$ is a nitrogen-linked heterocycloalkyl or heterocycloalkenyl group, each of which has 4 to 8 ring members, including 0, 1 or 2 additional ring heteroatoms independently chosen from N, O, and S, forming part of a bicyclic system with a 3- to 7-membered carbocyclic or heterocyclic ring in fused or spiro orientation, and is substituted with 0 or 1 or more substituents independently chosen from (i), (ii), and (iii). Here (i), (ii), and (iii) carry any of the definitions set forth above.

(17) $R_7$ is a group of the formula

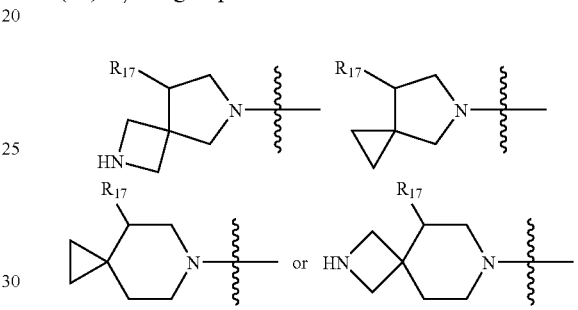

wherein $R_{17}$ is hydrogen, chloro, fluoro, amino, methyl, ethyl, methoxy, $C_1$-$C_6$ alkyl substituted with amino or hydroxy, mono- and di-($C_0$-$C_4$alkyl)amino; $=NR_{10}$, or —($C_0$-$C_4$alkyl)(C=O)$R_{10}$, where each $R_{10}$ is hydrogen or $C_1$-$C_4$alkyl.

(18) $R_7$ is a 5- or 6-membered nitrogen-linked heterocycloalkyl, which has 0 or 1 additional nitrogen atoms, which 5- or 6-membered nitrogen-linked heterocycloalkyl is part of a bicyclic ring system having a fused $C_3$-$C_6$cycloalkyl or a fused 4- to 6-membered heterocycloalkyl containing I nitrogen atom, which bicyclic ring system is substituted with 0 to 3 substituents independently chosen from (i) and (ii).

Within this embodiment (i) is chosen from halogen, hydroxy, and amino, and (ii) is chosen from $C_1$-$C_4$alkyl, $C_2$-$C_6$alkenyl, ($C_1$-$C_4$alkoxy)$C_0$-$C_4$alkyl, mono- and di-($C_1$-$C_4$alkyl)amino, $C_1$-$C_2$haloalkyl, $C_1$-$C_2$haloalkoxy, ($C_3$-$C_7$cycloalkyl)$C_0$-$C_2$alkyl, ($C_2$-$C_6$heterocycloalkyl)$C_0$-$C_2$alkyl, $=NR_{10}$, and —($C_0$-$C_4$alkyl)(C=O)$R_{10}$. Each of (ii) is substituted with substituted with 0 to 3 substituents independently chosen from halogen, hydroxy, amino, cyano, oxo, —$C_1$-$C_4$alkyl, $C_2$-$C_4$alkenyl, $C_1$-$C_4$alkoxy, ($C_3$-$C_7$cycloalkyl)$C_0$-$C_2$alkyl, mono- and di-($C_1$-$C_4$alkyl)amino, $C_1$-$C_2$haloalkyl, and $C_1$-$C_2$haloalkoxy.

In certain of these embodiments the 5- or 6-membered nitrogen-linked heterocycloalkyl which is part of a bicyclic ring system is a pyrrolidinyl or piperidinyl and is fused to a $C_3$-$C_6$cycloalkyl, pyrrolidinyl, or piperidinyl; in which the bicyclic ring is substituted with 0, 1, or 2 substituents independently chosen from halogen, methyl, or methoxy.

In certain of these embodiments the bicyclic ring system is a 3-aza-bicyclo[3.1.0]hexanyl or a octahydro-1H-pyrrolo[3,4-b]pyridinyl ring system.

(19) $R_7$ is a nitrogen-linked heterocycloalkyl group, having 5 to 8 ring members, including 0, 1 or 2 additional ring heteroatoms independently chosen from N, O, and S, and bridged with a methylene or ethylene bridge, with the proviso that when $R_7$ is a 2,5 methylene bridged piperazine it is substituted with at least one group (ii) or (iii) (other $R_7$ groups of this embodiment are optionally substituted with on ore more of (i), (ii), and (iii)). Wherein (i), (ii), and (iii) carry any of the definitions set forth above.

(20) $R_7$ is a bridged piperidinyl or bridged piperazinyl, each of which is substituted with 0 to 3 substituents independently chosen from (i) and (ii).

Within this embodiment (i) is chosen from halogen, hydroxy, and amino; and (ii) is chosen from oxo, cyano, $C_1$-$C_4$alkyl, $C_2$-$C_6$alkenyl, ($C_1$-$C_4$alkoxy)$C_0$-$C_4$alkyl, mono- and di-($C_1$-$C_4$alkyl)amino, $C_1$-$C_2$haloalkyl, $C_1$-$C_2$haloalkoxy, ($C_3$-$C_7$cycloalkyl)$C_0$-$C_2$alkyl, ($C_2$-$C_6$heterocycloalkyl)$C_0$-$C_2$alkyl, =$NR_{10}$, and —($C_0$-$C_4$alkyl)(C=O)$R_{10}$. Each of (ii) other than oxo and cyano is substituted with 0 to 3 substituents independently chosen from halogen, hydroxy, amino, cyano, oxo, $C_1$-$C_4$alkyl, $C_2$-$C_4$alkenyl, $C_1$-$C_4$alkoxy, ($C_3$-$C_7$cycloalkyl)$C_0$-$C_2$cycloalkyl, mono- and di-($C_1$-$C_4$alkyl)amino, $C_1$-$C_2$haloalkyl, and $C_1$-$C_2$haloalkoxy.

(21) $R_7$ is a bridged piperidinyl or bridged piperazinyl, each of which is substituted with 0 to 2 substituents independently chosen from halogen, hydroxy, amino, cyano, $C_1$-$C_2$alkyl, and $C_1$-$C_2$alkoxy.

(22) $R_8$ is methoxy; and
$R_7$ is a nitrogen-linked heterocycloalkyl group, which has 4 to 8 ring members, including 0, 1 or 2 additional ring heteroatoms independently chosen from N, O, and S which heterocycloalkyl, which $R_7$ is substituted with 0 or 1 or more substituents independently chosen from (a) and 0 or 1 substituents chosen from (b), wherein (a) is chosen from halogen, hydroxy, amino, nitro, $C_1$-$C_4$alkyl, $C_1$-$C_4$alkoxy, $C_1$-$C_2$haloalkyl, $C_1$-$C_2$haloalkoxy, (b) is oxo, amino, cyano, hydroxy$C_1$-$C_4$alkyl, amino$C_1$-$C_4$alkyl, $C_1$-$C_6$alkylthio, $C_2$-$C_6$alkanoyl, (mono- or di-$C_1$-$C_4$alkyl)amino$C_0$-$C_4$alkyl, ($C_3$-$C_7$cycloalkyl)$C_0$-$C_4$alkyl, ($C_3$-$C_7$cycloalkylamino)$C_0$-$C_4$alkyl, ($C_3$-$C_7$cycloalkyl)($C_1$-$C_4$alkyl)amino$C_0$-$C_4$alkyl, (heterocycloalkyl)$C_0$-$C_4$alkyl, or (aryl)$C_0$-$C_4$alkyl.

Each of (b) other than oxo and cyano is substituted with 0 to 2 substituents independently chosen from halogen, hydroxy, amino, cyano, nitro, oxo, —COOH, —CONH$_2$, $C_1$-$C_4$alkyl, $C_2$-$C_4$alkenyl, $C_2$-$C_4$alkynyl, $C_1$-$C_4$alkoxy, mono- and di-($C_1$-$C_4$alkyl)amino, $C_1$-$C_2$haloalkyl, and $C_1$-$C_2$haloalkoxy.

(23) $R_8$ is methoxy; and
$R_7$ is a 4-, 5-, or 6-membered nitrogen-linked heterocycloalkyl, which has 0 or 1 additional N, S, or O atoms, which 4-, 5-, or 6-membered nitrogen-linked heterocycloalkyl is substituted with 0 to 2 substituents independently chosen from (a) and 0 or 1 substituent (b), wherein (a) and (b) carry the definitions set forth above.

(24) $R_8$ is methoxy; and
$R_7$ is a pyrrolidinyl, piperidinyl, piperazinyl, morpholinyl, thiomorpholinyl, or azepanyl group substituted with substituted with 0 to 2 substituents independently chosen from or more of (a) and 0 or 1 substituents (b), wherein (a) and (b) carry the definitions set forth above.

(25) $R_8$ is methoxy; and
$R_7$ is a piperazinyl or thiomorpholinyl group, each of which is substituted with 0 to 2 substituents independently chosen from or more of (a) and 0 or 1 substituents (b); wherein (a) is chosen from halogen, hydroxy, amino, $C_1$-$C_2$alkyl, $C_1$-$C_2$alkoxy, $C_1$-$C_2$haloalkyl, and $C_1$-$C_2$haloalkoxy, and (b) is oxo, amino, cyano, hydroxy$C_1$-$C_4$alkyl, amino$C_1$-$C_4$alkyl, $C_2$-$C_4$alkanoyl (mono- and di-$C_1$-$C_4$alkyl)amino$C_0$-$C_4$alkyl, ($C_3$-$C_7$cycloalkyl)$C_0$-$C_4$alkyl substituted with amino, ($C_3$-$C_7$cycloalkylamino)$C_0$-$C_4$alkyl, or ($C_3$-$C_7$cycloalkyl)($C_1$-$C_4$alkyl)amino$C_0$-$C_4$alkyl.

(26) $R_8$ is methoxy; and
$R_7$ is a pyrrolidinyl group, which is substituted with 0 to 2 substituents independently chosen from or more of (a) and 0 or 1 substituents (b), wherein (a) and (b) may carry any of the definitions set forth above for these variables.

(27) $R_8$ is methoxy; and
$R_7$ is pyrrolidinyl group substituted with one group (b) and optionally substituted with 1 methyl or halogen substituent wherein (b) is oxo, amino, cyano, hydroxy$C_1$-$C_4$alkyl, amino$C_1$-$C_4$alkyl, $C_2$-$C_4$alkanoyl (mono- and di-$C_1$-$C_4$alkyl)amino$C_0$-$C_4$alkyl, ($C_3$-$C_7$cycloalkyl)$C_0$-$C_2$alkyl substituted with amino, ($C_3$-$C_7$cycloalkylamino)$C_0$-$C_4$alkyl, or ($C_3$-$C_7$cycloalkyl)($C_1$-$C_4$alkyl)amino$C_0$-$C_4$alkyl.

(28) $R_8$ is methoxy and
$R_7$ is

Wherein $R_{15}$ is (b); and $R_{16}$ is 0 or 1 or more substituents chosen from amino, hydroxy, chloro, fluoro, methyl, methoxy, trifluoromethyl, and trifluoromethoxy; (b) may carry any of the definitions set forth above for these variables.

(29) Certain compounds that meet the requirements of (28) above, $R_{15}$ is oxo, amino, cyano, hydroxy$C_1$-$C_4$alkyl, amino$C_1$-$C_4$alkyl, $C_2$-$C_4$alkanoyl, (mono- and di-$C_1$-$C_4$alkylamino)$C_0$-$C_4$alkyl, ($C_3$-$C_7$cycloalkyl)$C_0$-$C_2$alkyl substituted with amino, ($C_3$-$C_7$cycloalkylamino)$C_0$-$C_4$alkyl, or ($C_3$-$C_7$cycloalkyl)($C_1$-$C_4$alkyl)amino$C_0$-$C_4$alkyl. In certain of these compounds $R_{15}$ is oxo, cyano, hydroxy$C_1$-$C_4$alkyl, amino$C_1$-$C_4$alkyl, acetyl, (mono- and di-$C_1$-$C_2$alkylamino)$C_1$-$C_4$alkyl, cyclopropyl substituted with amino, or ($C_3$-$C_7$cycloalkylamino)$C_0$-$C_4$alkyl; and $R_{16}$ is 0 or 1 substituent chosen from hydroxy, amino, chloro, and methyl.

(30) $R_7$ is a group of the formula

-continued

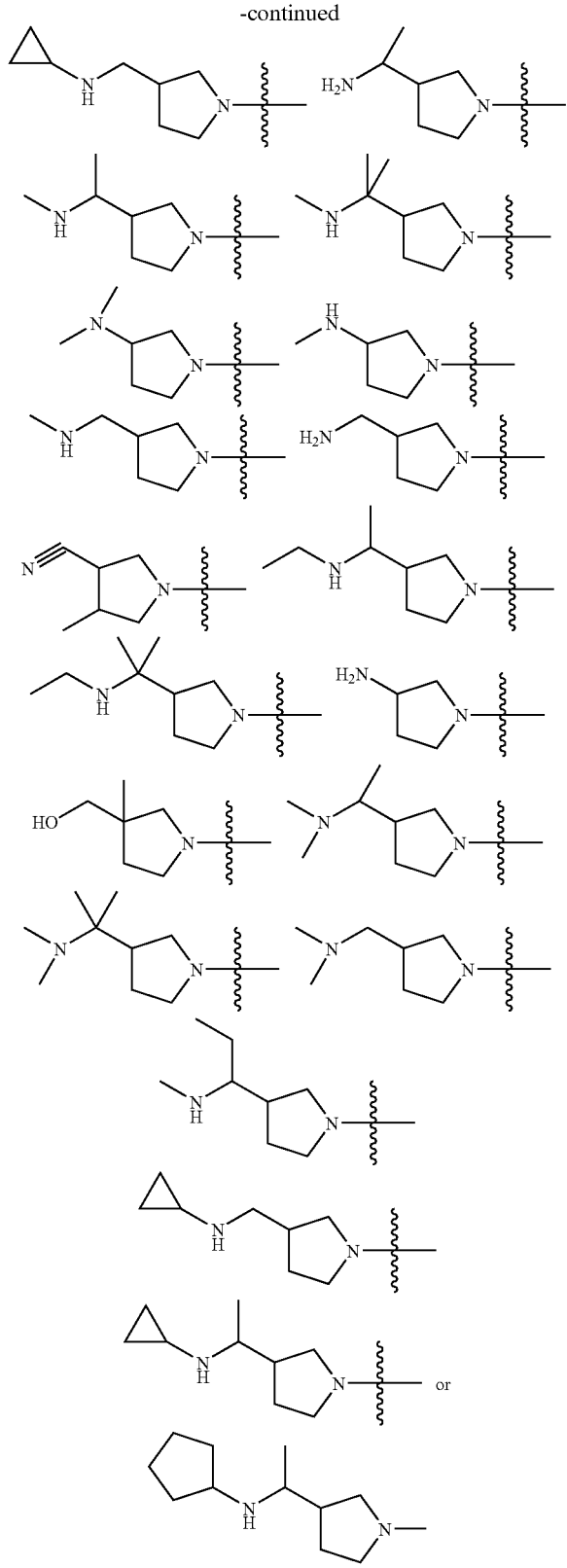

(31) R$_8$ is methoxy; and

R$_7$ is a nitrogen-linked C$_1$-C$_4$alkylamino substituted with a 5 or 6-membered heteroaryl group having 1 or 2 heteroatoms independently chosen from N, O, and S, or substituted with a heterocycloalkyl group, which has 4 to 8 ring members, including 1 or 2 ring heteroatoms independently chosen from N, O, and S;

Each of which R$_7$ is substituted with 0 or 1 or more substituents independently chosen from (a) and 0 or 1 substituents chosen from (b), wherein (a) and (b) may carry any of the definitions set forth above for these variables.

(32) R$_8$ is methoxy; and

R$_7$ is a nitrogen-linked C$_1$-C$_4$alkylamino substituted with a 5 or 6-membered heteroaryl group having 1 or 2 heteroatoms independently chosen from N, O, and S, or substituted with a heterocycloalkyl group, which has 4 to 8 ring members, including 1 or 2 ring heteroatoms independently chosen from N, O, and S; each of which heteroaryl or heterocycloalkyl is substituted with 0, 1, or 2 substituents independently chosen from halogen, hydroxy, amino, oxo, cyano, C$_1$-C$_2$alkyl, C$_1$-C$_2$alkoxy, C$_1$-C$_2$haloalkyl, and C$_1$-C$_2$haloalkoxy.

(33) R$_8$ is methoxy, and R$_7$ is C$_1$-C$_4$alkylamino substituted with a pyridyl, pyrimidinyl, piperazinyl, piperidinyl, or morpholinyl, each of which is substituted with 0, 1, or 2 substituents independently chosen from halogen, hydroxy, amino, oxo, cyano, C$_1$-C$_2$alkyl, C$_1$-C$_2$alkoxy, C$_1$-C$_2$haloalkyl, and C$_1$-C$_2$haloalkoxy.

(34) R$_8$ is methoxy; and

R$_7$ is a nitrogen-linked heterocycloalkyl or heterocycloalkenyl group, each of which has 4 to 8 ring members, including 0, 1, or 2 additional ring heteroatoms independently chosen from N, O, and S, forming part of a bicyclic system with a 3- to 8-membered cycloalkyl or heterocycloalkyl ring in fused or spiro orientation.

Each of which R$_7$ is substituted with 0 or 1 or more substituents independently chosen from (a) and 0 or 1 substituents chosen from (b), wherein (a) and (b) carry any of the definitions set forth above for these variables.

(35) R$_8$ is methoxy, and R$_7$ is a piperidinyl, piperazinyl, or pyrrolidinyl group, which is part of a bicyclic system having a spiro attached C$_3$-C$_4$cycloalkyl, dioxolanyl, or azetidinyl group, which bicyclic system is substituted with 0, 1, or 2 substituents independently chosen from halogen, hydroxy, amino, oxo, cyano, C$_1$-C$_2$alkyl, C$_1$-C$_2$alkoxy, C$_1$-C$_2$haloalkyl, and C$_1$-C$_2$haloalkoxy.

(36) R$_8$ is methoxy, and R$_7$ is a 5- or 6-membered nitrogen-linked heterocycloalkyl, which has 0 or 1 additional nitrogen atoms, which 5- or 6-membered nitrogen-linked heterocycloalkyl is part of a bicyclic ring system having a fused C$_3$-C$_6$cycloalkyl or a fused 4- to 6-membered heterocycloalkyl containing 1 nitrogen atom, which bicyclic ring system is substituted with 0, 1, or 2 substituents independently chosen from independently chosen from halogen, hydroxy, amino, oxo, cyano, C$_1$-C$_2$alkyl, C$_1$-C$_2$alkoxy, C$_1$-C$_2$haloalkyl, and C$_1$-C$_2$haloalkoxy.

(37) R$_7$ is octahydropyrrolo[3,4-b]pyridin-6-yl ring system which is substituted with 0, 1, or 2 substituents independently chosen from halogen, methyl, or methoxy.

(38) R$_8$ is methoxy, and R$_7$ is a nitrogen-linked 6-membered heterocycloalkyl group, 0, 1 or 2 additional ring heteroatoms independently chosen from N, O, and S, and bridged with a methylene or ethylene bridge. Each of which R$_7$ is substituted with 0 or 1 or more substituents independently chosen from (a) and 0 or 1 substituents chosen from (b), wherein (a) and (b) may carry any of the definitions set forth above for these variables.

The A$_8$ Variable (1) A$_8$ is nitrogen.

(2) A$_8$ is CR$_8$.

(3) A$_8$ is CR$_8$, and R$_8$ is hydrogen, halogen, C$_1$-C$_2$alkyl, C$_1$-C$_2$alkoxy, C$_1$-C$_2$haloalkyl, or C$_1$-C$_2$haloalkoxy.

(4) $A_8$ is $CR_8$, and $R_8$ is hydrogen, halogen, $C_1$-$C_2$alkyl, $C_1$-$C_2$alkoxy, trifluoromethyl, or trifluoromethoxy.

(5) $A_8$ is $CR_8$, and $R_8$ is hydrogen, halogen, or $C_1$-$C_2$alkoxy.

(6) $A_8$ is $CR_8$ and $R_8$ is hydrogen or methoxy.

(7) $A_8$ is $CR_8$ and $R_8$ is methoxy.

(8) $R_6$ is fluoro and $R_8$ is methoxy.

The $R_9$ Variable (1) $R_9$ is $C_1$-$C_8$alkyl, $C_1$-$C_4$alkoxy, mono- or di-($C_1$-$C_4$alkyl)amino, $C_2$-$C_4$alkanoyl, $C_1$-$C_2$haloalkyl, $C_1$-$C_2$haloalkoxy, ($C_3$-$C_7$cycloalkyl)$C_0$-$C_4$alkyl, or phenyl, each of which is substituted with 0 to 3 substituents independently chosen from halogen, hydroxy, amino, $C_1$-$C_2$alkyl, $C_1$-$C_2$alkoxy, mono- and di-($C_1$-$C_2$)alkylamino, $C_1$-$C_2$haloalkyl, and $C_1$-$C_2$haloalkoxy.

(2) $R_9$ is $C_1$-$C_4$alkyl, cyclopropyl, or phenyl, each of which is substituted with 0 to 3 substituents independently chosen from halogen, hydroxy, amino, $C_1$-$C_2$alkyl, $C_1$-$C_2$alkoxy, mono- and di-($C_1$-$C_2$)alkylamino, $C_1$-$C_2$haloalkyl, and $C_1$-$C_2$haloalkoxy.

(3) $R_9$ is $C_1$-$C_4$alkyl or cyclopropyl, or (4) $R_9$ is phenyl substituted with 2 substituents chosen from halogen, hydroxy, amino, $C_1$-$C_2$alkyl, $C_1$-$C_2$alkoxy, mono- and di-($C_1$-$C_2$)alkylamino, $C_1$-$C_2$haloalkyl, and $C_1$-$C_2$haloalkoxy.

(4) $R_9$ is ethyl, t-butyl, cyclopropyl, or 2,4-difluorophenyl.

(5) $R_9$ is cyclopropyl.

Any of the above conditions may be combined, so long as a stable compounds of Formula I (or a tautomer or subformula thereof) results. For example the invention includes compounds of Formula III (a subformula of Formula I), in which condition (3) for the $R_5$ variable is met, condition (2) for the $R_6$ variable is met, condition (8) for the $R_7$ variable is met, condition (7) for the $A_8$ variable is met, and condition (4) for the $R_9$ variable is met, i.e. the invention includes compounds of Formula III

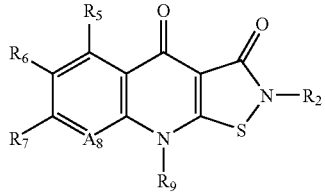

Formula III and pharmaceutically acceptable salts thereof in which the variable $R_5$ to $R_9$ carry the definitions which follow.

$R_5$ is hydrogen (3).

$R_6$ is fluoro or hydrogen (2).

$R_7$ is a group of formula (a)-(e)

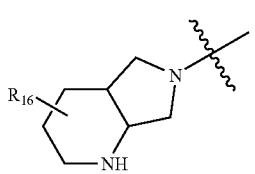

(a)

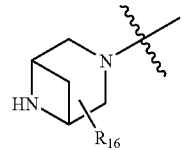

(b)

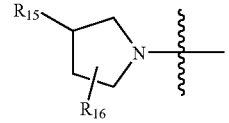

(c)

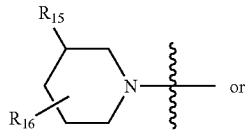

(d)

or

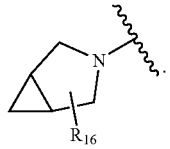

(e)

Wherein:

$R_{15}$ is oxo or cyano; or $R_{15}$ is $C_3$-$C_7$cycloalkyl substituted with 0 or 1 $C_1$-$C_2$alkyl or amino substituents, or $R_{15}$ is $C_3$-$C_6$ alkyl or mono- or di-($C_1$-$C_4$alkyl)amino$C_1$-$C_4$alkyl, each of which is substituted with 0, 1, or 2 substituents independently chosen from amino, hydroxy, ($C_3$-$C_7$cycloalkyl)$C_0$-$C_2$alkyl, ($C_3$-$C_7$cycloalkyl)$C_0$-$C_2$alkylamino, and (heterocycloalkyl)$C_0$-$C_2$alkylamino; or $R_{15}$ is mono- or di-($C_3$-$C_6$alkyl)($C_0$-$C_4$alkyl)amino, or $R_{15}$ is =$NR_{10}$ or —($C_0$-$C_4$alkyl)(C=O)$R_{10}$, or —($C_0$-$C_4$alkyl)$NCH_3$(C=O)$OR_{11}$, where each $R_{10}$ and $R_{11}$ are hydrogen or $C_1$-$C_4$alkyl.

$R_{16}$ is 0 or 1 or more substituents independently chosen from chloro, fluoro, methyl, methoxy, aminomethyl, aminoethyl, trifluoromethyl, and trifluoromethoxy (8).

$A_8$ is $CR_8$ and $R_8$ is methoxy (7); and $R_9$ is ethyl, t-butyl, cyclopropyl, or 2,4-difluorophenyl (4).

Certain compounds of Formula I and Formula II possess potent antibacterial, antifungal, and/or antiprotozoal activity. Particular compounds of the invention exhibit Minimum Inhibitory Concentrations (MIC) of 64 µg/ml or less against *Staphylococcus aureus* and/or *Eschericia coli* in a standard assay for determining the MIC of a compound against these bacteria, such as the assay provided in Example 9 below. Preferred compounds of the Formula I and II exhibit MIC values of 10 µg/ml or less against *Staphylococcus aureus* and/or *Eschericia coli*. More preferred compound of the Formula I and II exhibit MIC values of 4 µg/ml or less, or even more preferably 1 µg/ml or less, against *Staphylococcus aureus* and/or *Eschericia coli*.

Certain compounds of Formula I and Formula II are selective antimicrobial agents; having the ability to kill or inhibit the growth or reproduction of microbial organisms, while having little or no effect on the cells of fish, amphibians, reptiles, birds, or mammals. The selectivity of compounds of Formula I and Formula II may be assessed by determining the $CC_{50}$ (the concentration at which 50% of the cells are killed) for cultured cells of a higher animal, such as a fish, reptiles, amphibian, bird, or mammal. Certain compounds of the invention exhibit a $CC_{50}$ of greater that 100 micromolar for mammalian cells. Certain compounds of the invention exhibit a $CC_{50}$ of greater than 100 micromolar for cultured human hepatocytes, and also exhibit MIC values of 64 µg/ml or less, preferably 10 µg/ml or less, or more preferably 4 µg/ml or less, or still more preferably 1 µg/ml or less against *Staphylococcus aureus* and/or *Eschericia coli*.

Without wishing to be bound to any particular theory it is believed that the antimicrobial properties of compounds of Formula I and Formula II are due to the ability to these compounds to inhibit the activity of microbial DNA gyrases while having little or no effect on the analogous enzyme, topoisomerase II, present in higher organisms. Certain preferred compound of the invention are 100-fold or more selective for bacterial DNA gyrases than for mammalian, particularly human, topoisomerase II.

Compounds with Increased Therapeutic Range

It has been unexpectedly discovered that substitution of compounds of Formula I and Formula II with a methoxy substituent at the $R_8$ position increases the anti-microbial activity of the compound against Methicillin resistant *Staphylococcus Aureus* bacteria while at the same time decreasing the cellular toxicity of the compound. The simultaneous increase in compound activity and decrease in compound toxicity provides a greater therapeutic range for compounds of Formula I and Formula II in which $R_8$ is methoxy; i.e. the range of doses of such compounds that will produce beneficial effects without harmful side effects is increased. Anti-microbial activity is determined using a standard assay for determining the MIC of a compound against a methicillin resistant strain of *Staphylococcus Aureus* bacteria, such as the assay provided in Example 9 below. Therapeutic range is determined using a standard assay of cytotoxicity such as the Alamar blue assay provided in Example 10.

Table I provides a comparison of anti-microbial activity and cellular toxicity of a number of compounds described herein without and with a methoxy substituent at the $R_8$ position.

TABLE I

| $R_7$ Structure | | $R_6 = F, R_8 = H$ | | | $R_6 = F, R_8 = $ Methoxy | | | Fold Improvement with $R_8 = $ Methoxy | | |
|---|---|---|---|---|---|---|---|---|---|---|
| | Cmp # | MRSA MIC | hep2 $CC_{50}$ | $CC_{50}$/MIC | Cmp # | MRSA MIC | hep2 $CC_{50}$ | $CC_{50}$/MIC | MIC | $CC_{50}$ | $CC_{50}$/MIC |
| (piperazine) | A[1] | 3.3 | 6.6 | 2.0 | 38 | 4.8 | 27 | 7.1 | 0.87 | 4.1 | 3.6 |
| (octahydropyrrolopyridine) | 46 | 4 | 4.7 | 1.2 | 45 | 2 | 93 | 46.5 | 2.00 | 19.8 | 39.6 |
| (methylamino-pyrrolidine) | 114 | 2 | 3 | 1.5 | 49 | 4 | 68 | 17.0 | 0.50 | 22.7 | 11.3 |
| (aminomethyl-pyrrolidine) | 52 | 0.38 | 0.55 | 1.4 | 53 | 0.1 | 8.5 | 85.0 | 3.80 | 15.5 | 58.7 |
| (aminomethyl-pyrrolidine stereoisomer) | 61 | 16 | 6.1 | 0.4 | 58 | 1.5 | 61 | 40.7 | 10.67 | 10.0 | 106.7 |
| (aminomethyl-pyrrolidine) | 64 | 1 | 3.1 | 3.1 | 63 | 0.42 | 11 | 26.2 | 2.38 | 3.5 | 8.4 |

TABLE I-continued

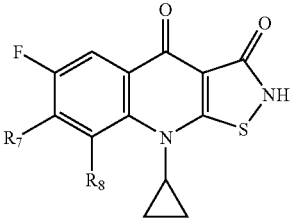

| | $R_6 = F, R_8 = H$ | | | $R_6 = F, R_8 = Methoxy$ | | | Fold Improvement with $R_8 = Methoxy$ | | |
|---|---|---|---|---|---|---|---|---|---|---|
| $R_7$ Structure | Cmp # | MRSA MIC | hep2 $CC_{50}$ | $CC_{50}/$ MIC | Cmp # | MRSA MIC | hep2 $CC_{50}$ | $CC_{50}/$ MIC | MIC | $CC_{50}$ | $CC_{50}/$ MIC |
| 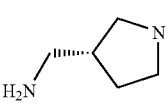 | 68 | 1 | 2.3 | 2.3 | 67 | 0.25 | 11 | 44.0 | 4.0 | 4.8 | 19.1 |
|  | 80 | 2 | 0.57 | 0.3 | 76 | 0.13 | 27 | 216.0 | 16.0 | 47.4 | 757.9 |

[1]Compound A was disclosed by Abbott in U.S. Pat. No. 5,071,848, which is hereby incorporated by reference for its teachings regarding compound A.
The MRSA strain used in this study was ATCC 700699, from ATTC, Manassas VA.
Hep2 cells are ATCC catalog number CCL-23, Manassas VA.

Anti-Microbial and Pharmaceutical Preparations

The invention provides anti-microbial compositions, including anti-bacterial compositions, comprising a compound or salt thereof of Formula I or Formula II, together with a carrier, diluent, or excipient.

In certain embodiments the invention provides pharmaceutical compositions comprising a compound or salt of salt thereof of Formula I or Formula II, together with a pharmaceutically acceptable carrier, diluent, or excipient. The pharmaceutical composition may be formulated as any pharmaceutically useful form, e.g., as an aerosol, a cream, a gel, a pill, a capsule, a tablet, a syrup, a transdermal patch, or an ophthalmic solution.

Compounds and salts of Formula I and Formula II can be administered as the neat chemical, but are preferably administered as a pharmaceutical composition or formulation. Accordingly, the invention provides pharmaceutical formulations comprising a compound or pharmaceutically acceptable salt of Formula I or Formula II, together with one or more pharmaceutically acceptable carrier, excipients, adjuvant, diluent, or other ingredient.

Compounds of general Formula I and Formula II may be administered orally, topically, parenterally, by inhalation or spray, sublingually, transdermally, via buccal administration, rectally, as an ophthalmic solution, or by other means, in dosage unit formulations containing conventional non-toxic pharmaceutically acceptable carriers, excipients, adjuvants, and vehicles.

In addition to the subject compound, the compositions of the invention may contain a pharmaceutically acceptable carrier, one or more compatible solid or liquid filler diluents or encapsulating substances, which are suitable for administration to an animal. Carriers must be of sufficiently high purity and sufficiently low toxicity to render them suitable for administration to the animal being treated. The carrier can be inert or it can possess pharmaceutical benefits of its own. The amount of carrier employed in conjunction with the compound is sufficient to provide a practical quantity of material for administration per unit dose of the compound.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, and corn oil; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

In particular, pharmaceutically acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil.

Optional active agents may be included in a pharmaceutical composition, which do not substantially interfere with the activity of the compound of the present invention.

Effective concentrations of one or more of the compounds of the invention including pharmaceutically acceptable salts, esters or other derivatives thereof are mixed with a suitable pharmaceutical carrier, excipients, adjuvant, or vehicle. In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as Tween, or dissolution in aqueous sodium bicarbonate. Derivatives of the compounds, such as salts of the compounds or prodrugs of the compounds may also be used in formulating effective pharmaceutical compositions.

Upon mixing or addition of the compound(s) of Formula I and/or Formula II, the resulting mixture may be a solution, suspension, emulsion or the like. The form of the resulting mixture depends upon a number of factors, including the intended mode of administration and the solubility of the compound in the chosen carrier or vehicle. The effective concentration sufficient for ameliorating the symptoms of the disease, disorder or condition treated and may be empirically determined.

The pharmaceutical compositions containing compounds of general Formula I and/or Formula II may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations.

Oral formulations contain between 0.1 and 99% of a compound of the invention and usually at least about 5% (weight %) of a compound of the present invention. Some embodiments contain from about 25% to about 50% or from 5% to 75% of a compound of invention.

Liquids Formulations

Compounds of the invention can be incorporated into oral liquid preparations such as aqueous or oily suspensions, solutions, emulsions, syrups, or elixirs, for example. Moreover, formulations containing these compounds can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monsoleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

Orally administered compositions also include liquid solutions, emulsions, suspensions, powders, granules, elixirs, tinctures, syrups, and the like. The pharmaceutically acceptable carriers suitable for preparation of such compositions are well known in the art. Oral formulations may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such formulations may also contain a demulcent.

Suspensions

For a suspension, typical suspending agents include methylcellulose, sodium carboxymethyl cellulose, AVICEL RC-591, tragacanth and sodium alginate; typical wetting agents include lecithin and polysorbate 80; and typical preservatives include methyl paraben and sodium benzoate.

Aqueous suspensions contain the active material(s) in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents; may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n-propyl p-hydroxybenzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Emulsions

Pharmaceutical compositions of the invention may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate.

Dispersible Powders

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets and Capsules

Tablets typically comprise conventional pharmaceutically compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules (including time release and sustained release formulations) typically comprise one or more solid diluents disclosed above. The selection of carrier components often depends on secondary considerations like taste, cost, and shelf stability.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Injectable and Parenteral Formulations

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid are useful in the preparation of injectables.

Compounds of Formula I and Formula II may be administered parenterally in a sterile medium. Parenteral administration includes subcutaneous injections, intravenous, intramuscular, intrathecal injection or infusion techniques. The drug, depending on the vehicle and concentration used, can either be suspended or dissolved in the vehicle. Advantageously, adjuvants such as local anesthetics, preservatives and buffering agents can be dissolved in the vehicle. In compositions for parenteral administration the carrier comprises at least about 90% by weight of the total composition.

Suppositories

Compounds of Formula I and Formula II may also be administered in the form of suppositories for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Topical Formulations

Compounds of the invention may be formulated for local or topical application, such as for topical application to the skin and mucous membranes, such as in the eye, in the form of gels, creams, and lotions and for application to the eye or for intracisternal or intraspinal application. Topical compositions of the present invention may be in any form including, for example, solutions, creams, ointments, gels, lotions, milks, cleansers, moisturizers, sprays, skin patches, and the like.

Such solutions may be formulated as 0.01%-10% isotonic solutions, pH about 5-7, with appropriate salts. Compounds of the invention may also be formulated for transdermal administration as a transdermal patch.

Topical compositions containing the active compound can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows:

Emollients, such as stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, isobutane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, and ethylene glycol monostearate.

The compounds of the invention may also be topically administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Other Formulations

Other compositions useful for attaining systemic delivery of the subject compounds include sublingual, buccal and nasal dosage forms. Such compositions typically comprise one or more of soluble filler substances such as sucrose, sorbitol and mannitol, and binders such as acacia, microcrystalline cellulose, carboxymethyl cellulose and hydroxypropyl methylcellulose. Glidants, lubricants, sweeteners, colorants, antioxidants and flavoring agents disclosed above may also be included.

Compositions for inhalation typically can be provided in the form of a solution, suspension or emulsion that can be administered as a dry powder or in the form of an aerosol using a conventional propellant (e.g., dichlorodifluoromethane or trichlorofluoromethane).

Additional Components

The compositions of the present invention may also optionally comprise an activity enhancer. The activity enhancer can be chosen from a wide variety of molecules that function in different ways to enhance antimicrobial effects of compounds of the present invention. Particular classes of activity enhancers include skin penetration enhancers and absorption enhancers.

Pharmaceutical compositions of the invention may also contain additional active agents can be chosen from a wide variety of molecules, which can function in different ways to enhance the antimicrobial or therapeutic effects of a compound of the present invention. These optional other active agents, when present, are typically employed in the compositions of the invention at a level ranging from about 0.01% to about 15%. Some embodiments contain from about 0.1% to about 10% by weight of the composition. Other embodiments contain from about 0.5% to about 5% by weight of the composition.

Packaged Formulations

The invention includes packaged pharmaceutical formulations. Such packaged formulations include a pharmaceutical composition containing one or more compounds or salts of Formula I or Formula II in a container and instructions for using the composition to treat an animal (typically a human patient) suffering from a microorganism infection) or prevent a microorganism infection in an animal.

The instructions may be instructions for using the compositions to treat a bacterial, *mycoplasm*, or protozoal infection. For example the instructions may be instructions for using the composition to treat a urinary or genital tract infection, such as pyelonephritis, cervical gonococcal infections, cystitis, urethral chlamydial infections, cervical chlamydial infections, urethral gonococcal infections, and prostatitis, a respiratory infection, such as lower respiratory tract infections, acute sinusitis, acute exacerbations of chronic bronchitis, community-acquired pneumonia, and nosocomial pneumonia, skin infections, such as skin-structure infections, impetigo, folliculitis, boils, scalded skin syndrome, and cellulites, and other infections such as bone infections, joint infections, infectious diarrhea, typhoid fever, intra-abdominal infections, gynecologic infections, including toxic shock syndrome, pelvic infections, and post-surgical infections. The instructions may be instructions for using the composition to treat a patient suffering from a bacterial infection, such as a *S. aureus* infection.

In all of the foregoing the compounds of the invention can be administered alone or as mixtures, and the compositions may further include additional drugs or excipients as appropriate for the indication.

Methods of Treatment

The invention includes methods of preventing and treating microorganism infections, particularly bacterial and protozoal infections, by administering an effective amount of one or more compounds of Formula I and of Formula II to an animal at risk for a microorganism infection or suffering from a microorganism infection. The animal may be a fish, amphibian, reptile or bird, but is preferably a mammal. Methods of treating and preventing microorganism infections in livestock animals, companion animals, and human patients are particularly preferred.

The compounds disclosed herein are useful for preventing and treating bacterial infections in animals. Furthermore compounds of the invention may be used to treat a variety of conditions not attributed to bacterial infections. These include diseases and disorders caused fungal infections, mycoplasma infections, protozoal infections, or other conditions involving infectious organisms.

In some circumstances an effective amount of a compound of Formula I or Formula II may be an amount sufficient to reduce the symptoms of the microorganism infection. Alternatively an effective amount of a Compound of Formula I may be an amount sufficient to significantly reduce the amount of microorganism or antibodies against the detectable in a patient's tissues or bodily fluids.

Methods of treatment also include inhibiting microorganism replication in vivo, in an animal at risk for a microorganism infection or suffering from such an infection, by administering a sufficient concentration of a compound of Formula I or Formula II to inhibit bacterial survival in vitro. By "sufficient concentration" of a compound administered to the patient is meant the concentration of the compound available in the animal's system to prevent or combat the infection. Such a concentration by be ascertained experimentally, for example by assaying blood concentration of the compound, or theoretically, by calculating bioavailability. The amount of a compound sufficient to inhibit bacterial survival in vitro may be determined with a conventional assay for bacterial survival such as the Minimum Inhibitory Concentration (MIC) Assay disclosed in Example 9, which follows.

The invention also includes using compounds of Formula I and Formula I in prophylactic therapies. In the context of prophylactic or preventative treatment an effective amount of a compound of the invention is an amount sufficient to significantly decrease the treated animal's risk of contracting a microorganism infection.

Compounds of the invention are particularly useful for treating and preventing infectious disorders. These include for example: ocular infections such as conjunctivitis; urinary tract and genital infections, such as complicated urinary tract infections, acute urinary tract and genital infections, such as pyelonephritis, cervical gonococcal infections, cystitis, urethral chlamydial infections, cervical chlamydial infections, urethral gonococcal infections, and prostatitis, respiratory infections, such as lower respiratory tract infections, acute sinusitis, acute exacerbations of chronic bronchitis, community-acquired pneumonia, and nosocomial pneumonia, skin infections, such as skin-structure infections, impetigo, folliculitis, boils, scalded skin syndrome, and cellulites, and other infections such as bone infections, joint infections, infectious diarrhea, typhoid fever, intra-abdominal infections, gynecologic infections, including toxic shock syndrome, pelvic infections, and post-surgical infections.

The disclosed compounds are useful for treating infections caused by the following microorganisms:

Aerobic Gram-positive Microorganisms: Including but not limited to *Enterococcus faecalis, Enterococcus faecium, Staphylococcus aureus* (including methicillan *S. aureus*), *Staphylococcus epidermidis, Staphylococcus saprophyticus, Streptococcus pneumoniae, Streptococcus pyogenes, Staphylococcus haemolyticus*, and *Staphylococcus hominis*.

Aerobic Gram-negative Microorganisms: Including but not limited to *Campylobacter jejuni, Citrobacter diversus, Citrobacter freundii, Enterobacter cloacae, Escherichia coli, Haemophilus influenzae, Haemophilus parainfluenzae, Klebsiella pneumoniae, Moraxella catarrhalis, Morganella morganii, Neisseria gonorrhoeae, Proteus mirabilis, Proteus vulgaris, Providencia rettgeri, Providencia stuartii, Pseudomonas aeruginosa, Stenotrophomonas maltophila, Salmonella typhi, Serratia marcescens, Shigella boydii, Shigella dysenteriae, Shigella flexneri, Shigella sonnei. Acinetobacter Iwoffi, Aeromonas hydrophila, Edwardsiella tarda, Enterobacter aerogenes, Klebsiella oxytoca, Legionella pneumophila, Pasteurella multocida, Salmonella enteritidis, Vibrio cholerae, Vibrio parahaemolyticus, Vibrio vulnificus, Yersinia enterocolitica* and *H. Pylorii*.

Non-Bacterial Microorganisms: *Mycoplasma, Legionella* and *Chlamydia*.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most infectious disorders, a dosage regimen of 4 times daily or less is preferred and a dosage regimen of 1 or 2 times daily is particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Combination Administration

The compounds of the invention may also be useful in combination with other pharmaceutically active agents such as antibacterial agents, antiviral agents, antifungal agents, anti-inflammatories, interferon, efflux-pump inhibitors, and beta-lactamase inhibitors. Antibiotic agents include any molecule that tends to prevent, inhibit or destroy life and as such, includes anti-bacterial agents, anti-fungicides, anti-viral agents, and anti-parasitic agents.

Pharmaceutical compositions of the invention include single dosage forms containing of a compound of Formula I and/or Formula II and one or more other active agent, dosage forms containing more than one compound of Formula I and/or Formula II, and separate administration of a compound of Formula I and/or Formula II with another active agent.

The following active agents, which are useful in combinations of the invention, may be isolated from an organism that produces the agent or synthesized by methods known to those of ordinary skill in the art of medicinal chemistry or purchased from a commercial source.

Anti-bacterial antibiotic agents include, but are not limited to, penicillins, cephalosporins, carbacephems, cephamycins, carbapenems, monobactams, aminoglycosides, glycopeptides, quinolones, tetracyclines, macrolides, and fluoroquinolones (see Table below). Examples of antibiotic agents include, but are not limited to, Penicillin G (CAS Registry No.: 61-33-6); Methicillin (CAS Registry No.: 61-32-5); Nafcillin (CAS Registry No.: 147-52-4); Oxacillin (CAS Registry No.: 66-79-5); Cloxacillin (CAS Registry No.: 61-72-3); Dicloxacillin (CAS Registry No.: 3116-76-5); Ampicillin (CAS Registry No.: 69-53-4); Amoxicillin (CAS Registry No.: 26787-78-0); Ticarcillin (CAS Registry No.: 34787-01-4); Carbenicillin (CAS Registry No.: 4697-36-3); Mezlocillin (CAS Registry No.: 51481-65-3); Azlocillin (CAS Registry No.: 37091-66-0); Piperacillin (CAS Registry No.: 61477-96-1); Imipenem (CAS Registry No.: 74431-23-5); Aztreonam (CAS Registry No.: 78110-38-0); Cephalothin (CAS Registry No.: 153-61-7); Cefazolin (CAS Registry No.: 25953-19-9); Cefaclor (CAS Registry No.: 70356-03-5); Cefamandole formate sodium (CAS Registry No.: 42540-40-9); Cefoxitin (CAS Registry No.: 35607-66-0); Cefuroxime (CAS Registry No.: 55268-75-2); Cefonicid (CAS Registry No.: 61270-58-4); Cefinetazole (CAS Registry No.: 56796-20-4); Cefotetan (CAS Registry No.: 69712-56-7); Cefprozil (CAS Registry No.: 92665-29-7); Loracarbef (CAS Registry No.: 121961-22-6); Cefetamet (CAS Registry No.: 65052-63-3); Cefoperazone (CAS Registry No.: 62893-19-0); Cefotaxime (CAS Registry No.: 63527-52-6); Ceftizoxime (CAS Registry No.: 68401-81-0); Ceftriaxone (CAS Registry No.: 73384-59-5); Ceftazidime (CAS Registry No.: 72558-82-8); Cefepime (CAS Registry No.: 88040-23-7); Cefixime (CAS Registry No.: 79350-37-1); Cefpodoxime (CAS Registry No.: 80210-62-4); Cefsulodin (CAS Registry No.: 62587-73-9); Fleroxacin (CAS Registry No.: 79660-72-3); Nalidixic acid (CAS Registry No.: 389-08-2); Norfloxacin (CAS Registry No.: 70458-96-7); Cipro-floxacin (CAS Registry No.: 85721-33-1); Ofloxacin (CAS Registry No.: 82419-36-1); Enoxacin (CAS Registry No.: 74011-58-8); Lomefloxacin (CAS Registry No.: 98079-51-7); Cinoxacin (CAS Registry No.: 28657-80-9); Doxycycline (CAS Registry No.: 564-25-0); Minocycline (CAS Registry No.: 10118-90-8); Tetracycline (CAS Registry No.: 60-54-8); Amikacin (CAS Registry No.: 37517-28-5); Gentamicin (CAS Registry No.: 1403-66-3); Kanamycin (CAS Registry No.: 8063-07-8); Netilmicin (CAS Registry No.: 56391-56-1); Tobramycin (CAS Registry No.: 32986-56-4); Streptomycin (CAS Registry No.: 57-92-1); Azithromycin (CAS Registry No.: 83905-01-5); Clarithromycin (CAS Registry No.: 81103-11-9); Erythromycin (CAS Registry No.: 114-07-8); Erythromycin estolate (CAS Registry No.: 3521-62-8); Erythromycin ethyl succinate (CAS Registry No.: 41342-53-4); Erythromycin glucoheptonate (CAS Registry No.: 23067-13-2); Erythromycin lactobionate (CAS Registry No.: 3847-29-8); Erythromycin stearate (CAS Registry No.: 643-22-1); Vancomycin (CAS Registry No.: 1404-90-6); Teicoplanin (CAS Registry No.: 61036-64-4); Chloramphenicol (CAS Registry No.: 56-75-7); Clindamycin (CAS Registry No.: 18323-44-9); Trimethoprim (CAS Registry No.: 738-70-5); Sulfamethoxazole (CAS Registry No.: 723-46-6); Nitrofurantoin (CAS Registry No.: 67-20-9); Rifampin (CAS Registry No.: 13292-46-1); Mupirocin (CAS Registry No.: 12650-69-0); Metronidazole (CAS Registry No.: 443-48-1); Cephalexin (CAS Registry No.: 15686-71-2); Roxithromycin (CAS Registry No.: 80214-83-1); Co-amoxiclavuanate; combinations of Piperacillin and Tazobactam; and their various salts, acids, bases, and other derivatives.

Anti-fungals agents include but are not limited to Amphotericin B, Candicidin, Dermostatin, Filipin, Fungichromin, Hachimycin, Hamycin, Lucensomycin, Mepartricin, Natamycin, Nystatin, Pecilocin, Perimycin, Azaserine, Griseofulvin, Oligomycins, Neomycin, Pyrrolnitrin, Siccanin, Tubercidin, Viridin, Butenafine, Naftifine, Terbinafine, Bifonazole, Butoconazole, Chlordantoin, Chlormidazole, Cloconazole, Clotrimazole, Econazole, Enilconazole, Fenticonazole, Flutrimazole, Isoconazole, Ketoconazole, Lanoconazole, Miconazole, Omoconazole, Oxiconazole, Sertaconazole, Sulconazole, Tioconazole, Tolciclate, Tolindate, Tolnaftate, Fluconawle, Itraconazole, Saperconazole, Terconazole, Acrisorcin, Amorolfine, Biphenamine, Bromosalicylchloranilide, Buclosamide, Calcium Propionate, Chlorphenesin, Ciclopirox, Cloxyquin, Coparaffinate, Diamthazole, Exalamide, Flucytosine, Halethazole, Hexetidine, Loflucarban, Nifuratel, Potassium Iodide, Propionic Acid, Pyrithione, Salicylanilide, Sodium Propionate, Sulbentine, Tenonitrozole, Triacetin, Ujothion, Undecylenic Acid, and Zinc Propionate.

Antiviral agents include, but are not limited to, Acyclovir, Cidofovir, Cytarabine, Dideoxyadenosine, Didanosine, Edoxudine, Famciclovir, Floxuridine, Ganciclovir, Idoxuridine, Inosine Pranobex, Lamivudine, MADU, Penciclovir, Sorivudine, Stavudine, Trifluridine, Valacyclovir, Vidarabine, Zalcitabine, Zidovudine, Acemannan, Acetylleucine, Amantadine, Amidinomycin, Delavirdine, Foscarnet, Indinavir, Interferon-α, Interferon-β, Interferon-γ, Kethoxal, Lysozyme, Methisazone, Moroxydine, Nevirapine, Podophyllotoxin, Ribavirin, Rimantadine, Ritonavir2, Saquinavir, Stailimycin, Statolon, Tromantadine, and Xenazoic Acid.

Antiinflammatory agents include, but are not limited to, Enfenamic Acid, Etofenamate, Flufenamic Acid, Isonixin, Meclofenamic Acid, Mefenamic Acid, Niflumic Acid, Talniflumate, Terofenamate, Tolfenamic Acid, Aceclofenac, Acemetacin, Alclofenac, Amfenac, Amtolmetin Guacil, Bromfenac, Bufexamac, Cinmetacin, Clopirac, Diclofenac, Etodolac, Felbinac, Fenclozic Acid, Fentiazac, Glucametacin, Ibufenac, Indomethacin, Isofezolac, Isoxepac, Lonazolac, Metiazinic Acid, Mofezolac, Oxametacine, Pirazolac, Proglumetacin, Sulindac, Tiaramide, Tolmetin, Tropesin, Zomepirac, Bumadizon, Butibufen, Fenbufen, Xenbucin, Clidanac, Ketorolac, Tinoridine, Alminoprofen, Benoxaprofen, Bermoprofen, Bucloxic Acid, Carprofen, Fenoprofen, Flunoxaprofen, Flurbiprofen, Ibuprofen, Ibuproxam, Indoprofen, Ketoprofen, Loxoprofen, Naproxen, Oxaprozin, Piketoprofen, Pirprofen, Pranoprofen, Protizinic Acid, Suprofen, Tiaprofenic Acid, Ximoprofen, Zaltoprofen, Difenamizole, Epirizole, Apazone, Benzpiperylon, Feprazone, Mofebutazone, Morazone, Oxyphenbutazone, Phenylbutazone, Pipebuzone, Propyphenazone, Ramifenazone, Suxibuzone, Thiazolinobutazone, Acetaminosalol, Aspirin, Benorylate, Bromosaligenin, Calcium Acetylsalicylate, Diflunisal, Etersalate, Fendosal, Gentisic Acid, Glycol Salicylate, Imidazole Salicylate, Lysine Acetylsalicylate, Mesalamine, Morpholine Salicylate, I-Naphthyl Salicylate, Olsalazine, Parsalmide, Phenyl Acetylsalicylate, Phenyl Salicylate, Salacetamide, Salicylamide O-Acetic Acid, Salicylsulfuric Acid, Salsalate, Sulfasalazine, Ampiroxicam, Droxicam, Isoxicam, Lomoxicam, Piroxicam, Tenoxicam, epsilon-Acetamidocaproic Acid, S-Adenosylmethionine, 3-Amino-4-hydroxybutyric Acid, Amixetrine, Bendazac, Benzydamine, alpha-Bisabolol, Bucolome, Difenpiramide, Ditazol, Emorfazone, Fepradinol, Guaiazulene, Nabumetone, Nimesulide, Oxaceprol, Paranyline, Perisoxal, Proquazone, Superoxide Dismutase, Tenidap, Zileuton, 21-Acetoxypregnenolone, Alclometasone, Algestone, Amcinonide, Beclomethasone, Betamethasone, Budesonide, Chloroprednisone, Clobetasol, Clobetasone, Clocortolone, Cloprednol, Corticosterone, Cortisone, Cortivazol, Deflazacort, Desonide, Desoximetasone, Dexamethasone, Diflorasone, Diflucortolone, Difluprednate, Enoxolone, Fluazacort, Flucloronide, Flumethasone, Flunisolide, Fluocinolone Acetonide, Fluocinonide, Fluocortin Butyl, Fluocortolone, Fluorometholone, Fluperolone Acetate, Fluprednidene Acetate, Fluprednisolone, Flurandrenolide, Fluticasone Propionate, Formocortal, Halcinonide, Halobetasol Propionate, Halometasone, Halopredone Acetale, Hydrocortamate, Hydrocortisone, Loteprednol Etabonale, Mazipredone, Medrysone, Meprednisone, Methylprednisolone, Mometasone Furoate, Paramethasone, Prednicarbate, Prednisolone, Prednisolone 25-Diethylaminoacetate, Prednisolone Sodium Phosphate, Prednisone, Prednival, Prednylidene, Rimexolone, Tixocortol, Triamcinolone, Triamcinolone Acetonide, Triamcinolone Benetonide, and Triamcinolone Hexacetonide.

Compounds of the invention may be combined with one or more Beta lactamase inhibitor when used in combination with a beta-lactam class antibiotic, such as penicillin or cephalosporins. Beta-lactamase inhibitors include, but are not limited to Clavulanic acid, Sulbactam, Sultamacillin, and Tazobactam.

Compounds of the invention may also be combined with one or more efflux pump inhibitor, such as a quinazolinone efflux pump inhibitors, d-ornithine-d-homophenylalanine-3-aminoquinoline, Phe-Arg-b-naphthylamide, propafenone, a phenothiazine or thioxanthene efflux pump inhibitor, 1-aza-9-oxafluorenes, N-[4-[2-(3,4-dihydro-6,7-dimethoxy-2(1H)-isoquinolinyl)ethyl]phenyl]-9,10-dihydro-5-methoxy-9-oxo-4-Acridinecarboxamide, reserpine, Milbemycin, Cinchonine, Verapamil, L-phenylalanyl-N-2-naphthalenyl-L-Argininamide (and analogs), 5'-methoxyhydnocarpin-D, methylxanthines, FK506, a cyclosporine efflux pump inhibitor, Nocardamine and other siderophores, Amiodarone, Cyclosporin A, Rol 1-2933 (DMDP), Quinidine, and the optical isomers of Propranolol, Quinine (SQ1) and Quinidine, Quinine-10,11-epoxide, Quercetin, Amitriptyline, Taxuspine C derivatives, Emodin, MC-002434; Agosterol A; Pheophorbide; pyridoquinolines such as 2,2'-[(2,8,10-trimethylpyrido[3,2-g]quinoline-4,6-diyl)bis(oxy)]bis[N,N-dimethyl-ethanamine, Gitonavir, and Gemfibrozil.

Synthesis of Compounds

The compounds of the invention are prepared according to methods well-known to those skilled in the art of organic chemical synthesis. The starting materials used in preparing the compounds of the invention are known, made by known methods, or are commercially available.

It is recognized that the skilled artisan in the art of organic chemistry can readily carry out standard manipulations of organic compounds without further direction.

The skilled artisan will readily appreciate that certain reactions are best carried out when other functionalities are masked or protected in the compound, thus increasing the yield of the reaction and/or avoiding any undesirable side reactions. Often, the skilled artisan utilizes protecting groups to accomplish such increased yields or to avoid the undesired reactions. These reactions are found in the literature and are also well within the scope of the skilled artisan.

The compounds of the invention may have one or more chiral center. As a result, one may selectively prepare one optical isomer, including diastereomers and enantiomers, over another, for example by chiral starting materials, catalysts or solvents, or may prepare both stereoisomers or both optical isomers, including diastereomers and enantiomers at once (a racemic mixture). Since the compounds of the invention may exist as racemic mixtures, mixtures of optical isomers, including diastereomers and enantiomers, or stereoisomers may be separated using known methods, such as through the use of, for example, chiral salts and chiral chromatography.

In addition, it is recognized that one optical isomer, including a diastereomer and enantiomer, or a stereoisomer, may have favorable properties over the other. When a racemic mixture is discussed herein, it is clearly contemplated to include both optical isomers, including diastereomers and enantiomers, or one stereoisomer substantially free of the other.

The invention also includes also includes all energetically accessible conformational and torsional isomers of the compounds disclosed.

This invention is further illustrated by the following examples that should not be construed as limiting. The contents of all references, patents and published patent applications cited throughout this application are incorporated herein by reference.

EXAMPLES

Abbreviations

The following abbreviations are used in the reaction schemes and synthetic examples, which follow. This list in not meant to be an all-inclusive list of abbreviations used in the application as additional standard abbreviations, which are readily understood by those skilled in the art of organic synthesis, may also be used in the synthetic schemes and examples.

(Boc)₂O— Di-t-butyl dicarbonate
Cbz-Cl—Benzyloxycarbonyl chloride
m-CPBA–m-Chloroperoxybenzoic acid
DMF—N,N-Dimethylformamide
DMSO—Dimethylsulfoxide
Et₃N—Triethyl amine
Et₂O—Diethyl ether
EtOH—ethanol
EtOAc—Ethyl acetate
LDA
PPh₃—Triphenyl phosphate
PTLC—Preparative thin layer chromatography
t-BuOK—tert-Butyl oxide
TsCl—Tosyl chloride
TFA trifluoroacetic acid
THF—Tetrahydrofuran General Methods All nonaqueous reactions are performed under an atmosphere of dry argon gas (99.99%) using oven- or flame-dried glassware. Microwave-assisted syntheses are conducted in a commercial microwave reactor (Discover System, CEM Corporation). The progress of reactions is monitored using thin-layer chromatography (TLC) on glass plates coated with Merck silica gel 60 ($F_{254}$). Flash column chromatography is performed on Merck silica gel 60 (230-400 mesh). NMR spectra are recorded at ambient temperature using a Bruker Avance 300 spectrometer ($^1$H at 300.1 MHz, $^{13}$C at 75.5 MHz, and $^{19}$F at 282.4 MHz). The chemical shifts for $^1$H and $^{13}$C are reported in parts per million (δ) relative to external tetramethylsilane and are referenced to signals of residual protons in the deuterated solvent. The chemical shifts for $^{19}$F are reported in parts per million (δ) relative to external fluorotrichloromethane. Assignment of NMR data is based on two-dimensional correlation experiments ($^1$H-$^1$H COSY, $^1$H-$^{13}$C HMQC, $^1$H-$^{13}$C HMBC, and $^1$H-$^1$H NOESY) and the usual principles of NMR spectroscopy (the magnitudes of coupling constants and chemical shifts). Analytical HPLC is performed using a YMC Pack Pro C18 50×4.6 mm 5 μm column with an isocratic elution of 0.24 min at 90:10H₂O:CH₃CN containing 0.1% TFA followed by a 4-min linear gradient elution from 90:10 to 10:90 at a flow rate of 2.5 mL/min with UV detection at 254 nm. Unless noted otherwise, preparative HPLC is performed using a YMC Pack Pro C18 150×20.0 mm 5 μm column with an isocratic elution of 0.24 min at 97:3H₂O:CH₃CN containing 0.1% TFA followed by a 10-min linear gradient elution from 97:3 to 0:100 at a flow rate of 18.0 mL/min with UV detection at 254 nm. Low-resolution mass spectra are recorded on a Thermo Finnigan Surveyor MSQ instrument (operating in APCI mode) equipped with a Gilson liquid chromatograph. Unless noted otherwise, the quasi-molecular ions, [M+H]⁺, observed in the low-resolution mass spectra are the base peaks. Elemental analyses are performed at Atlantic Microlab, Inc. (Norcross, Ga.).

Example 1

Preparation of 8-Methoxy-Substituted-9H-isothiazolo[5,4-b]quinoline-3,4-diones 8-methoxy-substituted 9H-isothiazolo[5,4-b]quinoline-3,4-diones are prepared from the corresponding core intermediates (1-4) in accordance with the synthetic scheme outlined below.

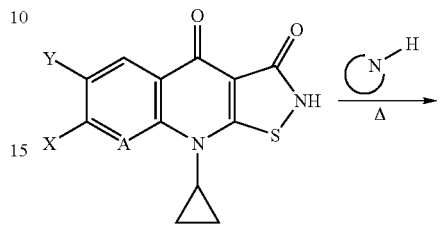

1. Y = F, X = Cl, A = N
2. Y = F, X = F, A = CH
3. Y = F, X = F, A = COMe
4. Y = H, X = F, A = COMe

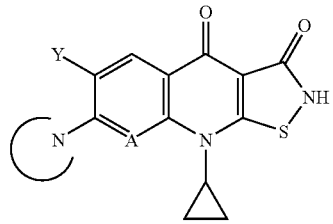

Example 2

Synthesis of Compounds of Formulas 1 and 2

7-Chloro-9-cyclopropyl-6-fluoro-9H-1-thia-2,8,9-triaza-cyclopenta[b]naphthalene-3,4-dione (1) is prepared from ethyl 2,6-dichloro-5-fluoronicotinylacetate using the procedure of Chu and Claiborne (Chu, D. T. W.; Claiborne, A. K. *J. Heterocycl. Chem.* 1990, 27, 1191-1195). 9-Cyclopropyl-6,7-difluoro-9H-isothiazolo[5,4-b]quinoline-3,4-dione (2) is prepared from 2,4,5-trifluorobenzoic acid using the procedure of Chu (Chu, D. T. W. *J. Heterocycl. Chem.* 1990, 27, 839-843).

Example 3

Synthesis of 9-Cyclopropyl-6,7-difluoro-8-methoxy-9H-isothiazolo[5,4-b]quinoline-3,4-dione (Compound 3)

9-Cyclopropyl-6,7-difluoro-8-methoxy-9H-isothiazolo[5,4-b]quinoline-3,4-dione (3) is prepared in accordance with the synthetic scheme below.

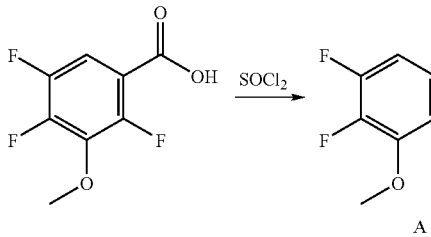

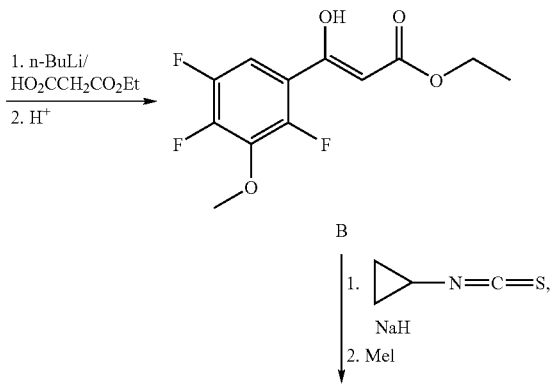

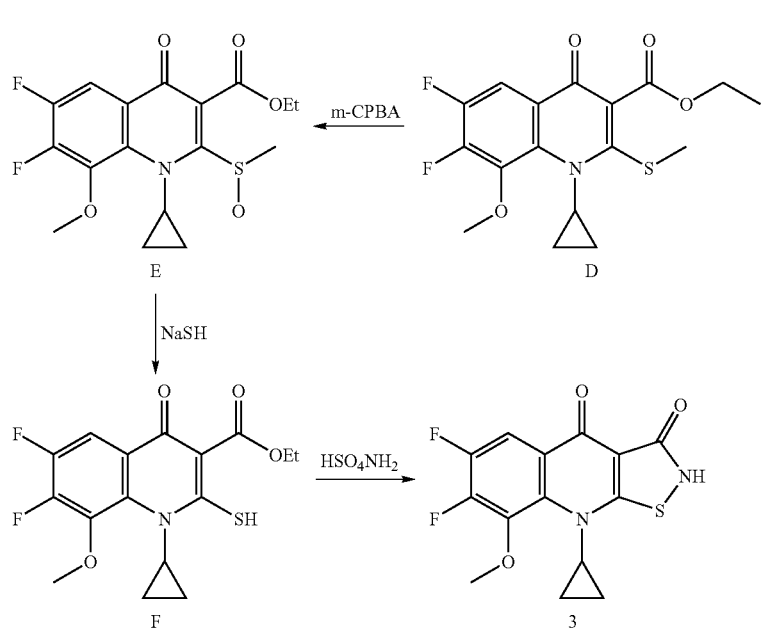
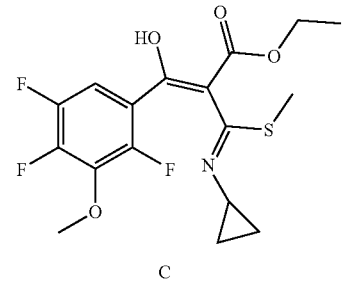

Step 1. Synthesis of 2,4,5-trifluoro-3-methoxybenzoyl chloride (A)

A mixture of 2,4,5-trifluoro-3-methoxybenzoic acid (154 mg, 0.75 mmol) and thionyl chloride (8 mL) is refluxed for 4 h. Excess thionyl chloride is removed in vacuo, and the remaining residue is used directly in the next synthetic step.

Step 2. Synthesis of (Z)-ethyl 3-hydroxy-3-(2,4,5-trifluoro-3-methoxyphenyl)acrylate (B)

Compound B is prepared using the general method of Wierenga and Skulnick (Wierenga, W.; Skulnick, H. I. *J. Org. Chem.* (1979) 44: 310-311). n-Butyllithium (1.6 M in hexanes) is added to a cooled (−78° C.) solution of tetrahydrofuran (10 mL) containing ethyl hydrogen malonate (180 µL, 1.50 mmol) and 2,2'-bipyridyl (~1 mg as indicator). The temperature of the reaction mixture is allowed to rise to ca. −5° C. during the addition of n-butyllithium. Sufficient n-butyllithium (2.8 mL, 4.48 mmol) is added until a pink color persists at −5° C. for 5-10 min. A solution of 2,4,5-trifluoro-3-methoxybenzoyl chloride (0.75 mmol, vide supra) in tetrahydrofuran (~3 mL) is added in one portion to the reaction mixture that had been recooled to −78° C. The resulting mixture is allowed to warm to room temperature, diluted with ethyl acetate (50 mL), and quenched with a 1 M aqueous solution of hydrochloric acid. The organic layer is washed with a 5% aqueous solution of sodium bicarbonate (2×30 mL), followed by brine (2×50 mL), dried over sodium sulfate, and evaporated under reduced pressure to give the crude product. This material is purified by flash column chromatography (eluting with 20% v/v ethyl acetate in hexanes) to give pure B as a white solid. $^1$H NMR (300 MHz, CDCl$_3$): (enol, predominant tautomer, ≧90%) δ 1.32 (t, $J_{H-H}$=7.0 Hz, 3H, CO$_2$CH$_2$CH$_3$), 4.02 (apparent t, $J_{H-F}$=1.0 Hz, 3H, OCH$_3$), 4.25 (q, $J_{H-H}$=7.0 Hz, 2H, CO$_2$CH$_2$CH$_3$), 5.79 (s, 1H, CH$_3$C(OH)=CH—CO$_2$CH$_2$CH$_3$), 7.39 (ddd, $J_{H-F}$=11.0 Hz, 8.5 Hz, 6.5 Hz, 1H, aromatic), 12.68 (s, 1H, OH). $^{19}$F{$^1$H} NMR (282 MHz, CDCl$_3$): δ −146.8 (dd, $J_{F-F}$=21.5 Hz, 10.5 Hz, 1F), −140.2 (dd, $J_{F-F}$=21.5 Hz, 13.5 Hz, 1F), −131.3 (dd, $J_{F-F}$=13.5 Hz, 10.5 Hz, 1F).

Step 3. Synthesis of (E)-ethyl 2-((Z)—N-cyclopropyl(methylthio)carbonoimidoyl)-3-hydroxy-3-(2,4,5-trifluoro-3-methoxyphenyl)acrylate (C)

Sodium hydride (60% in mineral oil, 31 mg, 0.78 mmol) is added portionwise to a cooled (0° C.) solution containing B (200 mg, 0.73 mmol), cyclopropyl isothiocyanate (120 µL, 1.2 mmol), and dimethylformamide (2 mL). The resulting mixture is allowed to warm to room temperature with stirring overnight (18 h). Methyl iodide (80 µL, 1.2 mmol) is added to the resulting solution and stirred for an additional 4 h (until TLC indicated the complete consumption of B). The reaction mixture is diluted with ethyl acetate (100 mL) and quenched by addition of a saturated aqueous solution of ammonium chloride (30 mL). The organic layer is washed with brine (4×30 mL), dried over sodium sulfate, and evaporated under reduced pressure to give the crude product. This material is purified by flash column chromatography (eluting with 40% v/v ethyl acetate in hexanes) to give C as a yellow oil. $^1$H NMR (300 MHz, CDCl$_3$): δ 50.86 (m, 2H, cyclopropyl CH$_2$), 0.97 (m, 5H), 2.52 (s, 3H, SCH$_3$), 3.00 (m, 1H, cyclopropyl CH), 3.96 (q, $J_{H-H}$=7.0 Hz, 2H, CO$_2$CH$_2$CH$_3$), 4.02 (apparent t, $J_{H-F}$=1.0 Hz, 3H, OCH$_3$), 6.96 (m, 1H, aromatic), 11.71 (s, 1H). $^{19}$F{$^1$H} NMR (282 MHz, CDCl$_3$): δ −149.9 (br, 1F), −141.4 (br, 1F), −135.7 (br, 1F).

Step 4. Synthesis of ethyl 1-cyclopropyl-6,7-difluoro-8-methoxy-2-(methylthio)-4-oxo-1,4-dihydroquinoline-3-carboxylate (D)

Sodium hydride (60% in mineral oil, 82 mg, 2.1 mmol) is added portionwise to a solution of C (760 mg, 1.95 mmol) in dimethylformamide (15 mL) at room temperature. The reaction mixture is heated at 80° C. for 3 d (until TLC indicates the complete consumption of B), cooled to room temperature, and quenched by addition of a saturated aqueous solution of ammonium chloride (10 mL). The mixture is extracted with ethyl acetate (3×50 mL). The combined organic extracts are washed with brine (4×30 mL), dried over sodium sulfate, and evaporated under reduced pressure to give crude D. This material is purified by flash column chromatography (eluting with 30% v/v ethyl acetate in hexanes) to D as a pale yellow oil. $^1$H NMR (300 MHz, CDCl$_3$): δ 0.73 (m, 2H, cyclopropyl CH$_2$), 1.19 (m, 2H, cyclopropyl CH$_2$), 1.38 (t, $J_{H-H}$=7.0 Hz, 3H, CO$_2$CH$_2$CH$_3$), 2.66 (s, 3H, SCH$_3$), 3.74 (m, 1H, cyclopropyl CH), 4.08 (d, $J_{H-F}$=2.5 Hz 3H, OCH$_3$), 4.40 (q, $J_{H-H}$=7.0 Hz, 2H, CO$_2$CH$_2$CH$_3$), 7.76 (dd, $J_{H-F}$=10.5 Hz, 8.5 Hz 1H, aromatic). $^{19}$F{$^1$H} NMR (282 MHz, CDCl$_3$): δ−146.8 (d, $J_{F-F}$=21.0 Hz, 1F), −137.7 (d, $J_{F-F}$=21.0 Hz, 1F). LCMS m/z calcd for C$_{17}$H$_{17}$F$_2$NO$_4$S 369 ([M$^+$]). found 370 ([M+H]$^+$).

Step 5. Synthesis of ethyl 1-cyclopropyl-6,7-difluoro-8-methoxy-2-(methylsulfinyl)-4-oxo-1,4-dihydroquinoline-3-carboxylate (E)

m-Chloroperoxybenzoic acid (≦77%, 34 mg, 0.15 mmol) is added in one portion to a solution of D (50 mg, 0.14 mmol) in methylene chloride (3 mL) at room temperature. The reaction mixture is stirred for 1 h, diluted with ethyl acetate (20 mL), and washed with a 5% aqueous solution of sodium bicarbonate (2×10 mL). The organic layer is dried over sodium sulfate and evaporated under reduced pressure to give the crude product. This material is purified by preparative thin-layer chromatography (eluting with 10% v/v hexanes in ethyl acetate) to give pure E as a white solid. $^1$H NMR (300 MHz, CDCl$_3$): δ 0.62 (m, 1H, cyclopropyl CH$_2$), 1.00 (m, 1H, cyclopropyl CH$_2$), 1.13 (m, 1H, cyclopropyl CH$_2$), 1.29 (m, 1H, cyclopropyl CH$_2$), 1.36 (t, $J_{H-H}$=7.5 Hz, 3H, CO$_2$CH$_2$CH$_3$), 3.22 (s, 3H, S(O)CH$_3$), 3.85 (m, 1H, cyclopropyl CH), 4.09 (d, $J_{H-F}$=2.5 Hz, 3H, OCH$_3$), 4.37 (q, $J_{H-H}$=7.5 Hz, 2H, CO$_2$CH$_2$CH$_3$), 7.75 (dd, $J_{H-F}$=10.0, 8.0 Hz, 1H, aromatic). $^{19}$F{$^1$H} NMR (282 MHz, CDCl$_3$): δ−145.2 (d, $J_{F-F}$=21.0 Hz, 1F), −136.2 (d, $J_{F-F}$=21.0 Hz, 1F). LCMS m/z calcd for C$_{17}$H$_{17}$F$_2$NO$_5$S 385 ([M$^+$]). found 386 ([M+H]$^+$).

Step 6. Synthesis of ethyl 1-cyclopropyl-6,7-difluoro-2-mercapto-8-methoxy-4-oxo-1,4-dihydroquinoline-3-carboxylate (F)

Anhydrous sodium hydrogen sulfide (Alfa Aesar, 20 mg, 0.36 mmol) is added in one portion to a solution of DMF (6 mL) containing E (93 mg, 0.24 mmol) at room temperature. The resulting solution is heated at 40° C. for 2-3 h (until TLC indicated complete consumption of E) and allowed to cool to room temperature. The reaction mixture is quenched by addition of a 5% aqueous solution of hydrochloric acid (20 mL) and extracted with ethyl acetate (2×25 mL). The combined organic extracts are washed with brine (4×25 mL), dried over sodium sulfate, and evaporated to dryness under reduced pressure to give crude F in quantitative yield. This material is used directly in the next synthetic step to prevent its oxidative degradation. LCMS m/z calcd for C$_{16}$H$_{15}$F$_2$NO$_4$S 355 ([M$^+$]). found 356 ([M+H]$^+$)

Step 7. Synthesis of 9-cyclopropyl-6,7-difluoro-8-methoxyisothiazolo[5,4-b]quinoline-3,4(2H,9H)-dione (3)

A solution of sodium bicarbonate (820 mg, 9.8 mmol) in water (14 mL) is added to a solution of F (348 mg, 0.98 mmol) in tetrahydrofuran (10 mL) at room temperature. Hydroxylamine-O-sulfonic acid (465 mg, 4.1 mmol) is added in one portion to this mixture. The reaction mixture is stirred at room temperature for ~3 h and quenched by addition of an aqueous solution of 5% hydrochloric acid (100 mL). The precipitate that formed is collected by filtration, washed with water (3×5 mL), and dried in vacuo to give 3 as a white solid. This product is of sufficient purity (≧95% by $^1$H NMR spectroscopy) to use directly in the final amine-coupling step. $^1$H NMR (300 MHz, DMSO-d$_6$): δ 1.12 (m, 4H, cyclopropyl CH$_2$), 3.85 (m, 1H, cyclopropyl CH), 4.01 (d, $J_{H-F}$=1.5 Hz, 3H, OCH$_3$), 7.85 (dd, $J_{H-F}$=11.0 Hz, 9.0 Hz, 1H, aromatic). $^{19}$F{$^1$H} NMR (282 MHz, DMSO-d$_6$): δ−146.4 (d, $J_{F-F}$=23.0 Hz, 1F), −140.2 (d, $J_{F-F}$=23.0 Hz, 1F). LCMS m/z calcd for C$_{14}$H$_{10}$F$_2$N$_2$O$_3$S 324 ([M$^+$]). found 325 ([M+H]$^+$).

Example 4

Synthesis of 9-Cyclopropyl-7-fluoro-8-methoxy-9H-isothiazolo[5,4-b]quinoline-3,4-dione (4)

9-Cyclopropyl-7-fluoro-8-methoxy-9H-isothiazolo[5,4-b]quinoline-3,4-dione (4) is prepared in accordance with the following synthetic scheme.

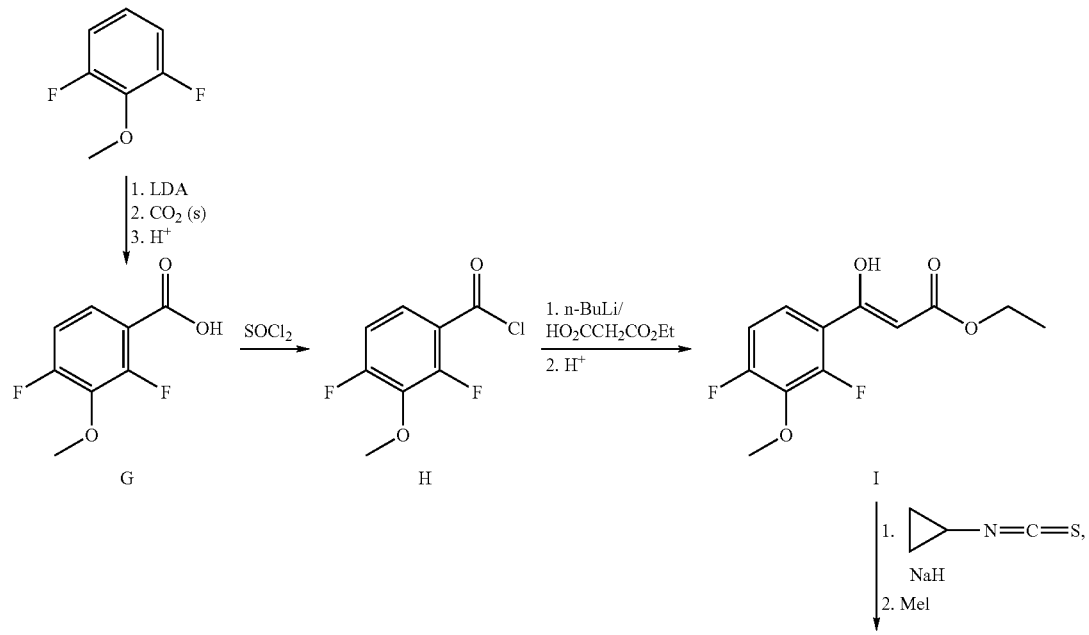

-continued

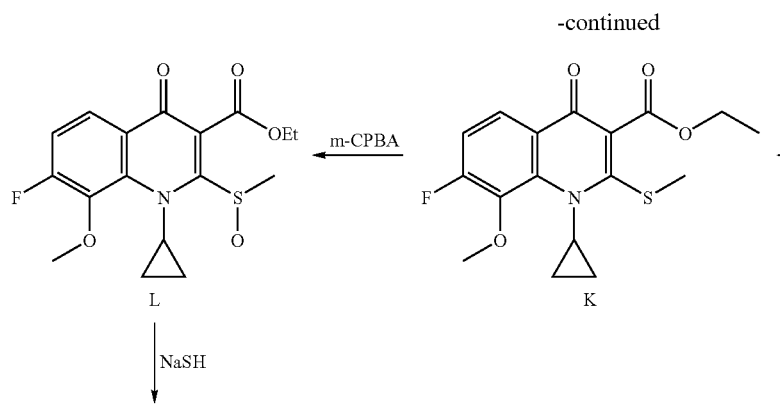 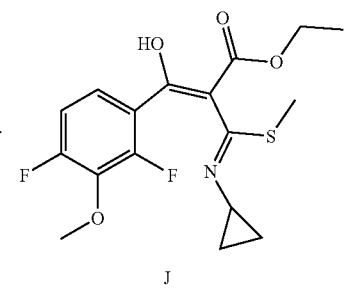

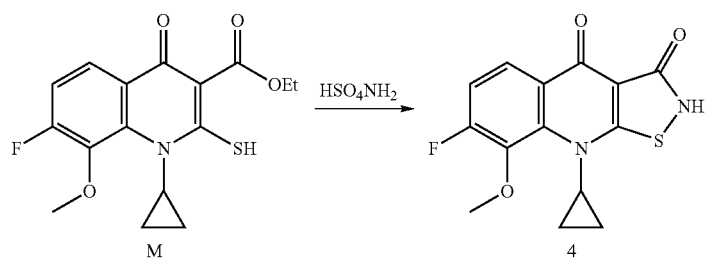

Step 1. Synthesis of Z 4-difluoro-3-methoxybenzoic acid (G)

Lithium diisopropylamide (LDA) is formed by dropwise addition of n-butyllithium (1.6 M in hexanes, 39 mL, 62 mmol) to a stirred solution of diisopropylamine (9.1 mL, 65 mmol) in tetrahydrofuran (120 mL) at −78° C. The resulting solution is stirred at −78° C. for 5 min, −20° C. for 15 min, and then cooled again to −78° C. This solution of LDA is added dropwise to a cooled (−78° C.) solution of 1,3-difluoro-2-methoxybenzene (7.15 g, 50 mmol) in tetrahydrofuran (150 mL) over a period of 30 min. The reaction mixture is allowed to warm to −20° C., cooled to −78° C., and bubbled with carbon dioxide gas for ~30 min. The resulting mixture is acidified to pH ~2 by addition of a 2 M aqueous solution of hydrochloric acid, and the product is extracted with ethyl acetate (2×200 mL). The combined organic extracts are washed with brine (100 mL), dried over sodium sulfate, and evaporated under reduced pressure. The remaining residue is suspended in water (80 mL). The residue dissolved once the solution is adjusted to pH ~9 via addition of a 2 M aqueous solution of sodium hydroxide. This solution is washed with diethyl ether (2×30 mL) and acidified slowly to pH ~2 by addition of a 2 M aqueous solution of hydrochloric acid. The product is extracted with ethyl acetate (2×200 mL), and the combined organic extracts are washed with brine (100 mL), dried over sodium sulfate, and concentrated under reduced pressure to give G as a pale yellow solid. This product is used directly in the next synthetic step. $^1$H NMR (300 MHz, DMSO-$d_6$) δ 3.93 (s, 3H, OCH$_3$), 7.24 (ddd, $J_{H\text{-}F}$=10.5 Hz, $J_{H\text{-}H}$=9.0 Hz, $J_{H\text{-}F}$=2.0 Hz, 1H, aromatic H-5), 7.62 (ddd, $J_{H\text{-}H}$=9.0 Hz, $J_{H\text{-}F}$=8.0 Hz, $J_{H\text{-}F}$=6.0 Hz, 1H, aromatic H-6).

Step 2. Synthesis of 2,4-difluoro-3-methoxybenzoyl chloride (H)

A mixture of 2,4-difluoro-3-methoxybenzoic acid (2.1 g, 11.1 mmol), thionyl chloride (5 mL), and ethyl acetate (30 mL) is refluxed for 4 h. All volatiles are removed in vacuo, and the remaining residue is used directly in the next synthetic step.

Step 3. Synthesis of (Z)-ethyl 3-hydroxy-3-(2,4-difluoro-3-methoxyphenyl)acrylate (I)

Compound I is prepared using the general method of Wierenga and Skulnick (Wierenga, W.; Skulnick, H. I. *J. Org. Chem.* 1979, 44, 310-311). n-Butyllithium (1.6 M in hexanes) is added to a cooled (−78° C.) solution of tetrahydrofuran (50 mL) containing ethyl hydrogen malonate (2.6 mL, 22 mmol) and 2,2'-bipyridyl (∼1 mg as indicator). The temperature of the reaction mixture is allowed to rise to ca. −5° C. during the addition of n-butyllithium. Sufficient n-butyllithium (30 mL, 48 mmol) is added until a pink color persists at −5° C. for 5-10 min. A solution of 2,4-difluoro-3-methoxybenzoyl chloride (H) (11.1 mmol, vide supra) in tetrahydrofuran (10 mL) is added in one portion to the reaction mixture that has been recooled to −78° C. The resulting mixture is allowed to warm to room temperature, diluted with ethyl acetate (100 mL), and quenched with a 1 M aqueous solution of hydrochloric acid. The organic layer is washed with a 5% aqueous solution of sodium bicarbonate (2×80 mL), followed by brine (2×80 mL), dried over sodium sulfate, and evaporated under reduced pressure to give the crude product. This material is purified by flash column chromatography (eluting with 20% v/v ethyl acetate in hexanes) to give pure I as a white solid. $^1$H NMR (300 MHz, CDCl$_3$): (keto, predominant tautomer, ∼80%) a 1.20 (t, $J_{H-H}$=7.0 Hz, 3H, CO$_2$CH$_2$CH$_3$), 3.88 (d, $J_{H-F}$=4.0 Hz, 2H, CH$_2$CO$_2$CH$_2$CH$_3$), 3.98 (apparent t, $J_{H-F}$=1.0 Hz, 3H, OCH$_3$), 4.15 (q, $J_{H-H}$=7.0 Hz, 2H, CO$_2$CH$_2$CH$_3$), 6.92 (ddd, $J_{H-F}$=11.0 Hz, $J_{H-H}$=9.0 Hz, $J_{H-F}$=2.0 Hz, 1H, aromatic H-5), 7.57 (ddd, $J_{H-H}$=9.0 Hz, $J_{H-F}$=7.5 Hz, $J_{H-F}$=6.0 Hz, 1H, aromatic H-6). LCMS m/z calcd for C$_{12}$H$_{12}$F$_2$O$_4$ 258 ([M$^+$]). found 259 ([M+H]$^+$).

Step 4. Synthesis of (E)-ethyl 2-((Z)—N-cyclopropyl(methylthio)carbonoimidoyl)-3-hydroxy-3-(2,4-difluoro-3-methoxyphenyl)acrylate (J)

Sodium hydride (60% in mineral oil, 212 mg, 5.31 mmol) is added portionwise to a cooled (0° C.) solution containing I (1.28 g, 4.96 mmol), cyclopropyl isothiocyanate (781 μL, 8.43 mmol), and dimethylformamide (13 mL). The resulting mixture is allowed to warm to room temperature with stirring overnight (18 h). Methyl iodide (525 μL, 8.43 mmol) is added to the resulting solution and stirred for an additional 4 h (until TLC indicated the complete consumption of I). The reaction mixture is diluted with ethyl acetate (250 mL) and quenched by addition of a saturated aqueous solution of ammonium chloride (75 mL). The organic layer is washed with brine (4×100 mL), dried over sodium sulfate, and evaporated under reduced pressure to give the crude product. This material is purified by flash column chromatography (eluting with 40% v/v ethyl acetate in hexanes) to give of J as a yellow oil. $^1$H NMR (300 MHz, CDCl$_3$): δ 0.80-1.01 (m, 7H), 2.52 (s, 3H, SCH$_3$), 3.02 (m, 1H, cyclopropyl CH), 3.91 (q, $J_{H-H}$=7.5 Hz, 2H, CO$_2$CH$_2$CH$_3$), 3.97 (s, 3H, OCH$_3$), 6.88 (ddd, $J_{H-F}$=10.0 Hz, $J_{H-H}$=9.0 Hz, $J_{H-F}$=1.5 Hz, 1H, aromatic H-5), 7.07 (ddd, $J_{H-H}$=9.0 Hz, $J_{H-F}$=7.0 Hz, $J_{H-F}$=6.0 Hz, 1H, aromatic H-6), 11.78 (s, 1H, OH). $^{19}$F{$^1$H} NMR (282 MHz, CDCl$_3$): δ−130.8 (d, $J_{F-F}$=10.5 Hz, 1F), −126.8 (d, $J_{F-F}$=10.5 Hz, 1F), LCMS m/z calcd for C$_{17}$H$_{19}$F$_2$NO$_4$S 371 ([M$^+$]). found 372 ([M+H]$^+$).

Step 5. Synthesis of ethyl 1-cyclopropyl-7-fluoro-8-methoxy-2-(methylthio)-4-oxo-1,4-dihydroquinoline-3-carboxylate (K)

Sodium hydride (60% in mineral oil, 142 mg, 3.54 mmol) is added portionwise to a solution of J (1.25 g, 3.37 mmol) in dimethylformamide (18 mL) at room temperature. The reaction mixture is heated at 75° C. for 18 h (until TLC indicated the complete consumption of J), cooled to room temperature, and quenched by addition of a saturated aqueous solution of ammonium chloride (20 mL). The mixture is extracted with ethyl acetate (3×100 mL). The combined organic extracts are washed with brine (4×50 mL), dried over sodium sulfate, and evaporated under reduced pressure to give crude K as a pale yellow oil. This product is of sufficient purity (≧95% by NMR spectroscopy) to use directly in the next synthetic step. $^1$H NMR (300 MHz, CDCl$_3$): δ 0.72 (m, 2H, cyclopropyl CH$_2$), 1.17 (m, 2H, cyclopropyl CH$_2$), 1.38 (t, $J_{H-H}$=7.0 Hz, 3H, CO2CH$_2$CH$_3$), 2.62 (s, 3H, SCH$_3$), 3.75 (m, 1H, cyclopropyl CH), 4.00 (d, $J_{H-F}$=2.0 Hz, 3H, OCH$_3$), 4.39 (q, $J_{H-H}$=7.0 Hz, 2H, CO2CH$_2$CH$_3$), 7.12 (dd, $J_{H-F}$=11.0 Hz, $J_{H-H}$=9.0 Hz, 1H, aromatic H-6), 7.95 (dd, $J_{H-H}$=9.0 Hz, $J_{H-F}$=6.0 Hz, 1H, aromatic H-5). $^{19}$F{$^1$H} NMR (282 MHz, CDCl$_3$): δ−123.7 (s, 1F). LCMS m/z calcd for C$_{17}$H$_{18}$FNO$_4$S 351 ([M$^+$]). found 352 ([M+H]$^+$).

Step 6. Synthesis of ethyl 1-cyclopropyl-7-fluoro-8-methoxy-2-(methylsulfinyl)-4-oxo-1,4-dihydroquinoline-3-carboxylate (L)

m-Chloroperoxybenzoic acid (≦77%, 527 mg, 2.35 mmol) is added in one portion to a cooled (−5° C.) solution of K (0.75 g, 2.14 mmol) in methylene chloride (20 mL). The reaction mixture is stirred at 0° C. for 2.5 h, diluted with ethyl acetate (100 mL), and washed with a 5% aqueous solution of sodium bicarbonate (2×30 mL). The organic layer is dried over sodium sulfate and evaporated under reduced pressure to give the crude product. This material is purified by flash column chromatography (eluting with 5% v/v chloroform in ethyl acetate) to give pure L as a yellow solid. $^1$H NMR (300 MHz, CDCl$_3$): δ 0.60 (m, 1H, cyclopropyl CH$_2$), 0.99 (m, 1H, cyclopropyl CH$_2$), 1.11 (m, 1H, cyclopropyl CH$_2$), 1.26 (m, 1H, cyclopropyl CH$_2$), 1.35 (t, $J_{H-H}$=7.5 Hz, 3H, CO$_2$CH$_2$CH$_3$), 3.19 (s, 3H, S(O)CH$_3$), 3.81 (m, 1H, cyclopropyl CH), 4.00 (d, $J_{H-F}$=2.0 Hz, 3H, OCH$_3$), 4.37 (m, 2H, CO$_2$CH$_2$CH$_3$), 7.15 (dd, $J_{H-F}$=10.5 Hz, $J_{H-H}$=9.0 Hz, 1H, aromatic H-6), 7.93 (dd, $J_{H-H}$=9.0 Hz, $J_{H-F}$=6.0 Hz, 1H, aromatic H-5). $^{19}$F{$^1$H} NMR (282 MHz, CDCl$_3$): δ−122.1 (s). LCMS m/z calcd for C$_{17}$H$_{18}$FNO$_5$S 367 ([M$^+$]). found 368 ([M+H]$^+$)

Step 7. Synthesis of ethyl 1-cyclopropyl-7-fluoro-2-mercapto-8-methoxy-4-oxo-1,4-dihydroquinoline-3-carboxylate (M)

Anhydrous sodium hydrogen sulfide (Alfa Aesar, 137 mg, 2.45 mmol) is added in one portion to a solution of dimethylformamide (10 mL) containing L (600 mg, 1.63 mmol) at −5° C. The resulting mixture is stirred for 15 min (until TLC indicated complete consumption of L) and allowed to warm to room temperature. The reaction mixture is quenched by addition of a 5% aqueous solution of hydrochloric acid (75 mL) and extracted with ethyl acetate (2×100 mL). The combined organic extracts are washed with brine (4×75 mL), dried over sodium sulfate, and evaporated to dryness under reduced pressure to give crude M (≧90% purity by LC-MS). This material is used directly in the next synthetic step to prevent its oxidative degradation. LCMS m/z calcd for $C_{16}H_{16}FNO_4S$ 337 ([M$^+$]). found 338 ([M+H]$^+$).

Synthesis of 9-cyclopropyl-7-fluoro-8-methoxy-isothiazolo[5,4-b]quinoline-3,4(2H, 9H)-dione (4)

A solution of sodium bicarbonate (1.3 g, 15.47 mmol) in water (22 mL) is added to a solution of M (540 mg, 1.60 mmol) in tetrahydrofuran (16 mL) at room temperature. Hydroxylamine-O-sulfonic acid (761 mg, 6.73 mmol) is added in one portion to this mixture. The reaction mixture is stirred at room temperature for ~3 h and quenched by addition of an aqueous solution of 5% hydrochloric acid (150 mL). The precipitate that formed is collected by filtration, washed with water (3×10 mL), and dried in vacuo to give 4 as a white solid. This product is of sufficient purity (≧95% by $^1$H NMR spectroscopy) to use directly in the final amine-coupling step. $^1$H NMR (300 MHz, DMSO-d$_6$): δ 1.11 (m, 2H, cyclopropyl $CH_2$), 1.26 (m, 2H, cyclopropyl $CH_2$), 3.92 (m, 1H, cyclopropyl CH), 4.00 (d, $J_{H-F}$=1.5 Hz, 3H, $OCH_3$), 7.43 (dd, $J_{H-F}$=10.5 Hz, $J_{H-H}$=9.0 Hz 1H, aromatic H-6), 8.06 (dd, $J_{H-H}$=9.0 Hz, $J_{H-F}$=6.0 Hz 1H, aromatic H-5). $^{19}$F{$^1$H} NMR (282 MHz, CDCl$_3$): δ−119.1 (s). LCMS m/z calcd for $C_{14}H_{11}FN_2O_3S$ 306 ([M$^+$]). found 307 ([M+H]$^+$).

Example 5

Synthesis of 1-Methyl-1-pyrrolidin-3-yl ethylamine (5)

1-Methyl-1-pyrrolidin-3-yl-ethylamine is prepared in accordance with the synthetic scheme below.

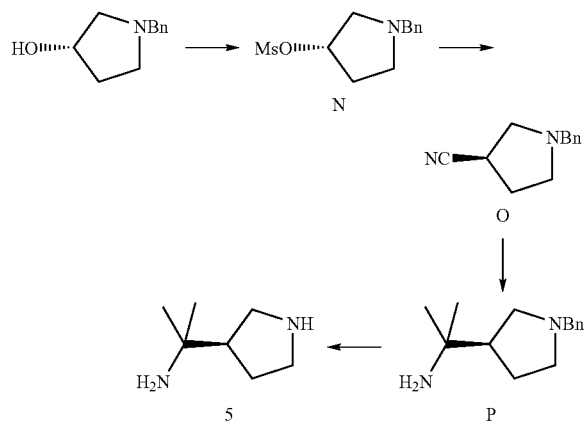

Step 1. Synthesis of (S)-1-benzylpyrrolidin-3-yl methanesulfonate (N)

Methanesulfonyl chloride (15 mL, 0.19 mol) is added to a cooled (0° C.) solution of toluene (300 mL) containing (S)-1-benzylpyrrolidin-3-ol (24.5 g, 0.14 mol) and triethylamine (80 mL, 0.57 mol). The resulting mixture is stirred at 0° C. for 15 min, and allowed to warm to room temperature with stirring for 2 h. The mixture is quenched with a 5% aqueous solution of sodium bicarbonate (250 mL). The organic layer is washed with a 5% aqueous solution of sodium bicarbonate (2×250 mL), washed with water (1×250 mL), dried over magnesium sulfate, and concentrated under reduced pressure to give N (35.1 g, 99%) as an orange oil. $^1$H NMR (300 MHz, CDCl$_3$): δ 2.07 (m, 1H), 2.30 (m, 1H), 2.49 (m, 1H), 2.75-2.90 (m, 3H), 2.98 (s, 3H), 3.61 (d, J=13.0 Hz, 1H), 3.68 (d, J=13.0 Hz, 1H), 5.18 (m, 1H), 7.15-7.30 (m, 5H). LCMS m/z calcd for $C_{12}H_{17}NO_3S$ 255 ([M$^+$]). found 256 ([M+H]$^+$, 100%), 160 (40%).

Steps 2 and 3. Syntheses of (R)-1-benzylpyrrolidine-3-carbonitrile (O) and 2-((R)-1-benzylpyrrolidin-3-yl)propan-2-amine (P)

The syntheses of O and P are described previously by Fedij et al. (Fedij, V.; Lenoir, E. A., III; Suto, M. J.; Zeller, J. R.; Wemple, J. *Tetrahedron: Asymmetry* 1994, 5, 1131-1134).

Step 4. Synthesis of 1-((R)-Methyl-1-pyrrolidin-3-yl)-ethylamine (5)

A mixture containing P (7.4 g), 20% palladium hydroxide on carbon (7.5 g), and ethanol (75 mL) is stirred under an atmosphere of hydrogen gas (50 psi) at 45° C. for 24 h. The mixture is filtered and the filtrate is concentrated under reduced pressure to give 5 (4.1 g, 95%) as a yellow oil. This material is stored under an atmosphere of argon gas. $^1$H NMR (300 MHz, CDCl$_3$): δ 1.09 (s, 6H), 1.51 (m, 1H), 1.64 (br s, 3H), 1.81 (m, 1H), 2.06 (apparent pentet, J=8.5 Hz, 1H), 2.69 (dd, J=11.0 Hz, J=8.5 Hz, 1H), 2.94 (m, 2H), 3.00 (dd, J=11.0 Hz, J=8.5 Hz, 1H). LCMS m/z calcd for $C_7H_{16}N_2$ 128 ([M$^+$]). found 129 ([M+H]$^+$, 60%), 112 (100%).

Example 6

General Method for the Final Amine-Coupling Step: Synthesis of 7-((R)-3-(2-aminopropan-2-yl)pyrrolidin-1-yl)-9-cyclopropyl-6-fluoro-8-methoxyisothiazolo[5,4-b]quinoline-3,4(2H,9H)-dione hydrochloride 7-((R)-3-(2-Aminopropan-2-yl)pyrrolidin-1-yl)-9-cyclopropyl-6-fluoro-8-methoxyisothiazolo[5,4-b]quinoline-3,4(2H,9H)-dione hydrochloride is prepared in accordance with the synthetic scheme below.

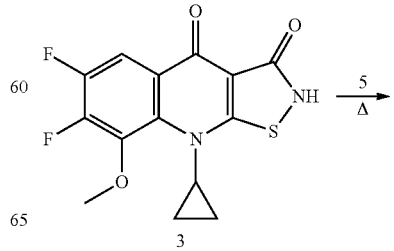

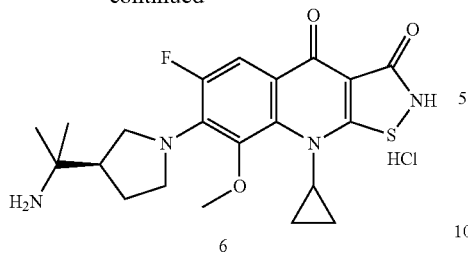

Synthesis of 7-((R)-3-(2-aminopropan-2-yl)pyrrolidin-1-yl)-9-cyclopropyl-6-fluoro-8-methoxyisothiazolo[5,4-b]quinoline-3,4(2H, 9H)-dione hydrochloride (6)

Under an atmosphere of argon, a reaction vessel is charged with 5 (206.0 mg, 1.6 mmol), 3 (328.6 mg, 1.0 mmol), dimethyl sulfoxide (4.5 mL), and N,N-diisopropylethylamine (750 μL, 4.3 mmol). The resulting mixture is irradiated with microwaves (CEM Discover) at 125° C. for 1 h (conventional heating may also be used—115° C. in an oil bath for 14 h), allowed to cool, and evaporated to dryness under reduced pressure (~70° C./2-3 mm Hg). The oily residue is triturated with ethyl acetate (15 mL) and the resulting powder is collected by centrifugation. This solid is purified using preparative HPLC to give the desired product. Preparative HPLC isperformed using a YMC Pack Pro C18 150×30.0 mm 5 μm column coupled to a YMC Pack Pro 50×20 mm 5 μm column with an isocratic elution of 0.37 min at 95:5H$_2$O:CH$_3$CN containing 0.1% TFA followed by a 15.94 min linear gradient elution from 95:5 to 25:75, followed by a 0.69 min linear gradient from 25:75 to 5:95 at a flow rate of 30.0 mL/min with UV detection at 254. The crude material is loaded as a solution containing acetic acid (~2 mL), methanol (~1 mL), and water (~1 mL). The purified product is isolated as the TFA salt and is converted to the corresponding hydrochloride salt by addition of a solution of hydrogen chloride (~1.25 M in methanol) followed by evaporation; this process is repeated twice to give a yellow solid. Purity by HPLC: ≧99%; $t_R$=10.08 min. $^1$H NMR (300 MHz, TFA-d): δ 1.28 (m, 2H), 1.53 (m, 2H), 1.66 (s, 6H), 2.43 (m, 1H), 2.57 (m, 1H), 3.35 (m, 1H), 3.97 (s, 3H), 4.01-4.38 (m, 5H), 8.17 (d, J=12.0 Hz, 1H, aromatic). $^{19}$F{$^1$H} (282 MHz, TFA-d): δ−118.0 (s). $^{13}$C{$^1$H} (75 MHz, TFA-d): δ 13.5, 13.9, 25.0, 25.1, 29.1, 39.7, 49.6, 59.4 (br, $W_{1/2}$≈14 Hz), 59.8 (br, $W_{1/2}$≈14 Hz), 60.0, 66.8, 106.0, 112.1 (d $J_{C-F}$=23.0 Hz), 137.5 (br m, $W_{1/2}$≈24 Hz), 138.4, 144.8 (br, $W_{1/2}$≈10 Hz), 155.3 (d $J_{C-F}$= 255.0 Hz), 169.8, 170.1, 171.5 (br, $W_{1/2}$≈9 Hz). LCMS m/z calcd for $C_{21}H_{25}FN_4O_3S$ 432 ([M$^+$]). found 433 ([M+H]$^+$). Anal. Calcd for $C_{21}H_{25}FN_4O_3S \cdot 1.5HCl \cdot 1.5H_2O$: C, 49.05; H, 5.78; N, 10.90; Cl, 10.34. Found: C, 49.30; H, 5.60; N, 10.83; Cl, 10.00.

Example 7

Synthesis of 7-((R)-3-(2-aminopropan-2-yl)pyrrolidin-1-yl)-9-cyclopropyl-8-methoxyisothiazolo[5,4-b]quinoline-3,4(2H,9H)-dione hydrochloride (7)

7-((R)-3-(2-Aminopropan-2-yl)pyrrolidin-1-yl)-9-cyclopropyl-8-methoxyisothiazolo[5,4-b]quinoline-3,4(2H,9H)-dione hydrochloride (7) is prepared via the procedure outlined above in Example 6 for 6 using 4 as starting material. Purity by HPLC: ≧99%. $^1$H NMR (300 MHz, DMSO-d$_6$): δ 0.92 (m, 2H), 1.34 (m, 2H), 1.33 (s, 6H), 1.84 (m, 1H), 2.05 (m, 1H), 2.55 (m, 1H), 3.44 (m, 2H), 3.49 (s, 3H), 3.55 (m, 2H), 3.78 (m, 1H), 6.86 (d, J=9.0 Hz, 1H), 7.82 (d, J=9.0 Hz, 1H). LCMS m/z calcd for $C_{21}H_{26}N_4O_3S$ 414 ([M$^+$]). found 415 ([M+H]$^+$).

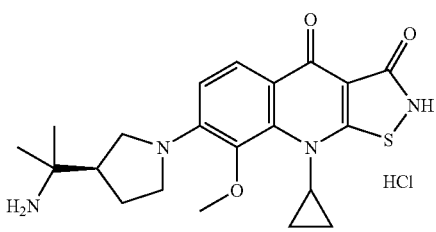

Synthesis of 7-((R)-3-(2-aminopropan-2-yl)pyrrolidin-1-yl)-9-cyclopropyl-6-fluoroisothiazolo[5,4-b]quinoline-3,4(2H, 9H)-dione hydrochloride (8)

7-((R)-3-(2-Aminopropan-2-yl)pyrrolidin-1-yl)-9-cyclopropyl-6-fluoroisothiazolo[5,4-b]quinoline-3,4(2H,9H)-dione hydrochloride is prepared via the procedure outlined above in Example 6 for 6 using 2 as starting material. Purity by HPLC: ≧98%. $^1$H NMR (300 MHz, DMSO-d$_6$)/acetic acid-d$_4$ (~10:1 v/v)): 1.15 (m, 2H), 1.30 (s, 6H), 1.33 (m, 2H), 1.84 (m, 1H), 2.04 (m, 1H), 2.54 (m, 1H), 3.32-3.71 (m, 5H), 6.89 (d, $J_{H-F}$=7.5 Hz, 1H), 7.60 (d, $J_{H-F}$=14.0 Hz, 1H). $^{19}$F{$^1$H} (282 MHz, DMSO-d$_6$)/acetic acid-d$_4$ (~10:1 v/v)): δ−131.8 (s). LCMS m/z calcd for $C_{20}H_{23}FN_4O_2S$ 402 ([M$^+$]). found 403 ([M+H]$^+$).

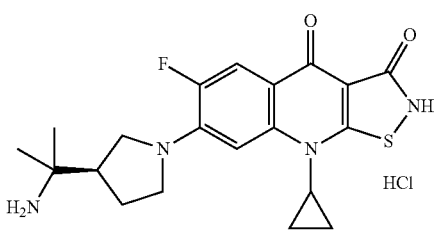

Synthesis of 7-((R)-3-(2-aminopropan-2-yl)pyrrolidin-1-yl)-9-cyclopropyl-6-fluoroisothiazolo[5,4-b][1,8]naphthyridine-3,4(2H, 9H)-dione hydrochloride (9)

7-((R)-3-(2-Aminopropan-2-yl)pyrrolidin-1-yl)-9-cyclopropyl-6-fluoroisothiazolo[5,4-b][1,8]naphthyridine-3,4(2H,9H)-dione hydrochloride is prepared via the procedure outlined above in Example 6 for 6 using 1 as starting material. Purity by HPLC: ≧98%. $^1$H NMR (300 MHz, DMSO-d$_6$)/acetic acid-d$_4$ (~10:1 v/v)): δ 1.11 (m, 2H), 1.20 (m, 2H), 1.28 (s, 6H), 1.82 (m, 1H), 2.02 (m, 1H), 2.48 (m, 1H), 3.27 (m, 1H), 3.51 (m, 1H), 3.64 (m, 1H), 3.93 (m, 2H), 7.82 (d, $J_{H-F}$=13.0 Hz, 1H). $^{19}$F{$^1$H} (282 MHz, DMSO-d$_6$)/acetic acid-d$_4$ (~10:1 v/v)): δ–139.8 (s). LCMS m/z calcd for C$_{19}$H$_{22}$FN$_5$O$_2$S 403 ([M$^+$]). found 404 ([M+H]$^+$).

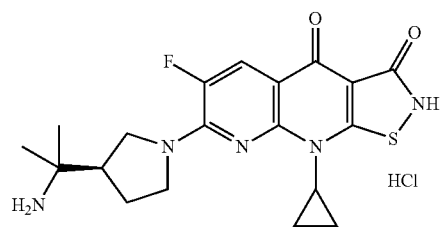

9

Synthesis of 1-((R)-pyrrolidin-3-yl)cyclopropanamine (10)

1-((R)-Pyrrolidin-3-yl)cyclopropanamine (10) is prepared using the method of Inagaki et al. (Inagaki, H.; Miyauchi, S.; Miyauchi, R. N.; Kawato, H. C.; Ohki, H.; Matsuhashi, N.; Kawakami, K.; Takahashi, H.; Takemura, M. *J. Med. Chem.* 2003, 46, 1005-1015).

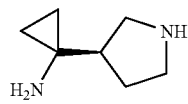

10

Synthesis of 7-((R)-3-(1-aminocyclopropyl)pyrrolidin-1-yl)-9-cyclopropyl-6-fluoro-8-methoxyisothiazolo[5,4-b]quinoline-3,4(2H, 9H)-dione hydrochloride (11)

7-((R)-3-(1-Aminocyclopropyl)pyrrolidin-1-yl)-9-cyclopropyl-6-fluoro-8-methoxyisothiazolo[5,4-b]quinoline-3,4(2H,9H)-dione hydrochloride (11) is prepared via the procedure outlined above in Example 6 for 6 using 10 as starting material. Purity by HPLC: ≧98%. $^1$H NMR (300 MHz, CD$_3$OD): δ 1.02 (m, 6H), 1.26 (m, 2H), 1.74 (m, 1H), 2.16 (m, 1H), 2.70 (m, 1H), 3.60 (s, 3H), 3.62 (m, 2H), 3.74 (m, 1H), 3.87 (m, 2H), 7.69 (d, $J_{H-F}$=14.0 Hz, 1H). $^{19}$F{$^1$H} NMR (282 MHz, CD$_3$OD): δ–126.2. LCMS m/z calcd for C$_{21}$H$_{23}$FN$_4$O$_3$S 430 ([M$^+$]). found 431 ([M+H]$^+$).

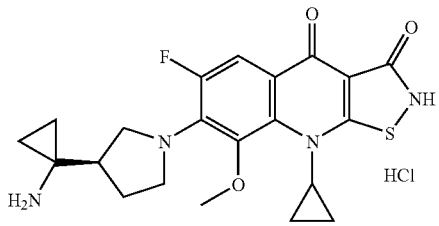

11

Synthesis of 7-((R)-3-(1-aminocyclopropyl)pyrrolidin-1-yl)-9-cyclopropyl-8-methoxyisothiazolo[5,4-b]quinoline-3,4(2H, 9H)-dione hydrochloride (12)

7-((R)-3-(1-Aminocyclopropyl)pyrrolidin-1-yl)-9-cyclopropyl-8-methoxyisothiazolo[5,4-b]quinoline-3,4(2H,9H)-dione hydrochloride (12) is prepared via the procedure outlined above in Example 6 for 6 using 4 and 10 as starting materials. Purity by HPLC: ≧98%. $^1$H NMR (300 MHz, CD$_3$OD): δ 0.93 (m, 6H), 1.18 (m, 2H), 1.69 (m, 1H), 2.10 (m, 1H), 2.65 (m, 1H), 3.32 (m, 1H), 3.47 (s, 3H), 3.60 (m, 3H), 3.80 (m, 1H), 6.91 (d, $J_{H-H}$=9.0 Hz, 1H), 7.91 (d, $J_{H-H}$=9.0 Hz, 1H). LCMS m/z calcd for C$_{21}$H$_{24}$N$_4$O$_3$S 412 ([M$^+$]). found 413 ([M+H]$^+$).

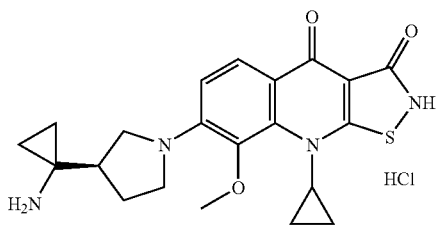

12

Synthesis of 9-cyclopropyl-6-fluoro-7-(octahydropyrrolo[3,4-b]pyridin-6-yl)-8-methoxyisothiazolo[5,4-b]quinoline-3,4(2H,9H)-dione hydrochloride (13)

9-Cyclopropyl-6-fluoro-7-(octahydropyrrolo[3,4-b]pyridin-6-yl)-8-methoxyisothiazolo[5,4-b]quinoline-3,4(2H, 9H)-dione hydrochloride (13) is prepared via the procedure outlined above in Example 6 for 6 using commercially available (rac)-cis-octahydropyrrolo[3,4-b]pyridine as starting material. Purity by HPLC: ≧98%. ¹H NMR (300 MHz, DMSO-d₆): δ 1.13 (m, 2H, cyclopropyl CH₂), 1.16 (m, 2H, cyclopropyl CH₂), 1.78 (m, 4H), 2.54(m, 1H), 2.89 (m, 1H), 3.17 (m, 1H), 3.56 (s, 3H, OCH₃), 3.61-4.19 (m, 6H), 7.56 (d, (J$_{H-F}$=13.5 Hz, 1H, aromatic). ¹⁹F{¹H} NMR (282 MHz, DMSO-d₆): δ–125.3 (s). LCMS m/z calcd for C₂₁H₂₃FN₄O₃S 430 ([M⁺]). found 431 ([M+H]⁺).

dione hydrochloride (15) is prepared via the procedure outlined above in Example 6 for 6 using 1 and commercially available (rac)-cis-octahydropyrrolo[3,4-b]pyridine as starting materials. Purity by HPLC: ≧98%. ¹H NMR (300 MHz, DMSO-d₆): (selected data) δ 7.58 (br, aromatic). ¹⁹F{¹H} NMR (282 MHz, DMSO-d₆): δ–140.5 (br). LCMS m/z calcd for C₁₉H₂₀FN₅O₂S 401 ([M⁺]). found 402 ([M+H]⁺).

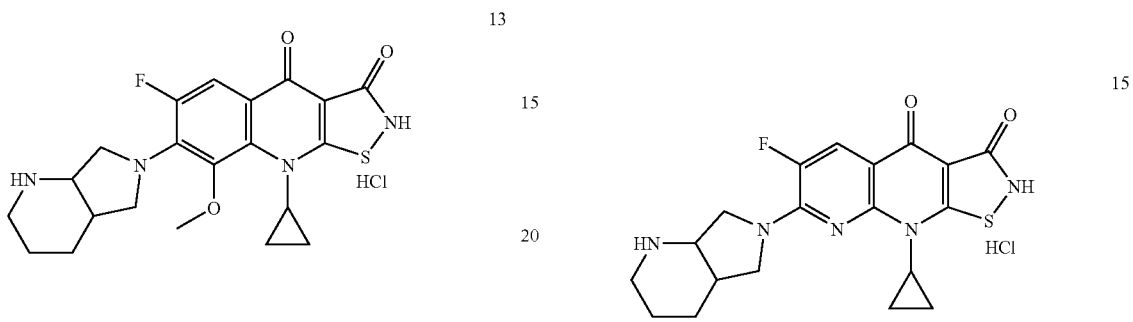

Synthesis of 9-cyclopropyl-6-fluoro-7-(octahydropyrrolo[3,4-b]pyridin-6-yl)isothiazolo[5,4-b]quinoline-3,4(2H, 9H)-dione hydrochloride (14)

9-Cyclopropyl-6-fluoro-7-(octahydropyrrolo[3,4-b]pyridin-6-yl)isothiazolo[5,4-b]quinoline-3,4(2H,9H)-dione hydrochloride (14) is prepared via the procedure outlined above in Example 6 for 6 using 2 and commercially available (rac)-cis-octahydropyrrolo[3,4-b]pyridine as starting materials. Purity by HPLC: ≧98%. ¹H NMR (300 MHz, CD₃OD): δ 1.22 (m, 4H, cyclopropyl CH₂), 1.81 (m, 4H), 2.89 (m, 3H), 3.20 (m, 1H), 3.63 (m, 2H), 3.89 (m, 3H), 6.75 (br, 1H, aromatic H-8), 7.44 (d, J$_{H-F}$=14.0 Hz, 1H, aromatic H-6). ¹⁹F{¹H} NMR (282 MHz, CD₃OD): δ–132.2 (s). LCMS m/z calcd for C₂₀H₂₁FN₄O₂S 400 ([M⁺]). found 401 ([M+H]⁺).

Synthesis of 9-cyclopropyl-6-fluoro-7-((4aS,7aS)-octahydropyrrolo[3,4-b]pyridin-6-yl)-8-methoxy-isothiazolo[5,4-b]quinoline-3,4(2H, 9H)-dione (16)

9-Cyclopropyl-6-fluoro-7-((4aS,7aS)-octahydropyrrolo[3,4-b]pyridin-6-yl)-8-methoxyisothiazolo[5,4-b]quinoline-3,4(2H,9H)-dione hydrochloride (16) is prepared via the procedure outlined above in Example 6 for 6 using 3 and (4aS,7aS)-octahydro-1H-pyrrolo[3,4-b]pyridine as starting materials. MW 430.496.

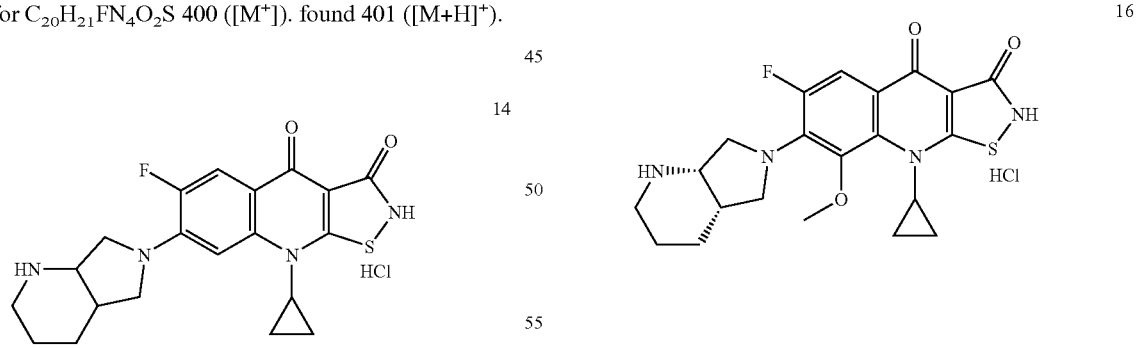

Example 8

Additional 9H-isothiazolo[5,4-b]quinoline-3,4-diones and Related Compounds

Synthesis of 9-cyclopropyl-6-fluoro-7-(octahydropyrrolo[3,4-b]pyridin-6-yl)isothiazolo[5,4-b][1,8]naphthyridine-3,4(2H,9H)-dione hydrochloride (15)

9-Cyclopropyl-6-fluoro-7-(octahydropyrrolo[3,4-b]pyridin-6-yl)isothiazolo[5,4-b][1,8]naphthyridine-3,4(2H,9H)-

Additional compounds of Formula I and II prepared by the methods exemplified in Examples 1 to 7 are disclosed in TABLE II

TABLE II

| No. | Structure | Name | Salt | MW | MS | H-NMR | F-NMR |
|---|---|---|---|---|---|---|---|
| 17 | 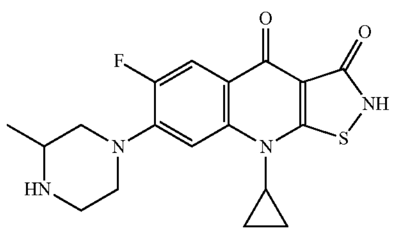 | 9-cyclopropyl-6-fluoro-7-(3-methyl-piperazin-1-yl)isothiazolo[5,4-b]quinoline-3,4(2H,9H)-dione | | 374.4 | | | |
| 18 | 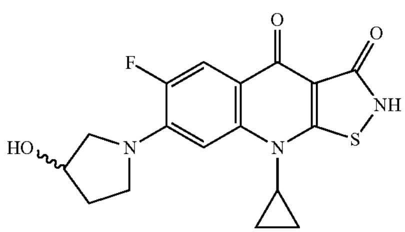 | 9-cyclopropyl-6-fluoro-7-(3-hydroxy-pyrrolidin-1-yl)isothiazolo[5,4-b]quinoline-3,4(2H,9H)-dione | | 361.4 | | | |
| 19 | 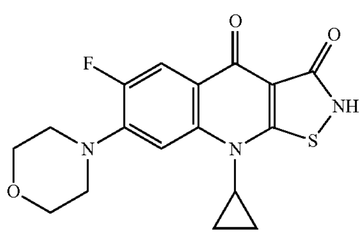 | 9-cyclopropyl-6-fluoro-7-morpholino-isothiazolo[5,4-b]quinoline-3,4(2H,9H)-dione | | 361.4 | | | |
| 20 | 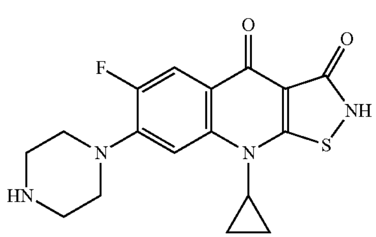 | 9-cyclopropyl-6-fluoro-7-(piperazin-1-yl)isothiazolo[5,4-b]quinoline-3,4(2H,9H)-dione | | 360.4 | | | |

TABLE II-continued

| No. | Structure | Name | Salt | MW | MS | H-NMR | F-NMR |
|---|---|---|---|---|---|---|---|
| 21 | 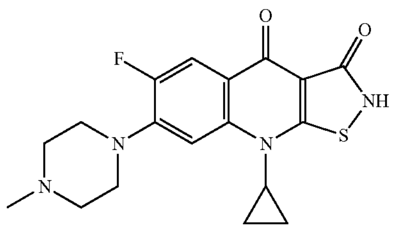 | 9-cyclopropyl-6-fluoro-7-(4-methyl-piperazin-1-yl)isothiazolo[5,4-b]quinoline-3,4(2H,9H)-dione | | 374.4 | | | |
| 22 | 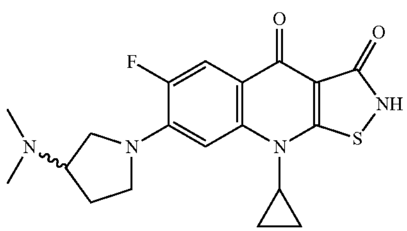 | 9-cyclopropyl-7-(3-(dimethyl-amino)pyrrolidin-1-yl)-6-fluoroisothiazolo[5,4-b]quinoline-3,4(2H,9H)-dione | | 388.5 | | | |
| 23 | 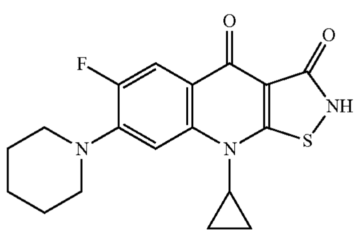 | 9-cyclopropyl-6-fluoro-7-(piperidin-1-yl)isothiazolo[5,4-b]quinoline-3,4(2H,9H)-dione | | 359.4 | | | |
| 24 | 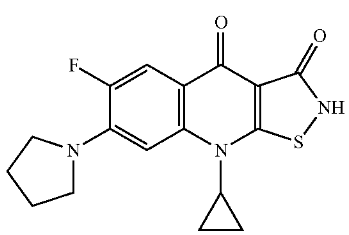 | 9-cyclopropyl-6-fluoro-7-(pyrrolidin-1-yl)isothiazolo[5,4-b]quinoline-3,4(2H,9H)-dione | | 345.4 | | | |

TABLE II-continued

| No. | Structure | Name | Salt | MW | MS | H-NMR | F-NMR |
|---|---|---|---|---|---|---|---|
| 25 | 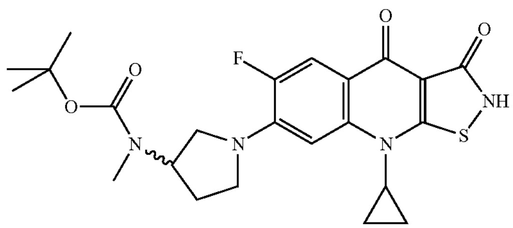 | tert-butyl 1-(9-cyclopropyl-6-fluoro-3,4-dioxo-2,3,4,9-tetrahydroisothiazolo[5,4-b]quinolin-7-yl)pyrrolidin-3-yl(methyl)carbamate | | 474.5 | | | |
| 26 | 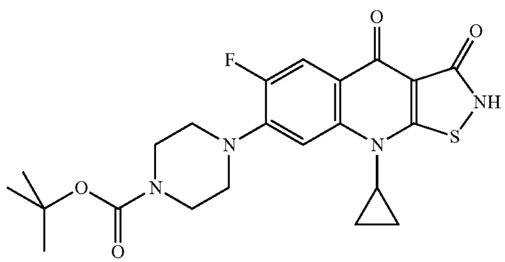 | tert-butyl 4-(9-cyclopropyl-6-fluoro-3,4-dioxo-2,3,4,9-tetrahydroisothiazolo[5,4-b]quinolin-7-yl)piperazine-1-carboxylate | | 460.5 | | | |
| 27 | 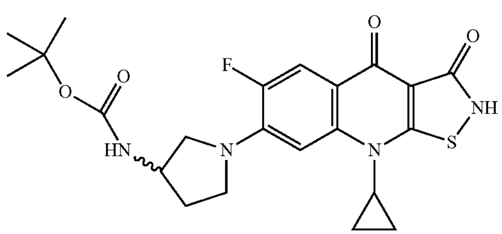 | tert-butyl 1-(9-cyclopropyl-6-fluoro-3,4-dioxo-2,3,4,9-tetrahydroisothiazolo[5,4-b]quinolin-7-yl)pyrrolidin-3-ylcarbamate | | 460.5 | | | |
| 28 | 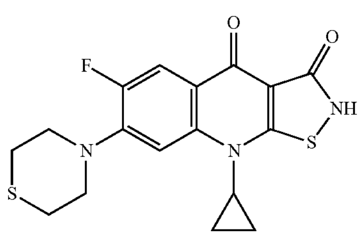 | 9-cyclopropyl-6-fluoro-7-thiomorpholinoisothiazolo[5,4-b]quinoline-3,4(2H,9H)-dione | | 377.5 | | | |

TABLE II-continued

| No. | Structure | Name | Salt | MW | MS | H-NMR | F-NMR |
|---|---|---|---|---|---|---|---|
| 29 | 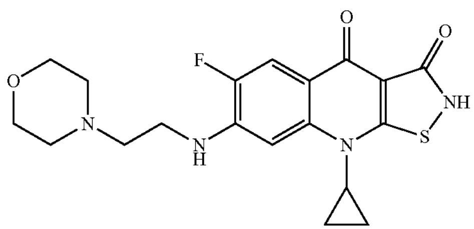 | 9-cyclopropyl-6-fluoro-7-(2-morpholinoethyl-amino)isothiazolo[5,4-b]quinoline-3,4(2H,9H)-dione | | 404.5 | | | |
| 30 | 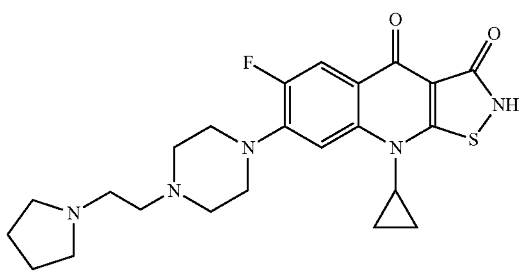 | 9-cyclopropyl-6-fluoro-7-(4-(2-(pyrrolidin-1-yl)ethyl)piperazin-1-yl)isothiazolo[5,4-b]quinoline-3,4(2H,9H)-dione | | 457.6 | | | |
| 31 | 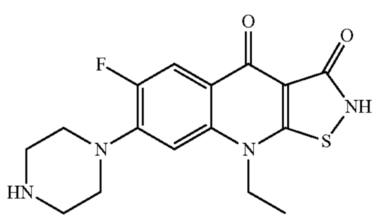 | 9-ethyl-6-fluoro-7-(piperazin-1-yl)isothiazolo[5,4-b]quinoline-3,4(2H,9H)-dione | | 348.4 | | | |
| 32 | 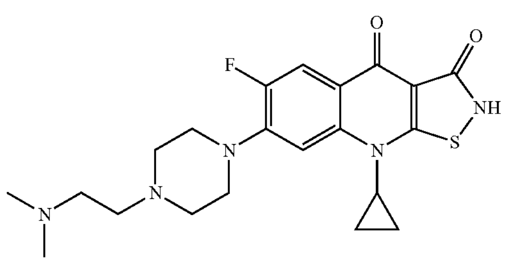 | 9-cyclopropyl-7-(4-(2-(dimethylamino)ethyl)piperazin-1-yl)-6-fluoroisothiazolo[5,4-b]quinoline-3,4(2H,9H)-dione | | 431.5 | | | |

TABLE II-continued

| No. | Structure | Name | Salt | MW MS | H-NMR | F-NMR |
|---|---|---|---|---|---|---|
| 33 | 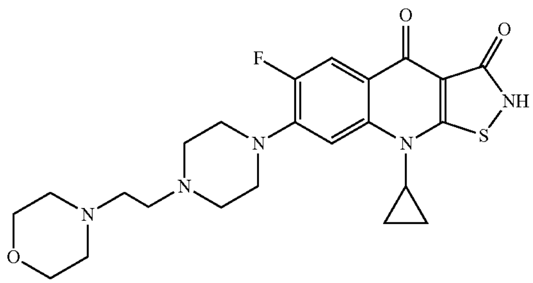 | 9-cyclopropyl-6-fluoro-7-(4-(2-morpholinoethyl)piperazin-1-yl)isothiazolo[5,4-b]quinoline-3,4(2H,9H)-dione | | 473.6 | | |
| 34 | 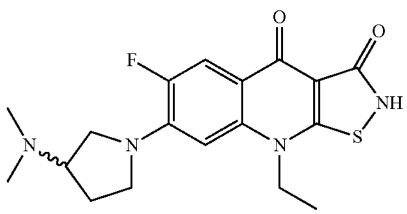 | 7-(3-(dimethylamino)pyrrolidin-1-yl)-9-ethyl-6-fluoroisothiazolo[5,4-b]quinoline-3,4(2H,9H)-dione | | 376.4 | | |
| 35 | 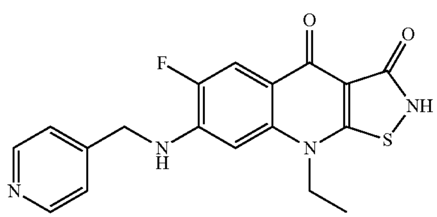 | 9-ethyl-6-fluoro-7-(pyridin-4-ylmethylamino)isothiazolo[5,4-b]quinoline-3,4(2H,9H)-dione | | 370.4 | | |
| 36 | 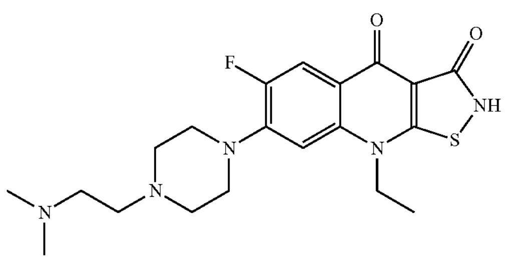 | 7-(4-(2-(dimethylamino)ethyl)piperazin-1-yl)-9-ethyl-6-fluoroisothiazolo[5,4-b]quinoline-3,4(2H,9H)-dione | | 419.5 | | |

TABLE II-continued

| No. | Structure | Name | Salt | MW | MS | H-NMR | F-NMR |
|---|---|---|---|---|---|---|---|
| 37 | 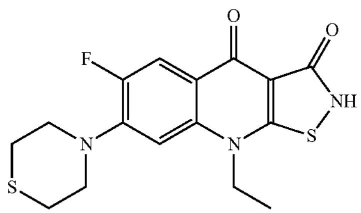 | 9-ethyl-6-fluoro-7-thiomorpholinoisothiazolo[5,4-b]quinoline-3,4(2H,9H)-dione | | 365.4 | | | |
| 38 | 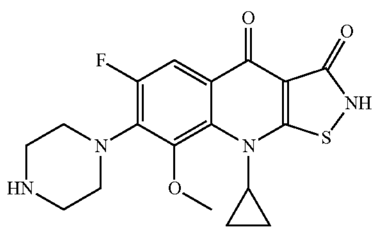 | 9-cyclopropyl-6-fluoro-8-methoxy-7-(piperazin-1-yl)isothiazolo[5,4-b]quinoline-3,4(2H,9H)-dione | | 390.4 | | | |
| 39 | 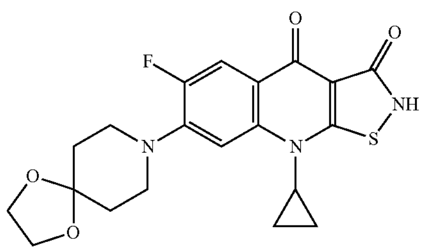 | | | 417.5 | | | |
| 40 | 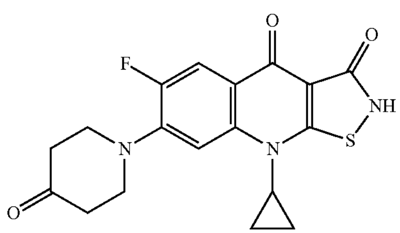 | 9-cyclopropyl-6-fluoro-7-(4-oxopiperidin-1-yl)isothiazolo[5,4-b]quinoline-3,4(2H,9H)-dione | | 373.4 | | | |

TABLE II-continued

| No. | Structure | Name | Salt | MW | MS | H-NMR | F-NMR |
|---|---|---|---|---|---|---|---|
| 41 | 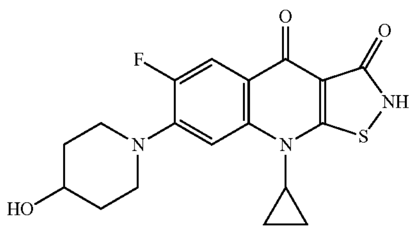 | 9-cyclopropyl-6-fluoro-7-(4-hydroxy-piperidin-1-yl)isothiazolo[5,4-b]quinoline-3,4(2H,9H)-dione | | 375.4 | | | |
| 42 | 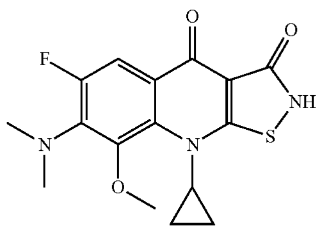 | 9-cyclopropyl-7-(dimethyl-amino)-6-fluoro-8-methoxyisothiazolo[5,4-b]quinoline-3,4(2H,9H)-dione | | 349.4 | | | |
| 43 | 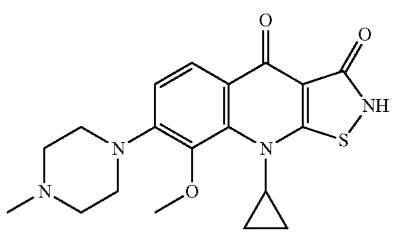 | 9-cyclopropyl-8-methoxy-7-(4-methyl-piperazin-1-yl)isothiazolo[5,4-b]quinoline-3,4(2H,9H)-dione | | 386.5 | | | |
| 44 | 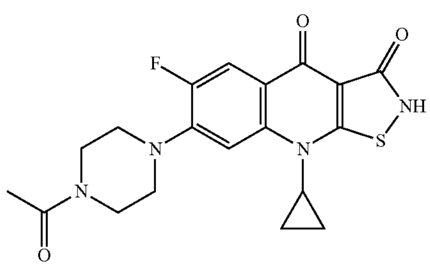 | 7-(4-acetyl-piperazin-1-yl)-9-cyclopropyl-6-fluoroisothiazolo[5,4-b]quinoline-3,4(2H,9H)-dione | | 402.4 | | | |

TABLE II-continued

| No. | Structure | Name | Salt | MW | MS | H-NMR | F-NMR |
|---|---|---|---|---|---|---|---|
| 45 | 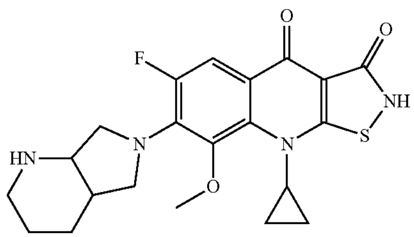 | 9-cyclopropyl-6-fluoro-8-methoxy-7-(octahydro-pyrrolo[3,4-b]pyridin-6-yl)isothia-zolo[5,4-b]quinoline-3,4(2H,9H)-dione | HCl | 430.5 | LCMS m/z calcd for $C_{21}H_{23}FN_4O_3S$ 430 ([M+]); found 431 ([M + H]+) | 1H NMR (300 MHz, DMSO-d6): δ 1.03 (m, 4H), 1.69 (m, 4H), 2.61 (m, 1H), 2.94 (m, 1H), 3.21 (m, 2H), 3.51 (s, 3H), 3.79 (m, 4H), 4.02 (m, 1H), 7.55 (d, J=15.1 Hz, 1H), 8.56 {s (br), 1H}, 9.48 {s (br), 1H} | 19F {1H} NMR (282 MHz, CDCl3): δ −125.8 (s, 1F) |
| 46 | 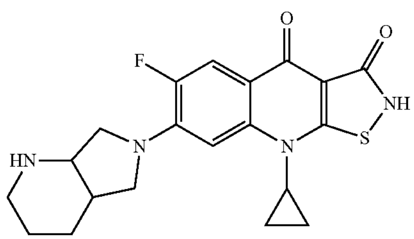 | 9-cyclopropyl-6-fluoro-7-(octahydro-pyrrolo[3,4-b]pyridin-6-yl)isothia-zolo[5,4-b]quinoline-3,4(2H,9H)-dione | HCl | 400.5 | LCMS m/z calcd for $C_{20}H_{21}FN_4O_2S$ 400 ([M+]); found 401 ([M + H]+) | 1H NMR (300 MHz, MeOH-d4): δ 1.22 (m, 4H), 1.81 (m, 4H), 2.89 (m, 3H), 3.20 (m, 1H), 3.63 (m, 2H), 3.89 (m, 3H), 6.75 {s (br), 1H}, 7.44 (d, J=14.0 Hz, 1H) | 19F {1H} NMR (282 MHz, CDCl3): δ −132.2 (s, 1F) |
| 47 | 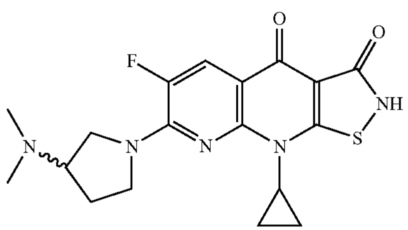 | 9-cyclopropyl-7-(3-(dimethyl-amino)pyrrolidin-1-yl)-6-fluoroiso-thiazolo[5,4-b][1,8]naph-thyridine-3,4(2H,9H)-dione | | 389.4 | | | |
| 48 | 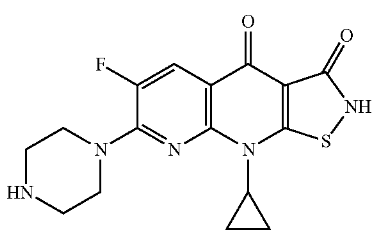 | 9-cyclopropyl-6-fluoro-7-(piperazin-1-yl)isothia-zolo[5,4-b][1,8]naph-thyridine-3,4(2H,9H)-dione | | 361.4 | | | |

TABLE II-continued

| No. | Structure | Name | Salt | MW | MS | H-NMR | F-NMR |
|---|---|---|---|---|---|---|---|
| 49 | 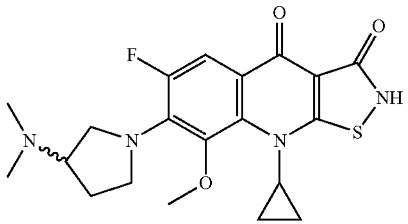 | 9-cyclopropyl-7-(3-(dimethyl-amino)pyrrolidin-1-yl)-6-fluoro-8-methoxy-isothiazolo[5,4-b]quinoline-3,4(2H,9H)-dione | | 418.5 | | | |
| 50 | 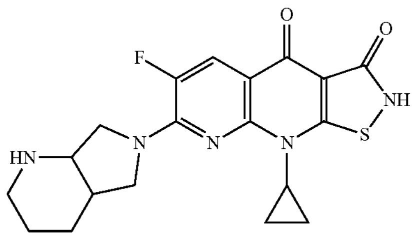 | 9-cyclopropyl-6-fluoro-7-(octahydro-pyrrolo[3,4-b]pyridin-6-yl)isothia-zolo[5,4-b][1,8]naph-thyridine-3,4(2H,9H)-dione | | | LCMS m/z calcd for $C_{19}H_{20}FN_5O_2S$ 401 ([M$^+$]); found 402 ([M + H]$^+$). | $^1$H NMR (300 MHz, DMSO-d$_6$): (selected data) δ 7.58 (br, aromatic | $^{19}F${$^1$H} NMR (282 MHz, DMSO-d$_6$): δ −140.5 (br). |
| 51 | 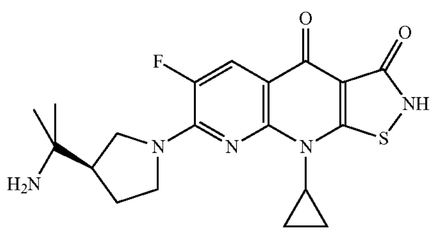 | (R)-7-(3-(2-aminopropan-2-yl)pyrrolidin-1-yl)-9-cyclopropyl-6-fluoroisothia-zolo[5,4-b][1,8]naph-thyridine-3,4(2H,9H)-dione | | | LCMS m/z calcd for $C_{19}H_{22}FN_5O_2S$ 403 ([M$^+$]); found 404 ([M + H]$^+$). | $^1$H NMR (300 MHz, DMSO-d$_6$)/acetic acid-d$_4$ (~10:1 v/v): δ 1.11 (m, 2H), 1.20 (m, 2H), 1.28 (s, 6H), 1.82 (m, 1H), 2.02 (m, 1H), 2.48 (m, 1H), 3.27 (m, 1H), 3.51 (m, 1H), 3.64 (m, 1H), 3.93 (m, 2H), 7.82 (d, $J_{H-F}$=13.0 Hz, 1H). | $^{19}F${$^1$H} NMR (282 MHz, DMSO-d$_6$)/acetic acid-d$_4$ (~10:1 v/v): δ −139.8 (s). |
| 52 | 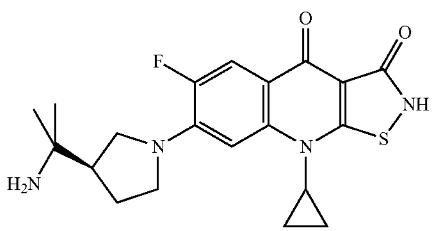 | (R)-7-(3-(2-aminopropan-2-yl)pyrrolidin-1-yl)-9-cyclopropyl-6-fluoroisothia-zolo[5,4-b]quinoline-3,4(2H,9H)-dione | | | LCMS m/z calcd for $C_{20}H_{23}FN_4O_2S$ 402 ([M$^+$]); found 403 ([M + H]$^+$). | $^1$H NMR (300 MHz, DMSO-d$_6$)/acetic acid-d$_4$ (~10:1 v/v): δ 1.15 (m, 2H), 1.30 (s, 6H), 1.33 (m, 2H), 1.84 (m, 1H), 2.04 (m, 1H), 2.54 (m, 1H), 3.32-3.71 (m, 5H), 6.89 (d, $J_{H-F}$=7.5 Hz, 1H), 7.60 (d, $J_{H-F}$=14.0 Hz, 1H). | $^{19}F${$^1$H} NMR (282 MHz, DMSO-d$_6$)/acetic acid-d$_4$ (~10:1 v/v): δ −131.8 (s). |

TABLE II-continued

| No. | Structure | Name | Salt | MW | MS | H-NMR | F-NMR |
|---|---|---|---|---|---|---|---|
| 53 | 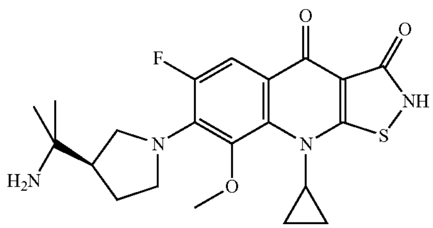 | (R)-7-(3-(2-aminopropan-2-yl)pyrrolidin-1-yl)-9-cyclopropyl-6-fluoro-8-methoxyisothiazolo[5,4-b]quinoline-3,4(2H,9H)-dione | | | LCMS m/z calcd for C₂₁H₂₅FN₄O₃S 432 ([M⁺]); found 433 ([M + H]⁺). | ¹H NMR (300 MHz, TFA-d): δ 1.28 (m, 2H), 1.53 (m, 2H), 1.66 (s, 6H), 2.43 (m, 1H), 2.57 (m, 1H), 3.35 (m, 1H), 3.97 (s, 3H), 4.01-4.38 (m, 5H), 8.17 (d, J=12.0 Hz, 1H, aromatic). | ¹⁹F{¹H} (282 MHz, acetic acid-d₄): δ −120.6 (s). |
| 54 | 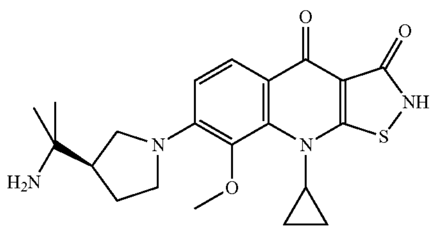 | (R)-7-(3-(2-aminopropan-2-yl)pyrrolidin-1-yl)-9-cyclopropyl-8-methoxyisothiazolo[5,4-b]quinoline-3,4(2H,9H)-dione | | | LCMS m/z calcd for C₂₁H₂₆N₄O₃S 414 ([M⁺]); found 415 ([M + H]⁺). | ¹H NMR (300 MHz, DMSO-d₆): δ 0.92 (m, 2H), 1.34 (m, 2H), 1.33 (s, 6H), 1.84 (m, 1H), 2.05 (m, 1H), 2.55 (m, 1H), 3.44 (m, 2H), 3.49 (s, 3H), 3.55 (m, 2H), 3.78 (m, 1H), 6.86 (d, J=9.0 Hz, 1H), 7.82 (d, J=9.0 Hz, 1H). | |
| 55 | 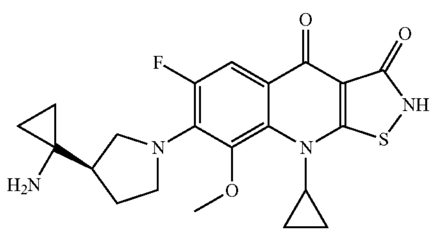 | (R)-7-(3-(1-aminocyclopropyl)pyrrolidin-1-yl)-9-cyclopropyl-6-fluoro-8-methoxyisothiazolo[5,4-b]quinoline-3,4(2H,9H)-dione | HCl | 430.5 | LCMS m/z calcd for C₂₁H₂₃FN₄O₃S 430 ([M⁺]); found 431 ([M + H]⁺, 100%). | ¹H—NMR (300 MHz, CD₃OD): δ 1.004-1.040 (m, 6H), 1.247-1.269 (m, 2H), 1.668-1.805 (m, 1H), 2.126-2.201 (m, 1H), 2.560-2.829 (m, 1H), 3.596-3.889 (s, 3H), 3.596 (m, 5H), 7.689 (d, J=14.1 Hz, 1H) | ¹⁹F (CD₃OD): δ −126.17 |
| 56 | 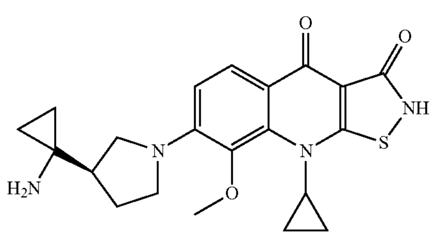 | (R)-7-(3-(1-aminocyclopropyl)pyrrolidin-1-yl)-9-cyclopropyl-8-methoxyisothiazolo[5,4-b]quinoline-3,4(2H,9H)-dione | HCl | 412.5 | LCMS m/z calcd for C₂₁H₂₄N₄O₃S 412 ([M⁺]); found 413 ([M + H]⁺, 100%). | ¹H-NMR (300 MHz, CD₃OD): δ 0.706-0.944 (m, 6H), 1.148-1.221 (m, 2H), 1.620-1.757 (m, 1H), 2.081-2.226 (m, 1H), 2.592-2.742 (m, 1H), 3.322 (t, J=9.9 Hz, 1H), 3.476 (s, 3H), 3.526-3.672 (m, 3H), 3.769-3.839 (m, 1H), 6.912 (d, J=8.7 Hz, 1H), 7.909 (d, J=9.0 Hz, 1H) | |

| No. | Structure | Name | Salt | MW | MS | H-NMR | F-NMR |
|---|---|---|---|---|---|---|---|
| 57 | 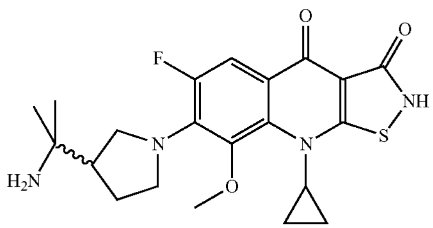 | 7-(3-(2-aminopropan-2-yl)pyrrolidin-1-yl)-9-cyclopropyl-6-fluoro-8-methoxyisothiazolo[5,4-b]quinoline-3,4(2H,9H)-dione | HCl | 432.5 | LCMS (APCI): m/z calcd for $C_{21}H_{25}FN_4O_3S$ ([M]⁺) 432; found 433 ([M + H]⁺) | (DMSO-D₆): δ 0.922-0.976 (2H, m), 1.116-1.188 (2H, m), 1.328 (6H, d, J=3.0 Hz), 1.744-1.882 (1H, m), 2.035-2.087 (1H, m), 2.511-2.572 (1H, m), 3.479-3.827 (5H, m), 3.541 (3H, s), 7.565 (1H, d, J=13.8 Hz), 8.249 (2H, brs) | (DMSO-d₆): −125.15 |
| 58 | 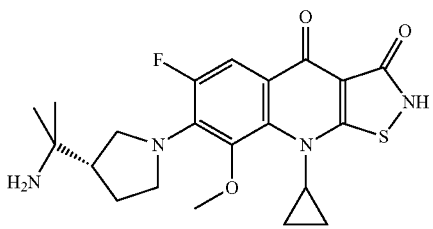 | (S)-7-(3-(2-aminopropan-2-yl)pyrrolidin-1-yl)-9-cyclopropyl-6-fluoro-8-methoxyisothiazolo[5,4-b]quinoline-3,4(2H,9H)-dione | | 432.5 | LCMS (APCI): m/z calcd for $C_{21}H_{25}FN_4O_3S$ ([M]⁺) 432; found 434 ([M + H]⁺) | ¹H NMR (CD₃CO₂D-d₄): δ 1.0 (m, 2H), 1.16 (m, 2H), 1.40 (m, 6H), 1.80 (m, 1H), 2.10 (m, 1H), 2.61 (m, 1H), 3.51 (s, 3H), 3.47-3.86 (m, 5H), 7.66 (d, J=14.2 Hz, 1H), 11.50 | ¹⁹F NMR (CD₃CO₂D-d₄) δ −124.57 (s, 1F) |
| 59 | 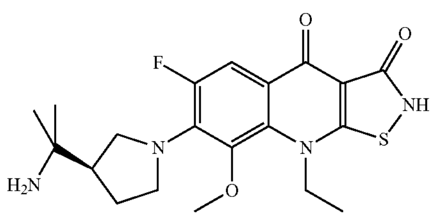 | (R)-7-(3-(2-aminopropan-2-yl)pyrrolidin-1-yl)-9-ethyl-6-fluoro-8-methoxyisothiazolo[5,4-b]quinoline-3,4(2H,9H)-dione | TFA | 420.5 | LCMS (APCI): m/z calcd for $C_{20}H_{25}FN_4O_3S$ ([M]⁺) 420; found 421 ([M + H]⁺) | ¹H NMR (DMSO-d₆): δ 1.24 (m, 9H), 1.86 (m, 2H), 3.42 (m, 4H), 3.54 (s, 3H), 3.66 (m, 1H), 4.09 (m, 1H), 4.44 (m, 1H), 7.60 (d, J=14.2 Hz, 1H), 7.88 (s (br), 1H) | ¹⁹F NMR (DMSO-d₆): δ −124.49 (s, 1F), −73.53 (s, 1F) |
| 60 | 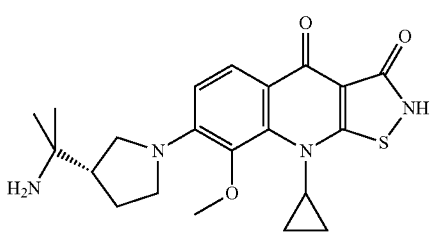 | (S)-7-(3-(2-aminopropan-2-yl)pyrrolidin-1-yl)-9-cyclopropyl-8-methoxyisothiazolo[5,4-b]quinoline-3,4(2H,9H)-dione | | 414.5 | LCMS (APCI): m/z calcd for $C_{21}H_{26}N_4O_3S$ ([M]⁺) 414; found 415 ([M + H]⁺) | ¹H NMR (DMSO-d₆): δ 0.94 (m, 2H), 1.14 (m, 2H), 1.33 (m, 6H), 1.85 (m, 1H), 2.05 (m, 1H), 2.54 (m, 1H), 3.44 (m, 2H), 3.49 (s, 3H), 3.56 (m, 2H), 3.79 (m, 1H), 4.25 (bs, 1H), 6.88 (d, J=9.1 Hz, 1H) 7.84 (d, J=9.1 Hz, 1H), 8.21 (m, 2H) | |

TABLE II-continued

| No. | Structure | Name | Salt | MW | MS | H-NMR | F-NMR |
|---|---|---|---|---|---|---|---|
| 61 | 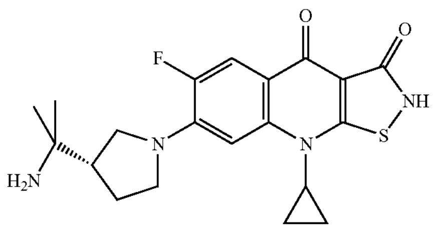 | (S)-7-(3-(2-aminopropan-2-yl)pyrrolidin-1-yl)-9-cyclopropyl-6-fluoroisothiazolo[5,4-b]quinoline-3,4(2H,9H)-dione | | 402.5 | LCMS (APCI): m/z calcd for $C_{20}H_{23}FN_4O_2S$ ([M]$^+$) 402; found 403 ([M + H]$^+$) | $^1$H NMR (DMSO-d$_6$ +DCl) 1.10 (m, 2H), 1.24 (m, 3H), 1.85 (m, 1H), 2.27 (m, 1H), 3.29-3.92 (m, 5H), 7.36 (d, J=14.3 Hz, 1H) 7.69 (d, J=14.6 Hz, 1H), 8.5 (m, 1H) | $^{19}$F NMR (DMSO-d$_6$ +DCl) δ −130.20 (s, 1F), −126.80 (s, 1F) |
| 62 | 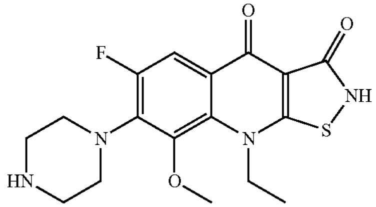 | 9-ethyl-6-fluoro-8-methoxy-7-(piperazin-1-yl)isothiazolo[5,4-b]quinoline-3,4(2H,9H)-dione | TFA | 378.4 | LCMS (APCI): m/z calcd for $C_{17}H_{19}FN_4O_3S$ ([M]$^+$) 378; found 379 ([M + H]$^+$) | $^1$H NMR (DMSO-d$_6$): δ 1.33 (t, J=6.8 Hz 3H), 3.39 (m, 8H), 3.84 (s, 3H), 4.34 (m, 2H), 7.76 (d, J=12.7 Hz, 1H), 8.13 (s, br), 1H) | $^{19}$F NMR (DMSO-d$_6$): δ −124.22 (s, 1F), −73.53 (s, 1F) |
| 63 | 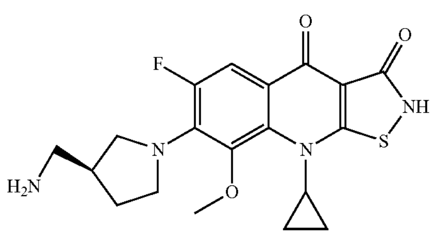 | (S)-7-(3-(aminomethyl)-pyrrolidin-1-yl)-9-cyclopropyl-6-fluoro-8-methoxy-isothiazolo[5,4-b]quinoline-3,4(2H,9H)-dione | HCl | 404.5 | LCMS m/z calcd for $C_{19}H_{21}FN_4O_3S$ 404 ([M$^+$]); found 405 ([M + H]$^+$, 100%). | (D$_2$O): δ 0.946-1.045 (2H, m), 1.161-1.25 (2H, m), 1.669-1.821 (1H, m), 2.143-2.268 (1H, m), 2.571-2.669 (1H, m), 3.063-3.179 (2H, m), 3.472-3.872 (8H, m), 7.285 (1H, d, J=15 Hz) | $^{19}$F (D$_2$O): δ −123.87 |
| 64 | 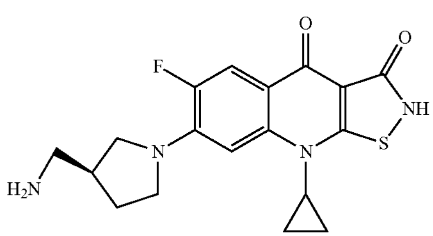 | (S)-7-(3-(aminomethyl)-pyrrolidin-1-yl)-9-cyclopropyl-6-fluoroisothiazolo[5,4-b]quinoline-3,4(2H,9H)-dione | HCl | 374.4 | LCMS m/z calcd for $C_{18}H_{19}FN_4O_2S$ 374 ([M$^+$]); found 375 ([M + H]$^+$, 100%). | (D$_2$O): δ 1.060-1.164 (2H, m), 1.224-1.353 (2H, m), 1.720-1.843 (1H, m), 2.254-2.345 (1H, m), 2.60-2.729 (1H, m), 2.985-3.187 (4H, m), 3.435-3.643 (3H, m), 6.386 (1H, d, J=7.2 Hz), 7.113 (1H, d, J=15.9 Hz) | $^{19}$F (D$_2$O): δ −130.10 |

| No. | Structure | Name | Salt | MW | MS | H-NMR | F-NMR |
|---|---|---|---|---|---|---|---|
| 65 | 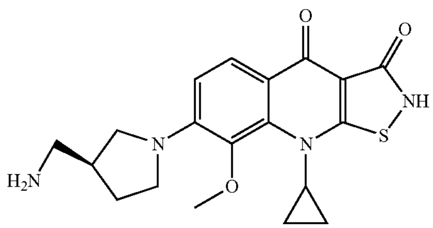 | (S)-7-(3-(aminomethyl)-pyrrolidin-1-yl)-9-cyclopropyl-8-methoxyiso-thiazolo[5,4-b]quinoline-3,4(2H,9H)-dione | HCl | 386.5 | LCMS m/z calcd for C₁₉H₂₂N₄O₃S 386 ([M⁺]); found 387 ([M + H]⁺, 100%). | (DMSO-D₆): δ 0.833-0.979 (2H, m), 1.114-1.196 (2H, m), 1.760-1.828 (1H, m), 2.133-2.191 (1H, m), 2.527-2.630 (1H, m), 2.891-3.0 (2H, m), 3.302 (1H, dd, J=3, 7.5 Hz), 3.493 (3H, s), 3.531-3.831 (4H, m), 6.842 (1H, d, J=9 Hz), 7.839 (1H, d, J=9 Hz), 8.092 (2H, brs) | |
| 66 | 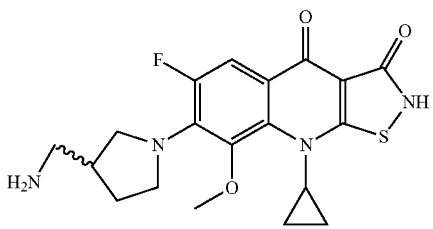 | 7-(3-(aminomethyl)-pyrrolidin-1-yl)-9-cyclopropyl-6-fluoro-8-methoxyiso-thiazolo[5,4-b]quinoline-3,4(2H,9H)-dione | HCl | 404.5 | LCMS m/z calcd for C₁₉H₂₁FN₄O₃S 404 ([M⁺]); found 405 ([M + H]⁺, 100%). | (DMSO-D₆ + DCl): δ0.926-0.954 (2H, m), 1.156-1.203 (2H, m), 1.767-1.833 (1H, m), 2.132-2.192 (1H, m), 2.589-2.636 (1H, m), 3.449-3.507 (1H, m), 3.533 (3H, s), 3.613-3.825 (4H, m), 7.567 (1H, d, J=13.8 Hz) | |
| 67 | 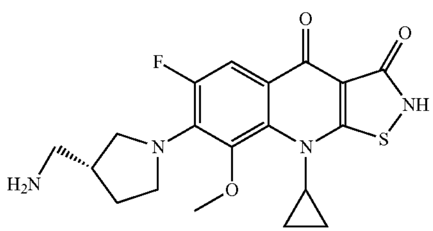 | (R)-7-(3-(aminomethyl)-pyrrolidin-1-yl)-9-cyclopropyl-6-fluoro-8-methoxyiso-thiazolo[5,4-b]quinoline-3,4(2H,9H)-dione | HCl | 404.5 | LCMS m/z calcd for C₁₉H₂₁FN₄O₃S 404 ([M⁺]); found 405 ([M + H]⁺, 100%). | (D₂O): δ 0.838-1.013 (2H, m), 1.063-1.225 (2H, m), 1.575-1.750 (1H, m), 2.063-2.20 (1H, m), 2.444-2.613 (1H, m), 2.992-3.133 (2H, m), 3.385 (3H, s), 3.3055-3.711 (5H, m), 7.193 (1H, d, J=14.1 Hz) | |
| 68 | 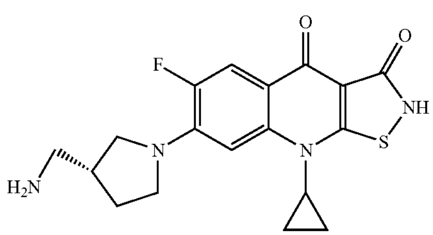 | (R)-7-(3-(aminomethyl)-pyrrolidin-1-yl)-9-cyclopropyl-6-fluoroiso-thiazolo[5,4-b]quinoline-3,4(2H,9H)-dione | HCl | 374.4 | LCMS m/z calcd for C₁₈H₁₉FN₄O₂S 374 ([M⁺]); found 375 ([M + H]⁺, 100%). | (DMSO-D₆): δ 1.150-1.214 (2H, m), 1.367-1.383 (2H, m), 1.780-1.910 (1H, m), 2.158-2.286 (1H, m), 2.571-2.666 (1H, m), 2.951-2.991 (3H, m), 3.478-3.821 (4H, m), 6.972 (1H, d, J=7.5 Hz), 7.702 (1H, d, J=15.6 Hz), 8.147 (2H, br) | ¹⁹F (DMSO-d₆): δ -131.69 |

TABLE II-continued

| No. | Structure | Name | Salt | MW | MS | H-NMR | F-NMR |
|---|---|---|---|---|---|---|---|
| 69 | 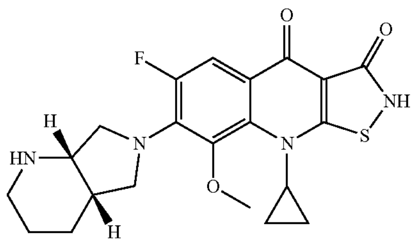 | 9-cyclopropyl-6-fluoro-8-methoxy-7-((4aS,7aS)-octahydropyrrolo[3,4-b]pyridin-6-yl)isothiazolo[5,4-b]quinoline-3,4(2H,9H)-dione | | | LCMS m/z calcd for C$_{21}$H$_{23}$FN$_4$O$_3$S 430 ([M$^+$]); found 431 ([M + H]$^+$, 100%). | $^1$H NMR (DMSO-d6): δ 0.86 (br, 2H), 1.06 (m, 2H), 1.37 (m, 1H), 1.61 (m, 4H) 2.19 (m, 2H), 2.38 (m, 2H), 3.45 (s, 3H), 3.69 (m, 1H), 3.83 (m, 3H) 7.44 (d, J=16.6 Hz, 1H) | $^{19}$F (DMSO-d$_6$): δ −126.05 |
| 70 | 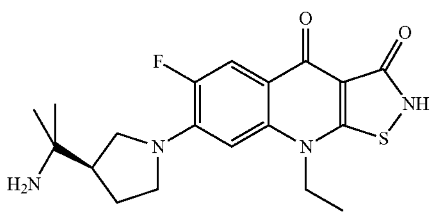 | (R)-7-(3-(2-aminopropan-2-yl)pyrrolidin-1-yl)-9-ethyl-6-fluoroisothiazolo[5,4-b]quinoline-3,4(2H,9H)-dione | HCl | 390.5 | LCMS m/z calcd for C$_{21}$H$_{23}$FN$_4$O$_3$S 430 ([M$^+$]); found 431 ([M + H]$^+$, 100%). | $^1$H NMR (DMSO-d6): δ 0.86 (br, 2H), 1.06 (m, 2H), 1.37 (m, 1H), 1.61 (m, 4H) 2.19 (m, 2H), 2.38 (m, 2H), 3.45 (s, 3H), 3.69 (m, 1H), 3.83 (m, 3H) 7.44 (d, J=16.6 Hz, 1H) | $^{19}$F (DMSO-d$_6$): δ −126.05 |
| 71 | 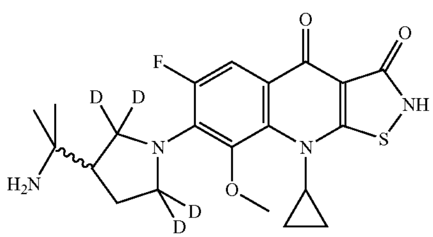 | 7-(3-(2-aminopropan-2-yl)-2,2,5,5-tetradeuterated-pyrrolidin-1-yl)-9-cyclopropyl-6-fluoro-8-methoxyisothiazolo[5,4-b]quinoline-3,4(2H,9H)-dione | | 436.5 | LCMS m/z calcd for C$_{21}$H$_{21}$D$_4$FN$_4$O$_3$S 436 ([M$^+$]); found 437 ([M + H]$^+$, 100%). | $^1$H NMR (CD$_3$CO$_2$D-d$_4$): δ 0.98 (m, 2H), 1.16 (m, 2H), 1.41 (s, 6H), 1.78 (m, 1H), 2.08 (m, 1H), 2.67 (m, 1H), 3.49 (s, 3H), 3.69 (m, 1H), 7.63 (d, J=14.4 Hz, 1H) | $^{19}$F (DMSO-d$_6$): δ −124.76 |
| 72 | 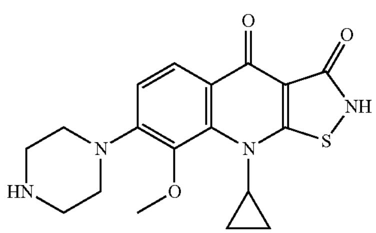 | 9-cyclopropyl-8-methoxy-7-(piperazin-1-yl)isothiazolo[5,4-b]quinoline-3,4(2H,9H)-dione | HCl | 372.4 | LCMS m/z calcd for C$_{21}$H$_{21}$D$_4$FN$_4$O$_3$S 436 ([M$^+$]); found 437 ([M + H]$^+$, 100%). | $^1$H NMR (CD$_3$CO$_2$D-d$_4$): δ 0.98 (m, 2H), 1.16 (m, 2H), 1.41 (s, 6H), 1.78 (m, 1H), 2.08 (m, 1H), 2.67 (m, 1H), 3.49 (s, 3H), 3.69 (m, 1H), 7.63 (d, J=14.4 Hz, 1H) | |

TABLE II-continued

| No. | Structure | Name | Salt | MW | MS | H-NMR | F-NMR |
|---|---|---|---|---|---|---|---|
| 73 | (structure) | (R)-7-(3-(1-aminoethyl)pyrrolidin-1-yl)-9-cyclopropyl-6-fluoro-8-methoxyisothiazolo[5,4-b]quinoline-3,4(2H,9H)-dione | HCl | 418.5 | LCMS (APCI): m/z calcd for $C_{20}H_{23}FN_4O_3S$ ([M]$^+$) 418; found 419 ([M + H]$^+$) | $^1$H NMR (DMSO-$d_6$) δ 8.23 (br, 1H), 8.20 (br, 1H), 7.56 (d, $J_{H-F}$=14.0 Hz, 1H), 6.20 (br, 2H), 3.82-3.50 (m, 3H), 3.60-3.45 (m, 2H), 3.52 (s, 3H, methoxy), 3.28 (m, 1H), 2.41 (m, 1H), 2.14 (m, 1H), 1.76 (m, 1H), 1.29 (d, J=6.5 Hz, 3H, methyl), 1.26 (d, J=6.5 Hz, 3H, methyl-epimer), 1.14 (m, 2H, c-Pr), 0.95 (m, 2H, c-Pr) | $^{19}$F NMR (DMSO-$d_6$) δ −125.4 (s, 1F), −125.5 (s, 1F, epimer) |
| 74 | (structure) | (R)-9-cyclopropyl-6-fluoro-8-methoxy-7-(3-(1-(methylamino)ethyl)pyrrolidin-1-yl)isothiazolo[5,4-b]quinoline-3,4(2H,9H)-dione | | 432.5 | LCMS (APCI): m/z calcd for $C_{21}H_{25}FN_4O_3S$ ([M]$^+$) 432; found 433 ([M + H]$^+$) | $^1$H NMR (DMSO-$d_6$) δ 9.08 (br, 1H), 8.89 (br, 1H), 7.55 (d, $J_{H-F}$=14.0 Hz, 1H), 6.30 (br, 1H), 3.81-3.64 (m, 3H), 3.55 (m, 2H), 3.52 (s, 3H, methoxy), 3.29 (m, 1H), 2.56 (s, 3H, —NMe), 2.55 (s, 3H, —NMe-epimer), 2.28-2.03 (m, 2H), 1.78 (m, 1H), 1.29 (d, J=6.6 Hz, 3H, methyl), 1.25 (d, J=6.6 Hz, 3H, methyl-epimer), 1.13 (m, 2H, c-Pr), 0.94 (m, 2H, c-Pr) | $^{19}$F NMR (DMSO-$d_6$) δ −125.4 (s, 1F) |
| 75 | (structure) | 7-(3-(2-aminopropan-2-yl)pyrrolidin-1-yl)-9-cyclopropyl-6,8-difluoroisothiazolo[5,4-b]quinoline-3,4(2H,9H)-dione | | 420.5 | LCMS (APCI): m/z calcd for $C_{20}H_{22}F_2N_4O_2S$ ([M]$^+$) 420; found 421 ([M + H]$^+$) | $^1$H NMR (DMSO-$d_6$): δ 1.17 (m, 2H), 1.34 (m, 6H), 1.43 (m, 2H), 1.88 (m, 1H), 2.00 (m, 1H), 2.64 (m, 1H), 3.42-3.76 (m, 5H), 4.91 (s, 2H), 7.00 (d, J=8.0 Hz, 1H) 7.69 (d, J=14.6 Hz, 1H), 8.5 (m, 1H) | $^{19}$F NMR (DMSO-$d_6$) δ −131.19 (s, 1F) |

TABLE II-continued

| No. | Structure | Name | Salt | MW | MS | H-NMR | F-NMR |
|---|---|---|---|---|---|---|---|
| 76 | 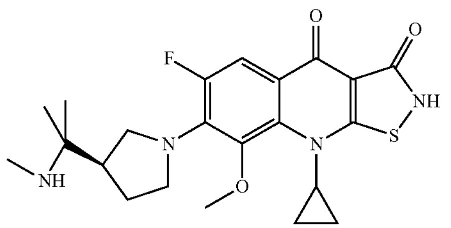 | (R)-9-cyclopropyl-6-fluoro-8-methoxy-7-(3-(2-(methylamino)propan-2-yl)pyrrolidin-1-yl)isothiazolo[5,4-b]quinoline-3,4(2H,9H)-dione | HCl | 446.5 | LCMS (APCI): m/z calcd for $C_{22}H_{27}FN_4O_3S$ [M]$^+$ 446; found 447 ([M + H]$^+$) | $^1$H NMR (DMSO-$d_6$) δ 0.93 (m, 2H), 1.34 (m, 2H), 1.29 (s, 3H), 1.32 (s, 3H), 1.81 (m, 1H), 2.04 (m, 1H), 2.47 (s, 3H), 2.63 (m, 1H), 3.54 (m, 2H), 3.54 (s, 3H), 3.61 (m, 1H), 3.77 (m, 3H), 7.55 (d, J=13.8 Hz, 1H), 8.93 (s(br), 1H) | $^{19}$F NMR (DMSO-$d_6$) δ −125.16 (s, 1F) |
| 77 | 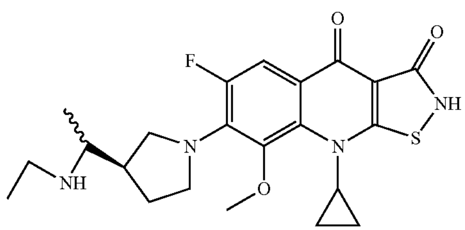 | (R)-9-cyclopropyl-7-(3-(1-(ethylamino)ethyl)pyrrolidin-1-yl)-6-fluoro-8-methoxyisothiazolo[5,4-b]quinoline-3,4(2H,9H)-dione | HCl | 446.5 | LCMS (APCI): m/z calcd for $C_{22}H_{27}FN_4O_3S$ [M]$^+$ 446; found 447 ([M + H]$^+$) | $^1$H NMR (DMSO-$d_6$) δ 9.04 (br, 1H), 8.73 (br, 1H), 7.56 (d, $J_{H,F}$=14.0 Hz, 1H), 6.52 (br, 1H), 3.81-3.68 (m, 3H), 3.56 (m, 2H), 3.52 (s, 3H, methoxy), 3.34 (m, 1H), 3.03-2.96 (m, 2H), 2.59 (m, 1H), 2.26-2.04 (m, 1H), 1.79 (m, 1H), 1.33-1.19 (m, 6H), 1.13 (m, 2H, c-Pr), 0.94 (m, 2H, c-Pr) | $^{19}$F NMR (DMSO-$d_6$) δ −125.3 (s, 1F), −125.4 (s, 1F, epimer) |
| 78 | 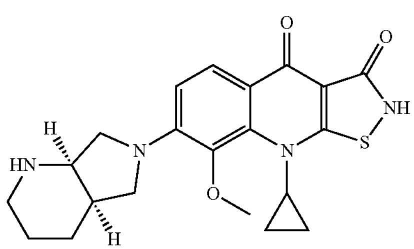 | 9-cyclopropyl-8-methoxy-7-((4aR,7aR)-octahydropyrrolo[3,4-b]pyridin-6-yl)isothiazolo[5,4-b]quinoline-3,4(2H,9H)-dione | | 412.5 | | | |
| 79 | 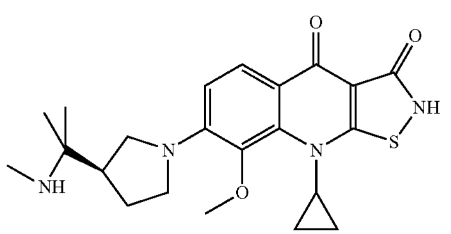 | (R)-9-cyclopropyl-8-methoxy-7-(3-(2-(methylamino)propan-2-yl)pyrrolidin-1-yl)isothiazolo[5,4-b]quinoline-3,4(2H,9H)-dione | HCl | 428.5 | LCMS (APCI): m/z calcd for $C_{22}H_{28}N_4O_3S$ [M]$^+$ 428; found 429 ([M + H]$^+$) | $^1$H NMR (DMSO-$d_6$) δ 0.93 (m, 2H), 1.16 (m, 2H), 1.34 (s, 6H), 1.83 (m, 1H), 2.06 (m, 2H), 2.50 (s, 3H), 2.64 (m, 1H), 3.46 (m, 4H), 3.49 (s, 3H) 3.79 (m, 1H), 6.87 (d, J=8.0 Hz, 1H), 7.83 (d, J=8.0 Hz, 1H), 8.99 (s(br), 1H) | |

TABLE II-continued

| No. | Structure | Name | Salt | MW | MS | H-NMR | F-NMR |
|---|---|---|---|---|---|---|---|
| 80 | 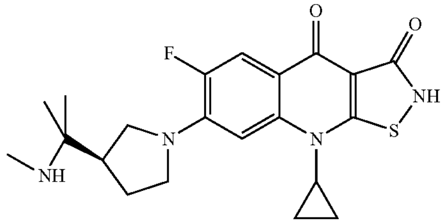 | (R)-9-cyclopropyl-6-fluoro-7-(3-(2-(methylamino)propan-2-yl)-pyrrolidin-1-yl)isothiazolo[5,4-b]quinoline-3,4(2H,9H)-dione | HCl | 416.5 | LCMS (APCI): m/z calcd for $C_{21}H_{25}FN_4O_2S$ ([M]⁺) 416; found 417 ([M + H]⁺) | ¹H NMR (DMSO-d₆): δ 1.19 (m, 2H), 1.33 (s, 6H), 1.44 (m, 2H) 1.88 (m, 1H), 2.09 (m, 1H), 2.51 (s, 3H), 2.72 (m, 1H), 3.57 (m, 5H), 7.01 (d, J=7.9 Hz, 1H), 7.71 (d, J=14.5 Hz, 1H), 9.11 (s(br), 1H) | ¹⁹F NMR (DMSO-d₆) δ −131.38 (s, 1F) |
| 81 | 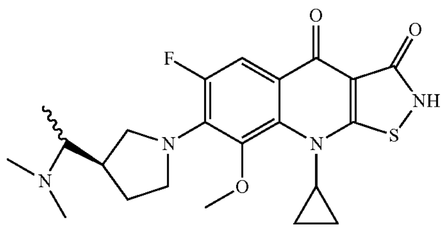 | (R)-9-cyclopropyl-7-(3-(1-(dimethylamino)ethyl)pyrrolidin-1-yl)-6-fluoro-8-methoxyisothiazolo[5,4-b]quinoline-3,4(2H,9H)-dione | HCl | 446.5 | LCMS (APCI): m/z calcd for $C_{22}H_{27}FN_4O_3S$ ([M]⁺) 446; found 447 ([M + H]⁺) | ¹H NMR (DMSO-d₆) δ 10.17 (br, 1H), 7.55 (d, $J_{H-F}$=14.0 Hz, 1H), 3.82-3.70 (m, 3H), 3.70-3.44 (m, 3H), 3.52 (s, 3H, methoxy), 2.75 (m, 3H), 2.69 (m, 3H), 2.56 (m, 1H), 2.39-2.03 (m, 1H), 1.76 (m, 1H), 1.30 (d, J=6.7 Hz, 3H, methyl), 1.25 (d, J=6.7 Hz, 3H, methyl-epimer), 1.15 (m, 2H, c-Pr), 0.94 (m, 2H, c-Pr) | ¹⁹F NMR (DMSO-d₆) δ −125.4 (s, 1F), −125.5 (s, 1F, epimer) |
| 82 | 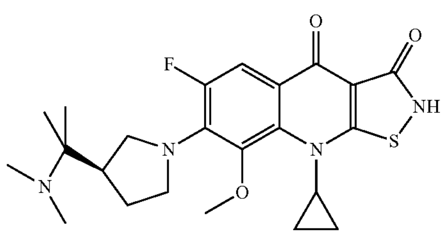 | (R)-9-cyclopropyl-7-(3-(2-(dimethylamino)propan-2-yl)pyrrolidin-1-yl)-6-fluoro-8-methoxyisothiazolo[5,4-b]quinoline-3,4(2H,9H)-dione | HCl | 460.6 | LCMS (APCI): m/z calcd for $C_{23}H_{29}FN_4O_3S$ ([M]⁺) 460; found 461 ([M + H]⁺) | ¹H NMR (DMSO-d₆): δ 0.88 (m, 2H), 1.09 (m, 2H), 1.34 (s, 3H), 1.37 (s, 3H), 1.76 (m, 1H), 2.04 (m, 1H), 2.69 (m, 7H), 3.49 (s, 3H), 3.62 (m, 5H), 7.56 (d, J=14.5 Hz, 1H | ¹⁹F NMR (DMSO-d₆) δ −125.18 (s, 1F) |

TABLE II-continued

| No. | Structure | Name | Salt | MW | MS | H-NMR | F-NMR |
|---|---|---|---|---|---|---|---|
| 83 | 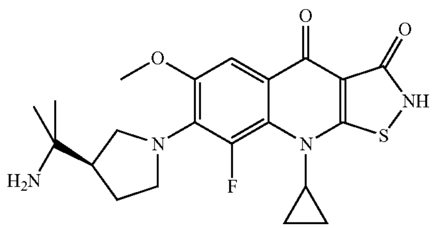 | (R)-7-(3-(2-aminopropan-2-yl)pyrrolidin-1-yl)-9-cyclopropyl-8-fluoro-6-methoxyisothiazolo[5,4-b]quinoline-3,4(2H,9H)-dione | HCl | 432.5 | LCMS (APCI): m/z calcd for $C_{21}H_{25}FN_4O_3S$ ([M]$^+$) 432; found 433 ([M + H]$^+$) | $^1$H NMR (DMSO-d$_6$): δ 1.04 (m, 2H), 1.13 (m, 2H), 1.24 (d, J=2.6 Hz, 6H), 1.71 (m, 1H), 1.92 (m, 1H), 3.32-3.49 (m, 2H), 3.55-3.77 (m, 3H), 3.82 (s, 3H), 7.35 (s, 1H), 8.12 (s(br), 1H) | $^{19}$F NMR (DMSO-d$_6$) δ −120.34 (s, 1F) |
| 84 | 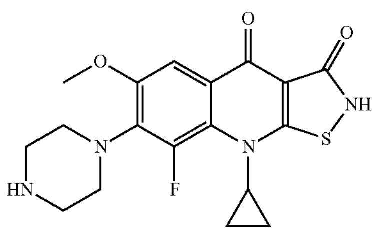 | 9-cyclopropyl-8-fluoro-6-methoxy-7-(piperazin-1-yl)isothiazolo[5,4-b]quinoline-3,4(2H,9H)-dione | HCl | 390.4 | LCMS (APCI): m/z calcd for $C_{18}H_{19}FN_4O_3S$ ([M]$^+$) 390; found 391 ([M + H]$^+$) | $^1$H NMR (DMSO-d$_6$): δ 1.15 (m, 4H), 3.20 (m, 8H), 3.79 (m, 1H), 3.90 (s, 3H), 7.47 (s, 1H), 9.08 (s(br), 1H) | $^{19}$F NMR (DMSO-d$_6$) δ −127.31 (s, 1F) |
| 85 | 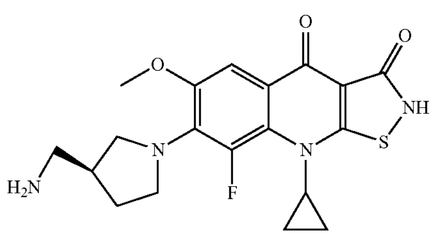 | (S)-7-(3-(aminomethyl)-pyrrolidin-1-yl)-9-cyclopropyl-8-fluoro-6-methoxyisothiazolo[5,4-b]quinoline-3,4(2H,9H)-dione | HCl | 404.5 | LCMS (APCI): m/z calcd for $C_{19}H_{21}FN_4O_3S$ ([M]$^+$) 404; found 405 ([M + H]$^+$) | $^1$H NMR (DMSO-d$_6$): δ 1.08 (m, 4H), 1.65 (m, 1H), 2.02 (m, 1H), 2.86 (m, 2H), 3.41 (m, 1H), 3.60 (m, 4H), 3.74 (m, 1H), 3.81 (s, 3H), 7.35 (s, 1H), 7.95 (s(br), 1H) | $^{19}$F NMR (DMSO-d$_6$) δ −129.70 (s, 1F) |
| 86 | 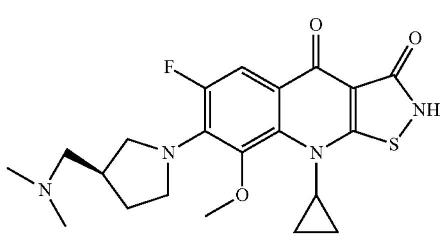 | (S)-9-cyclopropyl-7-(3-((dimethylamino)methyl)pyrrolidin-1-yl)-6-fluoro-8-methoxyisothiazolo[5,4-b]quinoline-3,4(2H,9H)-dione | HCl | 432.5 | LCMS (APCI): m/z calcd for $C_{21}H_{25}FN_4O_3S$ ([M]$^+$) 432; found 433 ([M + H]$^+$) | $^1$H NMR (DMSO-d$_6$): δ 0.89 (m, 2H), 1.07 (m, 2H), 1.71 (m, 1H), 2.18 (m, 1H), 2.74 (m, 4H), 3.17 (t, J=6.3 Hz, 1H), 3.48 (m, 7H), 3.71 (m, 5H), 7.50 (d, J=14.2 Hz, 1H) | $^{19}$F NMR (DMSO-d$_6$) δ −125.69 (s, 1F) |

TABLE II-continued

| No. | Structure | Name | Salt | MW | MS | H-NMR | F-NMR |
|---|---|---|---|---|---|---|---|
| 87 | 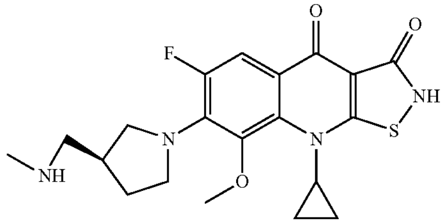 | (S)-9-cyclopropyl-6-fluoro-8-methoxy-7-(3-((methylamino)methyl)pyrrolidin-1-yl)isothiazolo[5,4-b]quinoline-3,4(2H,9H)-dione | HCl | 418.5 | LCMS (APCI): m/z calcd for $C_{20}H_{23}FN_4O_3S$ [M]$^+$ 418; found 419 ([M + H]$^+$) | $^1$H NMR (DMSO-$d_6$): δ 0.98 (m, 4H), 1.73 (m, 1H), 2.09 (m, 1H), 2.50 (s, 3H), 2.51 (t, J=5.2 Hz, 2H), 2.74 (m, 1H), 3.46 (s, 3H), 3.58 (m, 3H), 7.55 (d, J=13.2 Hz, 1H), 8.98 (s(br), 1H) | $^{19}$F NMR (DMSO-$d_6$) δ −125.57 (s, 1F) |
| 88 | 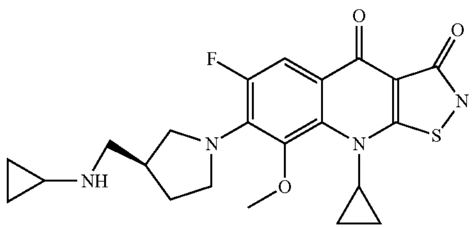 | (S)-9-cyclopropyl-7-(3-((cyclopropylamino)methyl)pyrrolidin-1-yl)-6-fluoro-8-methoxyisothiazolo[5,4-b]quinoline-3,4(2H,9H)-dione | HCl | 444.5 | LCMS (APCI): m/z calcd for $C_{22}H_{25}FN_4O_3S$ [M]$^+$ 444; found 445 ([M + H]$^+$) | $^1$H NMR (DMSO-$d_6$) δ 9.46 (br, 2H), 7.53 (d, $J_{H,F}$=14.0 Hz, 1H), 7.16 (br, 1H), 3.81-3.66 (m, 2H), 3.61 (m, 2H), 3.55 (s, 3H, methoxy), 3.52-3.42 (m, 1H), 3.13 (m, 2H), 2.70 (m, 2H), 2.16 (m, 1H), 1.80 (m, 1H), 1.13 (m, 2H, c-Pr), 0.96 (m, 4H, c-Pr), 0.73 (m, 2H, c-Pr) | $^{19}$F NMR (DMSO-$d_6$) δ −120.8 (s, 1F) |
| 89 | 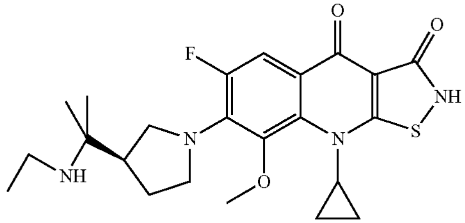 | (R)-9-cyclopropyl-7-(3-(2-(ethylamino)propan-2-yl)pyrrolidin-1-yl)-6-fluoro-8-methoxyisothiazolo[5,4-b]quinoline-3,4(2H,9H)-dione | HCl | 460.6 | LCMS (APCI): m/z calcd for $C_{23}H_{29}FN_4O_3S$ [M]$^+$ 460; found 461 ([M + H]$^+$) | $^1$H NMR (DMSO-d6): δ 0.94 (m, 2H), 1.14 (m, 1H), 1.27 (t, J=7.3 Hz, 3H), 1.33 (s, 3H), 1.36 (s, 3H), 1.81 (m, 1H), 2.05 (m, 1H), 2.65 (m, 1H), 2.99 (m, 2H), 3.53 (s, 3H), 3.61 (m, 5H), 7.55 (d, J=14.9 Hz, 1H), 8.75 (s(br), 1H) | $^{19}$F NMR (DMSO-$d_6$) δ −125.13 (s, 1F) |
| 90 | 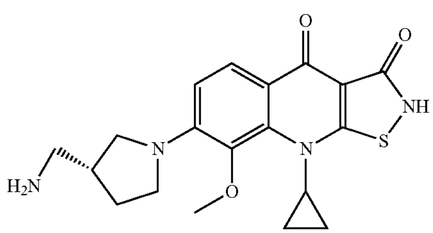 | (R)-7-(3-(aminomethyl)pyrrolidin-1-yl)-9-cyclopropyl-8-methoxyisothiazolo[5,4-b]quinoline-3,4(2H,9H)-dione | HCl | 386.5 | LCMS (APCI): m/z calcd for $C_{19}H_{22}N_4O_3S$ 386 ([M$^+$]); found 487 ([M + H]$^+$, 100%) | (CDCl$_3$): δ 0.929-0.979 (2H, m), 1.137-1.189 (2H, m), 1.758-1.850 (1H, m), 2.151-2.21 (1H, m), 2.527-2.594 (1H, m), 2.908-3.013 (3H, m), 3.271-3.831 (4H, m), 3.493 (3H, s), 6.843 (1H, d, J=9 Hz), 7.839 (1H, d, J=9 Hz). | |

TABLE II-continued

| No. | Structure | Name | Salt | MW | MS | H-NMR | F-NMR |
|---|---|---|---|---|---|---|---|
| 91 | 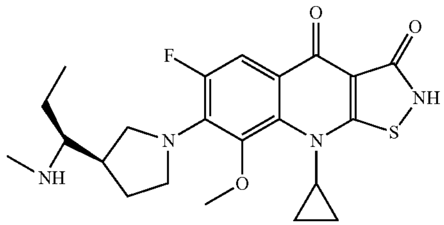 | 9-cyclopropyl-6-fluoro-8-methoxy-7-((R)-3-((S)-1-(methylamino)-propyl)pyrrolidin-1-yl)isothiazolo[5,4-b]quinoline-3,4(2H,9H)-dione | HCl | 446.5 | LCMS m/z calcd for $C_{22}H_{27}FN_4O_3S$ 446 ([M⁺]); found 447 ([M + H]⁺, 100%) | (CD₃OD): δ 0.835-0978 (2H, m), 1.019 (3H, t, J=7.5 Hz), 1.142-1.154 (2H, m), 1.710-1.935 (3H, m), 2.103-2.151 (1H, m), 2.475-2.615 (1H, m), 2.679 (3H, s), 3.496 (3H, s), 3.446-3.847 (6H, m), 7.543 (1H, d, J=14.4 Hz) | (CD₃OD): δ −125.97 |
| 92 | 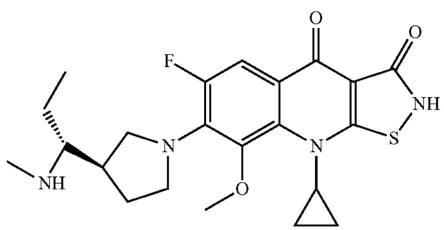 | 9-cyclopropyl-6-fluoro-8-methoxy-7-((R)-3-((R)-1-(methylamino)-propyl)pyrrolidin-1-yl)isothiazolo[5,4-b]quinoline-3,4(2H,9H)-dione | HCl | 446.5 | LCMS m/z calcd for $C_{22}H_{27}FN_4O_3S$ 446 ([M⁺]); found 447 ([M + H]⁺, 100%) | (CD₃OD): δ 0.875-0.980 (2H, m), 1.001 (3H, t, J=7.5 Hz), 1.118-1.211 (2H, m), 1.638-1.863 (3H, m), 2.151-2.237 (1H, m), 2.513-2.586 (1H, m), 2.689 (3H, s), 3.486-3.895 (6H, m), 7.567 (1H, d, J=14.1 Hz) | (CD₃OD): δ −126.21 |
| 93 | 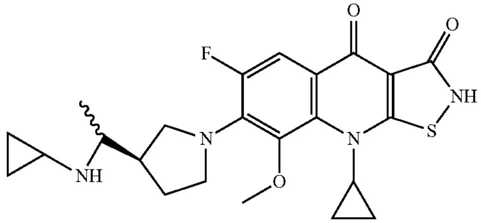 | (R)-9-cyclopropyl-7-(3-(1-(cyclopropylamino)ethyl)pyrrolidin-1-yl)-6-fluoro-8-methoxyisothiazolo[5,4-b]quinoline-3,4(2H,9H)-dione | HCl | 458.6 | LCMS (APCI) m/z calcd for $C_{23}H_{27}FN_4O_3S$ ([M]⁺) 458; found 459 ([M + H]⁺) | ¹H NMR (DMSO-d₆) δ 9.40 (br, 1H), 9.18 (br, 1H), 7.55 (d, $J_{H-F}$=14.0 Hz, 1H), 3.82-3.64 (m, 3H), 3.62-3.39 (m, 3H), 3.52 (s, 3H, methoxy), 2.70 (m, 2H), 2.31-2.05 (m, 1H), 1.81 (m, 1H), 1.38 (d, J=6.6 Hz, 3H, methyl), 1.35 (d, J=6.7 Hz, 3H, methyl-epimer), 1.17-0.75 (m, 8H, c-Pr) | ¹⁹F NMR (DMSO-d₆) δ −125.2 (s, 1F), −125.4 (s, 1F; epimer) |

| No. | Structure | Name | Salt | MW | MS | H-NMR | F-NMR |
|---|---|---|---|---|---|---|---|
| 94 | 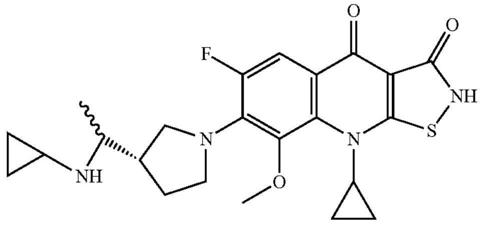 | (S)-9-cyclopropyl-7-(3-(1-(cyclopropylamino)ethyl))-pyrrolidin-1-yl)-6-fluoro-8-methoxyisothiazolo[5,4-b]quinoline-3,4(2H,9H)-dione | HCl | 458.6 | LCMS (APCI): m/z calcd for $C_{23}H_{27}FN_4O_3S$ ([M]$^+$) 458; found 459 ([M + H]$^+$) | $^1$H NMR (DMSO-d$_6$) δ 9.32 (br, 1H), 9.12 (br, 1H), 7.55 (d, $J_{H,F}$=14.0 Hz, 1H), 7.20 (br, 1H), 3.81-3.64 (m, 3H), 3.64-3.38 (m, 3H), 3.52 (s, 3H, methoxy), 2.73 (m, 2H), 2.30-2.05 (m, 1H), 1.79 (m, 1H), 1.38 (d, J=6.7 Hz, 3H, methyl), 1.35 (d, J=6.7 Hz, 3H, methyl-epimer), 1.17-0.75 (m, 8H, c-Pr) | $^{19}$F NMR (DMSO-d$_6$) δ −125.4 (s, 1F) |
| 95 | 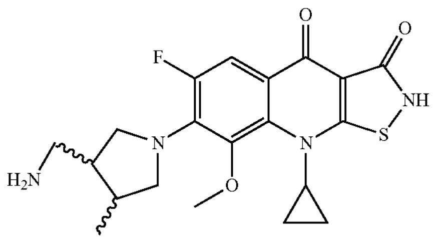 | 7-(3-(aminomethyl)-4-methyl-pyrrolidin-1-yl)-9-cyclopropyl-6-fluoro-8-methoxyisothiazolo[5,4-b]quinoline-3,4(2H,9H)-dione | HCl | 418.5 | LCMS (APCI): m/z calcd for $C_{20}H_{23}FN_4O_3S$ ([M]$^+$) 418; found 419 ([M + H]$^+$) | $^1$H NMR (DMSO-d$_6$): δ 1.04 (m, 7H), 2.09 (m, 2H), 2.85 (m, 1H), 3.01 (m, 1H), 3.30 (m, 1H), 3.52 (s, 3H), 3.73 (m, 4H), 7.55 (d, J=14.2 Hz, 1H), 8.05 (s (br), 1H) | $^{19}$F NMR (DMSO-d$_6$) δ −125.72 (s, 1F) |
| 96 | 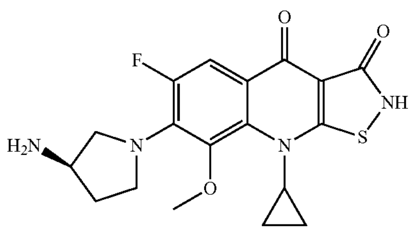 | (R)-7-(3-aminopyrrolidin-1-yl)-9-cyclopropyl-6-fluoro-8-methoxyisothiazolo[5,4-b]quinoline-3,4(2H,9H)-dione | HCl | 390.4 | LCMS m/z calcd for $C_{18}H_{19}FN_4O_3S$ 390 ([M$^+$]); found 391 ([M + H]$^+$, 100%). | (DMSO-D$_6$): δ 0.949-0.962 (2H, m), 1.117-1.148 (2H, m), 2.005-2.086 (1H, m), 2.259-2.320 (1H, m), 3.557 (3H, s), 3.601-3.899 (6H, m), 7.584 (1H, d, J=13.8 Hz), 8.249 (2H, brs) | |
| 97 | 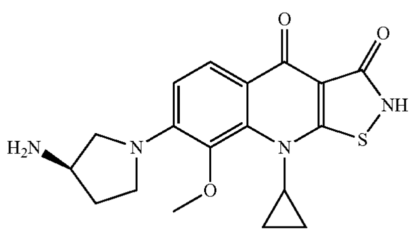 | (R)-7-(3-aminopyrrolidin-1-yl)-9-cyclopropyl-8-methoxyisothiazolo[5,4-b]quinoline-3,4(2H,9H)-dione | HCl | 372.4 | LCMS m/z calcd for $C_{18}H_{20}N_4O_3S$ 372 ([M$^+$]); found 373 ([M + H]$^+$, 100%). | (D$_2$O): δ 0.792-0.958 (2H, m), 1.083-1.222 (2H, m), 2.069-2.194 (1H, m), 2.306-2.444 (1H, m), 3.324 (3H, s), 3.442-3.804 (5H, m), 3.981-4.088 (1H, m), 6.517 (1H, d, J=7.8 Hz), 7.362 (1H, d, J=7.8 Hz). | (DMSO-d$_6$): −125.45 |

TABLE II-continued

| No. | Structure | Name | Salt | MW | MS | H-NMR | F-NMR |
|---|---|---|---|---|---|---|---|
| 98 | 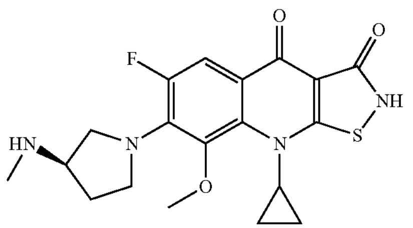 | (R)-9-cyclopropyl-6-fluoro-8-methoxy-7-(3-(methylamino)-pyrrolidin-1-yl)isothiazolo[5,4-b]quinoline-3,4(2H,9H)-dione | HCl | 404.5 | LCMS m/z calcd for $C_{19}H_{21}FN_4O_3S$ 404 ([M$^+$]); found 405 ([M + H]$^+$, 100%). | (DMSO-D$_6$): δ 0.933-0.983 (2H, m), 1.111-1.167 (2H, m), 2.056-2.175 (1H, m), 2.244-2.394 (1H, m), 2.645 (3H, brs), 3.669 (3H, s), 3.664-3.872 (6H, m) 7.589 (1H, d, J=13.5 Hz), 9.061 (1H, brs) | (DMSO-d$_6$): −125.30 |
| 99 | 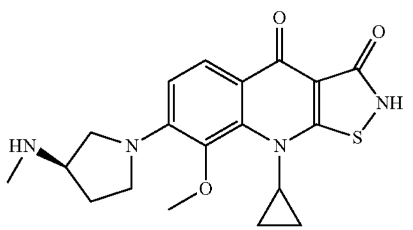 | (R)-9-cyclopropyl-8-methoxy-7-(3-(methylamino)-pyrrolidin-1-yl)isothiazolo[5,4-b]quinoline-3,4(2H,9H)-dione | HCl | 386.5 | LCMS m/z calcd for $C_{19}H_{22}N_4O_3S$ 386 ([M$^+$]); found 387 ([M + H]$^+$, 100%). | δ 0.972-1.068 (2H, m), 1.170-1.239 (2H, m), 2.121-2.222 (1H, m), 2.389-2.479 (1H, m), 2.768 (3H, s), 3.315-3.430 (1H, m), 3.407 (3H, s), 3.564-3.911 (5H, m), 6.693 (1H, d, J=8.7 Hz), 7.572 (1H, d, J=8.7 Hz). | |
| 100 | 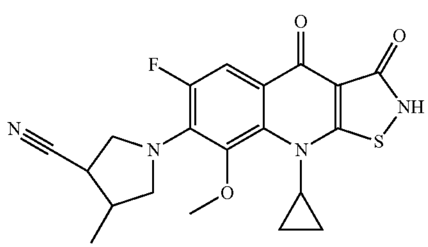 | 1-(9-cyclopropyl-6-fluoro-8-methoxy-3,4-dioxo-2,3,4,9-tetrahydroisothiazolo[5,4-b]quinolin-7-yl)-4-methylpyrrolidine-3-carbonitrile | HCl | 414.5 | LCMS m/z calcd for $C_{20}H_{19}FN_4O_3S$ 414 ([M$^+$]); found 415 ([M + H]$^+$, 100%). | $^1$H NMR (DMSO-d$_6$): δ 1.06 (m, 4H), 1.22 (d, J=6.6 Hz, 3H), 2.63 (m, 1H), 3.55 (s, 3H), 3.56 (m, 3H), 3.74 (s, 2H), 3.96 (m, 1H), 7.58 (d, J=13.8 Hz, 1H | $^{19}$F NMR (DMSO-d$_6$) δ −126.02 (s, 1F) |
| 101 | 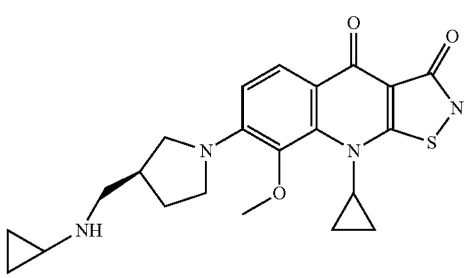 | (S)-9-cyclopropyl-7-(3-((cyclopropylamino)methyl)pyrrolidin-1-yl)-8-methoxyisothiazolo[5,4-b]quinoline-3,4(2H,9H)-dione | HCl | 426.5 | LCMS (APCI): m/z calcd for $C_{22}H_{26}FN_4O_3S$ ([M]$^+$) 426; found 427 ([M + H]$^+$) | $^1$H NMR (DMSO-d$_6$) δ 9.41 (br, 2H), 7.82 (d, J=9.1 Hz, 1H), 6.91 (br, 1H), 6.83 (d, J=9.1 Hz, 1H), 3.78 (m, 1H), 3.65 (m, 1H), 3.58-3.47 (m, 2H), 3.48 (s, 3H, methoxy), 3.33 (m, 1H), 3.14 (m, 2H), 2.72 (m, 2H), 2.19 (m, 1H), 1.83 (m, 1H), 1.14 (m, 2H, c-Pr), 0.96 (m, 4H, c-Pr), 0.74 (m, 2H, c-Pr), | |

TABLE II-continued

| No. | Structure | Name | Salt | MW | MS | H-NMR | F-NMR |
|---|---|---|---|---|---|---|---|
| 102 | 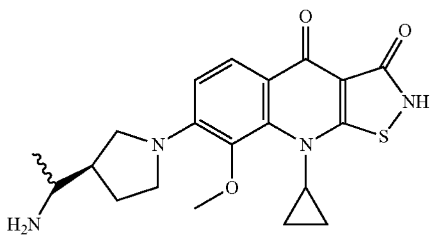 | (R)-7-(3-(1-aminoethyl)-pyrrolidin-1-yl)-9-cyclopropyl-8-methoxyisothiazolo[5,4-b]quinoline-3,4(2H,9H)-dione | HCl | 400.5 | LCMS (APCI): m/z calcd for $C_{20}H_{24}N_4O_3S$ ([M]$^+$) 400; found 401 ([M+H]$^+$) | $^1$H NMR (DMSO-$d_6$) δ 8.30 (br, 3H), 7.82 (d, J=9.0 Hz, 1H, ArH), 7.81 (d, J=9.0 Hz, 1H, ArH-epimer), 7.30 (br, 1H), 6.86 (d, J=9.0 Hz, 1H, ArH), 6.81 (d, J=9.0 Hz, 1H, ArH-epimer), 3.78 (m, 1H), 3.65-3.45 (m, 3H), 3.48 (s, 3H, methoxy), 3.47 (s, 3H, methoxy-epimer), 3.38-3.19 (m, 2H), 2.45 (m, 1H), 2.27-2.04 (m, 1H), 1.78 (m, 1H), 1.29 (d, J=6.5 Hz, 3H, methyl), 1.28 (d, J=6.5 Hz, 3H, methyl-epimer), 1.14 (m, 2H, c-Pr), 0.94 (m, 2H, c-Pr) | |
| 103 | 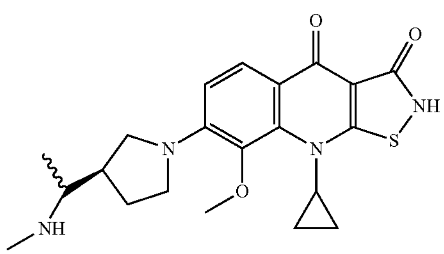 | (R)-9-cyclopropyl-8-methoxy-7-(3-(1-(methylamino)-ethyl)pyrrolidin-1-yl)isothiazolo[5,4-b]quinoline-3,4(2H,9H)-dione | HCl | 414.5 | LCMS (APCI): m/z calcd for $C_{21}H_{26}N_4O_3S$ ([M]$^+$) 414; found 415 ([M+H]$^+$) | $^1$H NMR (DMSO-$d_6$) δ 9.27 (br, 1H), 9.09 (br, 1H), 7.82 (d, J=9.0 Hz, 1H, ArH), 7.81 (d, J=9.0 Hz, 1H, ArH-epimer), 7.25 (br, 1H), 6.87 (d, J=9.0 Hz, 1H, ArH), 6.84 (d, J=9.0 Hz, 1H, ArH-epimer), 3.78 (m, 1H), 3.72-3.45 (m, 3H), 3.48 (s, 3H, methoxy), 3.39-3.22 (m, 2H), 2.67-2.50 (m, 1H), 2.55 (s, 3H, —NMe), 2.33-2.06 (m, 1H), 1.79 (m, 1H), 1.30 (d, J=6.6 Hz, 3H, methyl), 1.28 (d, J=6.6 Hz, 3H, methyl-epimer), 1.14 (m, 2H, c-Pr), 0.93 (m, 2H, c-Pr) | |

| No. | Structure | Name | Salt | MW | MS | H-NMR | F-NMR |
|---|---|---|---|---|---|---|---|
| 104 | 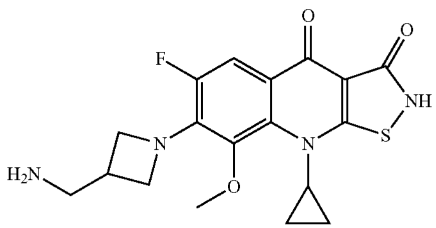 | 7-(3-(aminomethyl)azetidin-1-yl)-9-cyclopropyl-6-fluoro-8-methoxyisothiazolo[5,4-b]quinoline-3,4(2H,9H)-dione | Me-sulf-onate | 390.4 | LCMS m/z calcd for C₁₈H₁₉FN₄O₃S 390 ([M⁺]); found 391 ([M + H]⁺, 100%). | (DMSO-D₆): δ 0.947-1.012 (2H, m), 1.234-1.464 (2H, m), 2.856-2.942 (1H, m), 3.422-3.483 (2H, m), 3.566 (3H, s), 3.647-3.747 (1H, m), 4.034-4.137 (2H, m), 4.333-4.417 (2H, m), 7.554 (1H, d, J=13.8 Hz), 7.772 (2H, brs) | (DMSO-d₆): −133.75 |
| 105 | 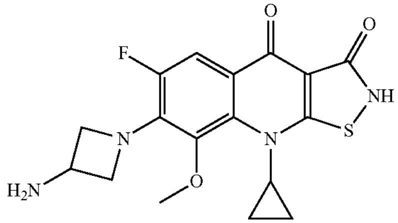 | 7-(3-aminoazetidin-1-yl)-9-cyclopropyl-6-fluoro-8-methoxyisothiazolo[5,4-b]quinoline-3,4(2H,9H)-dione | Me-sulf-onate | 376.4 | LCMS m/z calcd for C₁₇H₁₇FN₄O₃S 376 ([M⁺]); found 377 ([M + H]⁺, 100%). | (DMSO-D₆): δ 0.931-0.983 (2H, m), 1.123-1.192 (2H, m), 3.585 (3H, s), 3.739-3.824 (1H, m), 4.116-4.174 (1H, m), 4.224-4.279 (1H, m), 4.517-4.582 (2H, m), 7.587 (1H, d, J=13.2 Hz), 8.282 (2H, brd, J=3.3 Hz) | (DMSO-d₆): −134.02 |
| 106 | 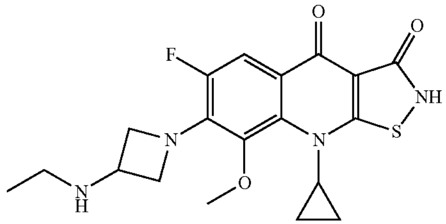 | 9-cyclopropyl-7-(3-(ethylamino)azetidin-1-yl)-6-fluoro-8-methoxyisothiazolo[5,4-b]quinoline-3,4(2H,9H)-dione | Me-sulf-onate | 404.5 | LCMS m/z calcd for C₁₉H₂₁FN₄O₃S 404 ([M⁺]); found 405 ([M + H]⁺, 100%). | (DMSO-D₆): δ 0.912-0.941 (2H, m), 0.963-0.972 (2H, m), 1.217 (3H, t, J=6.9 Hz), 3.006-3.025 (2H, m), 3.593 (3H, s), 3.742-3.818 (1H, m), 4.113-4.197 (1H, m), 4.333-4.394 (2H, m), 4.515-4.591 (2H, m), 7.591 (1H, d, J=13.2 Hz), 9.293 (1H, brs) | (DMSO-d₆): −133.88 |
| 107 | 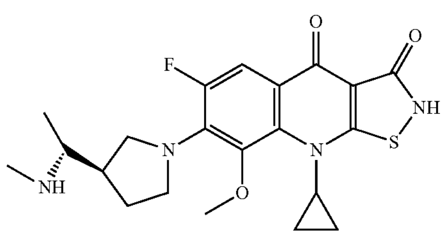 | 9-cyclopropyl-6-fluoro-8-methoxy-7-((R)-3-((R)-1-(methylamino)ethyl)pyrrolidin-1-yl)isothiazolo[5,4-b]quinoline-3,4(2H,9H)-dione | HCl | 432.5 | LCMS (APCI): m/z calcd for C₂₁H₂₅FN₄O₃S ([M⁺]) 432; found 433 ([M + H]⁺) | ¹H NMR (DMSO-d₆) δ 8.84 (br, 1H), 8.69 (br, 1H), 7.56 (d, J$_{H-F}$=14.0 Hz, 1H), 3.81-3.64 (m, 3H), 3.59-3.47 (m, 2H), 3.53 (s, 3H, methoxy), 3.29 (m, 1H), 2.58 (s, 3H, —NMe), 2.28-2.03 (m, 2H), 1.77 (m, 1H), 1.24 (d, J=6.6 Hz, 3H, methyl), 1.14 (m, 2H, c-Pr), 0.96 (m, 2H, c-Pr) | ¹⁹F NMR (DMSO-d₆) δ −125.4 (s, 1F) |

TABLE II-continued

| No. | Structure | Name | Salt | MW | MS | H-NMR | F-NMR |
|---|---|---|---|---|---|---|---|
| 108 | 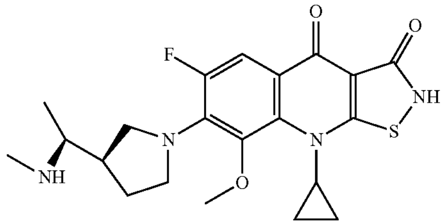 | 9-cyclopropyl-6-fluoro-8-methoxy-7-((R)-3-((S)-1-(methylamino)-ethyl)pyrrolidin-1-yl)isothiazolo[5,4-b]quinoline-3,4(2H,9H)-dione | HCl | 432.5 | LCMS (APCI): m/z calcd for $C_{21}H_{25}FN_4O_3S$ ([M]+) 432; found 433 ([M + H]+) | $^1$H NMR (DMSO-d$_6$) δ 9.07 (br, 1H), 8.86 (br, 1H), 7.55 (d, $J_{H,F}$ = 13.9 Hz, 1H), 3.82-3.64 (m, 3H), 3.61-3.45 (m, 2H), 3.55 (s, 3H, methoxy), 3.29 (m, 1H), 2.78-2.66 (m, 1H), 2.55 (s, 3H, —NMe), 2.07 (m, 1H), 1.75 (m, 1H), 1.29 (d, J=6.6 Hz, 3H, methyl), 1.14 (m, 2H, c-Pr), 0.95 (m, 2H, c-Pr) | $^{19}$F NMR (DMSO-d$_6$) δ −125.4 (s, 1F) |
| 109 | 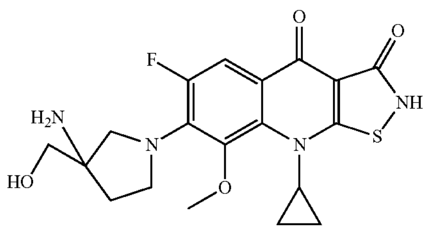 | 7-(3-amino-3-(hydroxymethyl)-pyrrolidin-1-yl)-9-cyclopropyl-6-fluoro-8-methoxyisothiazolo[5,4-b]quinoline-3,4(2H,9H)-dione | HCl | 420.5 | LCMS m/z calcd for $C_{19}H_{21}FN_4O_4S$ 420 ([M+]); found 421 ([M + H]+, 100%). | $^1$H—NMR (DMSO-D$_6$): δ 0.945-0.972 (2H, m), 1.125-1.148 (2H, m), 2.011-2.194 (2H, m), 3.575 (3H, s), 3.590-3.819 (7H, m), 7.598 (1H, d, J=13.8 Hz), 8.309 (2H, brs) | δ −125.28 |
| 110 | 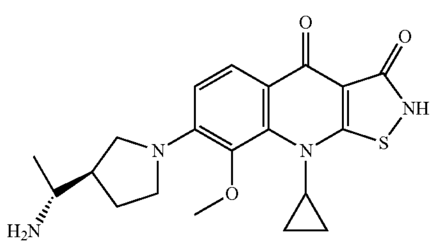 | 7-((R)-3-((R)-1-aminoethyl)pyrrolidin-1-yl)-9-cyclopropyl-8-methoxyisothiazolo[5,4-b]quinoline-3,4(2H,9H)-dione | HCl | 400.5 | LCMS (APCI): m/z calcd for $C_{20}H_{24}N_4O_3S$ ([M]+) 400; found 401 ([M + H]+) | $^1$H NMR (DMSO-d$_6$) δ 8.16 (br, 3H), 7.82 (d, J=9.0 Hz, 1H), 6.87 (d, J=9.0 Hz, 1H), 3.78 (m, 1H), 3.69-3.45 (m, 3H), 3.48 (s, 3H, methoxy), 3.35-3.18 (m, 2H), 2.45 (m, 1H), 2.28-2.00 (m, 1H), 1.78 (m, 1H), 1.27 (d, J=6.5 Hz, 3H, methyl), 1.18 (m, 2H, c-Pr), 0.93 (m, 2H, c-Pr) | |

TABLE II-continued

| No. | Structure | Name | Salt | MW | MS | H-NMR | F-NMR |
|---|---|---|---|---|---|---|---|
| 111 | 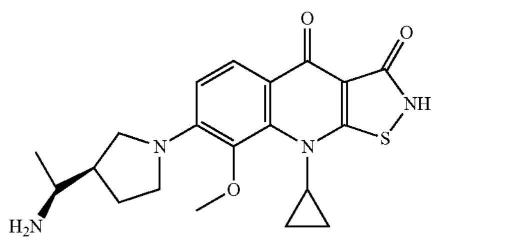 | 7-((R)-3-((S)-1-aminoethyl)-pyrrolidin-1-yl)-9-cyclopropyl-8-methoxyisothiazolo[5,4-b]quinoline-3,4(2H,9H)-dione | HCl | 400.5 | LCMS (APCI): m/z calcd for $C_{20}H_{24}N_4O_3S$ ([M]$^+$) 400; found 401 ([M + H]$^+$) | $^1$H NMR (DMSO-d$_6$) δ 8.20 (br, 3H), 7.84 (d, J=9.0 Hz, 1H), 6.82 (d, J=9.0 Hz, 1H), 3.78 (m, 1H), 3.65–3.45 (m, 3H), 3.48 (s, 3H, methoxy), 3.38–3.16 (m, 2H), 2.44 (m, 1H), 2.25–1.97 (m, 1H), 1.74 (m, 1H), 1.29 (d, J=6.5 Hz, 3H, methyl), 1.18 (m, 2H, c-Pr), 0.94 (m, 2H, c-Pr) | |
| 112 | 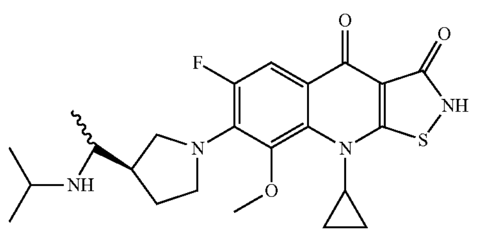 | (R)-9-cyclopropyl-6-fluoro-7-(3-(1-(isopropyl)amino)ethyl)pyrrolidin-1-yl)-8-methoxyisothiazolo[5,4-b]quinoline-3,4(2H,9H)-dione | HCl | 460.6 | LCMS (APCI): m/z calcd for $C_{23}H_{29}FN_4O_3S$ ([M]$^+$) 460; found 461 ([M + H]$^+$) | $^1$H NMR (DMSO-d$_6$) δ 9.01 (br, 1H), 8.44 (br, 1H), 7.55 (d, $J_{H-F}$=14.0 Hz, 1H), 3.82–3.62 (m, 3H), 3.60–3.32 (m, 3H), 3.53 (s, 3H methoxy), 2.52 (m, 1H), 2.36–2.04 (m, 2H), 1.79 (m, 1H), 1.37–1.19 (m, 9H), 1.13 (m, 2H, c-Pr), 0.94 (m, 2H, c-Pr) | $^{19}$F NMR (DMSO-d$_6$) δ -125.4 (s, 1F) |
| 113 | 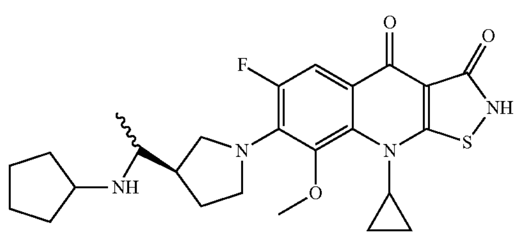 | (R)-7-(3-(1-(cyclopentyl)amino)ethyl)pyrrolidin-1-yl)-9-cyclopropyl-6-fluoro-8-methoxyisothiazolo[5,4-b]quinoline-3,4(2H,9H)-dione | HCl | 486.6 | LCMS (APCI): m/z calcd for $C_{25}H_{31}FN_4O_3S$ ([M]$^+$) 486; found 487 ([M + H]$^+$) | $^1$H NMR (DMSO-d$_6$) δ 9.27 (br, 1H), 8.78 (br, 1H), 7.55 (d, $J_{H-F}$=14.0 Hz, 1H), 6.53 (br, 1H), 3.92–3.46 (m, 5H), 3.52 (s, 3H, methoxy), 3.37 (m, 1H), 2.68 (m, 1H), 2.50–1.91 (m, 4H), 1.89–1.61 (m, 5H), 1.54 (m, 2H), 1.33 (d, J=6.6 Hz, 3H, methyl), 1.30 (d, J=6.6 Hz, 3H, methyl-epimer), 1.16 (m, 2H, c-Pr), 0.94 (m, 2H, c-Pr) | $^{19}$F NMR (DMSO-d$_6$) δ -125.3 (s, 1F), -125.4 (s, 1F, epimer) |

TABLE II-continued

| No. | Structure | Name | Salt | MW | MS | H-NMR | F-NMR |
|---|---|---|---|---|---|---|---|
| 114 | 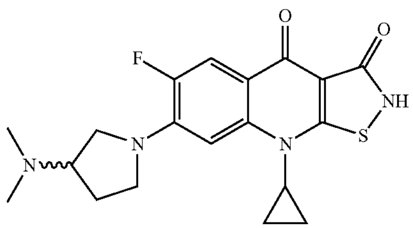 | 9-cyclopropyl-7-(3-(dimethyl-amino)pyrrolidin-1-yl)-6-fluoroisothiazolo[5,4-b]quinoline-3,4(2H,9H)-dione | | | | | |
| 115 | 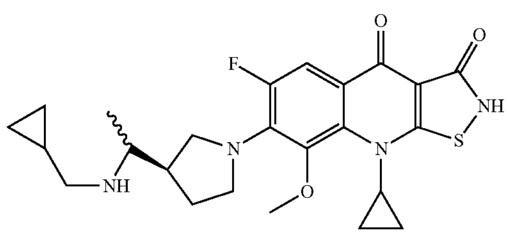 | (R)-9-cyclopropyl-7-(3-((cyclopropylmethyl amino)ethyl)-pyrrolidin-1-yl)-6-fluoro-8-methoxyisothiazolo[5,4-b]quinoline-3,4(2H,9H)-dione | HCl | 509.0 | LCMS (APCI): m/z calcd for C$_{24}$H$_{29}$FN$_{4}$O$_{3}$S ([M]$^{+}$) 472; found 473 ([M + H]$^{+}$) | $^{1}$H NMR (DMSO-d$_{6}$) δ 9.08 (br, 1H), 8.82 (br, 1H), 7.55 (d, $J_{H,F}$=14.0 Hz, 1H), 3.81-3.62 (m, 2H), 3.61-3.46 (m, 2H), 3.52 (s, 3H, methoxy), 3.38 (m, 1H), 2.99-2.51 (m, 3H), 2.49 (m, 2H), 2.30-2.03 (m, 1H), 1.79 (m, 1H), 1.31 (d, J=6.6 Hz, 3H, methyl), 1.27 (d, J=6.7 Hz, 3H, methyl-epimer), 1.13 (m, 2H, c-Pr), 0.94 (m, 2H, c-Pr), 0.58 (m, 2H, c-Pr), 0.39 (m, 2H, c-Pr) | $^{19}$F NMR (DMSO-d$_{6}$) δ −125.4 (s, 1F) |

Example 9

Antimicrobial Activity of Compounds

The antimicrobial activity of the compounds of the invention may be evaluated by a number of methods, including the following visual minimum inhibitory concentration (MIC) assay. This assay determines the minimum concentration of compound required to inhibit growth of a bacterial strain.

Minimum Inhibitory Concentration (MIC) Assay

Whole-cell antibacterial activity is determined by broth microdilution using conditions recommended by the NCCLS (see National Committee for Clinical Laboratory Standards. 2001. Performance standards for antimicrobial susceptibility testing: 11th informational supplement. Vol. 21, no. 1, M100-S11. National Committee for Clinical Laboratory Standards, Wayne, Pa.). Test compounds are dissolved in DMSO and diluted 1:50 in Mueller-Hinton II broth (Becton-Dickinson) to produce a 256 µg/ml stock solution. In a 96-well microtiter plate, the compound solution is serially two-fold diluted in Mueller-Hinton II broth. After the compounds are diluted, a 50 µl aliquot of the test organism (~$1\times10^6$ cfu/mL) is added to each well of the microtiter plate. The final test concentrations ranges from 0.125-128 µg/mL. Inoculated plates are incubated in ambient air at 37° C. for 18 to 24 hours. The organisms selected for testing included laboratory strains *S. aureus* ATCC 29213 and *E. coli* ATCC 25922 (strains purchased from American Type Culture Collection, Manassas, Va.), *S. aureus* FQR700699, and *P. aeruginosa* 27853. The minimum inhibitory concentration (MIC) is determined as the lowest concentration of compound that inhibited visible growth of the test organism.

Compounds 17-46, 49, and 52-113 were tested in this assay for anti-microbial activity against *S. Aureus*. Compounds 17-42, 44-46, 49, 52-83, 85-103, and 105-113 exhibited MIC values of 1 microgram/ml or less against *S. Aureus*. Certain of these compounds exhibited an MIC value of 0.1 microgram/ml or less against *S. Aureus*, and certain of these compounds also exhibited an MIC value of 0.01 microgram/ml against *S. Aureus* when tested in this assay. Compounds 17, 20, 22, 38-46, 49, and 52-113 were tested in this assay for anti-microbial activity against Methicillin Resistant *S. Aureus*. Compounds 42, 52-57, 59, 63, 66-67, 70-71, 73-77, 87-89, 92-95, 100, 102-103, 107-108, and 111-112 exhibited MIC values of 1 microgram/ml or less against Methicillin Resistant *S. Aureus*. Compounds 17-22, 26-46, 49, 52-58, 63, 67-68, 70-90, 93-95, and 100-106 were also tested in this assay for anti-microbial activity against *E. coli*. Compounds 17-22, 26-42, 44-46, 49, 52-58, 63, 67-68, 70-90, 93-95, 100-103, and 105-106 exhibited MIC values of 1 microgram/ml or less against *E. coli*.

Example 10

Cell Viability Staining with Alamar Blue

To determine whether the microcidal effect observed against *S. aureus* and *E. coli* is specific to bacterial cells, compounds are screened for cell viability effects on several human cell types.

Optimal cell density is first determined by plating cells in a 96-well plate standard sterile tissue culture plates in 100 µl media, 10% FBS at six cell densities from 500 cells/well to 15,000 cells/well. A cell free well containing only media is used as a control. Cells are incubated at 37° C. in a 5% $CO_2$ incubator for 24 hours. 10% culture volume (10 ul) of Alamar Blue (Biosource, DAL1100, 100 mL) is then added. Cells are incubated at 37° C. in a 5% CO2 incubator and read in a Victor V plate reader, 544 nm excitation, 590 nm emission, at 3, 4, and 24 hours after the addition of Alamar Blue. The cell number vs. change in fluorescence is plotted to determine linearity of signal vs. cell number. The optimal density varies between 500-15,000 cells/well depending on the specific cell type. The optimal density is selected based on the highest number of cells that is still in the linear response range.

Determination of Compound Cytotoxicity

Cells are plated at optimal cell density in a standard sterile tissue culture 96 well plate, and incubated at 37° C. O/N in a 5% $CO_2$ incubator. 12 to 48 hours post-plating media is removed. The cells are washed 1 or 2 times with 1×PBS and replaced with fresh media containing the test compound in 1% DMSO. 24 to 72 hours after addition of compound, the media is removed, and the cells washed 1 to 2 times with 1×PBS. Fresh media containing ¹⁄₁₀ volume of Alamar Blue is then added. Plates are incubated 4 hours at 37° C. in a 5% CO2 incubator and read in a Victor V plate reader, 544 nm excitation, 590 nm emission.

Compounds are diluted to 20 micromolar in 1% DMSO and media and screened in duplicate to obtain single concentration cytotoxicity data. Eight concentration points from 0.78 micromolar to 100 micromolar, run in duplicate, are used to determine cyclotoxicity CC50 values. Cells with 1% DMSO and media are used as a negative control, compounds having a known CC50 against a particular cell type are used as positive controls.

The change in fluorescence vs. concentration of test compound is plotted to determine the cytotoxicity of the compound.

Sample media conditions, optimal plating densities, and positive control compounds for two cell types screened are presented in Table III.

Certain compounds disclosed in Examples 1 to 8 exhibit CC50 values greater than 10 uM against each of the cell lines listed below. Other cell types that may be used include but are not limited to Balb/3TC, CEM-SS, HeLa, Hep2, HepG2, HT-29, MRC-5, SK-N-SH, U-87 MG, 293T, and Huh-7. More preferred are compounds with a CC50 value greater than 50 uM. Most preferred are compounds with a CC50 value greater than 100 uM.

TABLE III

| Cell Line | Media | Plating Density | Positive Control |
|---|---|---|---|
| CHO (Chinese hamster ovary) | 1. F-12 Nutrient Mixture (Gibco #11765-054) containing 10% FBS, 1% Pen Strep, 1.5 g/L Sodium Bicarbonate 2. McCoy's 5a | 7,000 cells/well | Terfenadine $CC_{50}$ = 4.3-6.5 µM |

TABLE III-continued

| Cell Line | Media | Plating Density | Positive Control |
|---|---|---|---|
| Hep 2 (laryngeal carcinoma) | medium, 10% FBS and PS/Gln Minimum Essential Medium - Alpha Medium (Gibco # 12571-063) containing 10% FBS, 1% Pen Strep, 1.5 g/L Sodium Bicarbonate | 7,000 cells/well | Terfenadine $CC_{50}$ = 3-5 µM |

What is claimed is:

1. A compound of Formula A

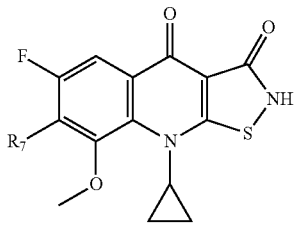

Formula A or a tautomer thereof of Formula B

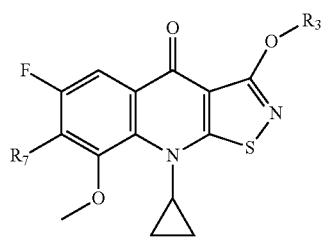

Formula B or a pharmaceutically acceptable salt of Formula A or Formula B, wherein $R_3$ is hydrogen, $C_1$-$C_6$alkyl, or $C_2$-$C_6$alkanoyl; and $R_7$ is a pyrrolidinyl, piperazinyl, morpholinyl, thiomorpholinyl, or azepanyl group substituted with substituted with 0 to 2 substituents independently chosen from or more of (a) and 0 or 1 substituents (b); or $R_7$ is a group of formula

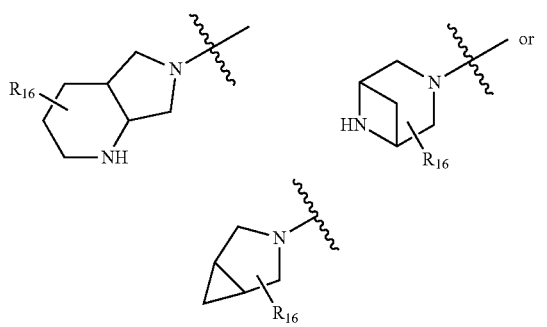

in which $R_{16}$ is 0 or 1 or more substituents chosen from amino, hydroxy, chloro, fluoro, methyl, methoxy, trifluoromethyl, and trifluoromethoxy;

each of which $R_7$ is substituted with 0 or 1 or more substituents independently chosen from (a) and 0 or 1 substituents chosen from (b); wherein (a) is chosen from halogen, hydroxy, amino, nitro, $C_1$-$C_4$alkyl, $C_1$-$C_4$alkoxy, $C_1$-$C_2$haloalkyl, and $C_1$-$C_2$haloalkoxy, and (b) is oxo, amino, cyano, hydroxy$C_1$-$C_4$alkyl, amino$C_1$-$C_4$alkyl, $C_1$-$C_6$alkylthio, $C_2$-$C_6$alkanoyl, (mono- or di-$C_1$-$C_4$alkyl)amino$C_0$-$C_4$alkyl, ($C_3$-$C_7$cycloalkyl)$C_0$-$C_4$alkyl, ($C_3$-$C_7$cycloalkyl)amino$C_0$-$C_4$alkyl, ($C_3$-$C_7$cycloalkyl)($C_1$-$C_4$alkyl)amino$C_0$-$C_4$alkyl, (heterocycloalkyl)$C_0$-$C_4$alkyl, or (aryl)$C_0$-$C_4$alkyl, where each of (b) other than oxo and cyano is substituted with 0 to 2 substituents independently chosen from halogen, hydroxy, amino, cyano, nitro, oxo, —COOH, —CONH$_2$, $C_1$-$C_4$alkyl, $C_2$-$C_4$alkenyl, $C_2$-$C_4$alkynyl, $C_1$-$C_4$alkoxy, mono- and di-($C_1$-$C_4$alkyl)amino, $C_1$-$C_2$haloalkyl, and $C_1$-$C_2$haloalkoxy.

2. A compound or salt of claim 1 of Formula A.

3. A compound or salt of claim 2, wherein $R_7$ is a pyrrolidinyl, piperazinyl, morpholinyl, thiomorpholinyl, or azepanyl group substituted with substituted with 0 to 2 substituents independently chosen from 0 or 1 or more substituents (a) and 0 or 1 substituents (b); wherein (a) is chosen from halogen, hydroxy, amino, nitro, $C_1$-$C_4$alkyl, $C_1$-$C_4$alkoxy, $C_1$-$C_2$haloalkyl, and $C_1$-$C_2$haloalkoxy, (b) is oxo, amino, cyano, hydroxy$C_1$-$C_4$alkyl, amino$C_1$-$C_4$alkyl, $C_1$-$C_6$alkylthio, $C_2$-$C_6$alkanoyl, (mono- or di-$C_1$-$C_4$alkyl)amino$C_0$-$C_4$alkyl, ($C_3$-$C_7$cycloalkyl)$C_0$-$C_4$alkyl, ($C_3$-$C_7$cycloalkylamino)$C_0$-$C_4$alkyl, ($C_3$-$C_7$cycloalkyl)($C_1$-$C_4$alkyl)amino$C_0$-$C_4$alkyl, (heterocycloalkyl)$C_0$-$C_4$alkyl, or (aryl)$C_0$-$C_4$alkyl, where each of (b) other than oxo and cyano is substituted with 0 to 2 substituents independently chosen from halogen, hydroxy, amino, cyano, nitro, oxo, —COOH, —CONH$_2$, $C_1$-$C_4$alkyl, $C_2$-$C_4$alkenyl, $C_2$-$C_4$alkynyl, $C_1$-$C_4$alkoxy, mono- and di-($C_1$-$C_4$alkyl)amino, $C_1$-$C_2$haloalkyl, and $C_1$-$C_2$haloalkoxy.

4. A compound or salt of claim 3, wherein $R_7$ is a pyrrolidinyl or piperazinyl group substituted with substituted with 0 to 2 substituents independently chosen from 0 or 1 or more substituents (a) and 0 or 1 substituents (b).

5. A compound or salt of claim 4, wherein $R_7$ is a pyrrolidinyl group, which is substituted with 0 to 2 substituents independently chosen from one or more of (a) and 0 or 1 substituents (b).

6. A compound or salt of claim 5, wherein $R_7$ is pyrrolidinyl group substituted with one group (b) and optionally substituted with 1 methyl or halogen substituent wherein (b) is oxo, amino, cyano, hydroxy$C_1$-$C_4$alkyl, amino$C_1$-$C_4$alkyl, $C_2$-$C_4$alkanoyl, (mono- or di-$C_1$-$C_4$alkyl)amino$C_0$-$C_4$alkyl, ($C_3$-$C_7$cycloalkyl)$C_0$-$C_2$alkyl substituted with amino, ($C_3$-

C₇cycloalkylamino)C₀-C₄alkyl, or (C₃-C₇cycloalkyl)(C₁-C₄alkyl)aminoC₀-C₄alkyl.

7. A compound or salt of claim 1, where R₇ is a group of formula

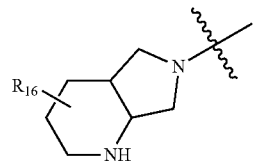 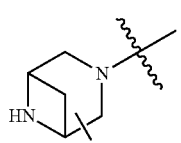

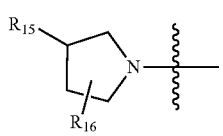 or 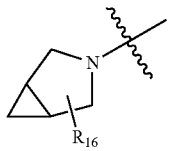

in which

R₁₅ is (b); and

R₁₆ is 0 or 1 or more substituents chosen from amino, hydroxy, chloro, fluoro, methyl, methoxy, trifluoromethyl, and trifluoromethoxy.

8. A compound or salt of claim 7, wherein

R₁₅ is oxo, amino, cyano, hydroxyC₁-C₄alkyl, aminoC₁-C₄alkyl, C₂-C₄alkanoyl, (mono- or di-C₁-C₄alkylamino)C₀-C₄alkyl, (C₃-C₇cycloalkyl)C₀-C₂alkyl substituted with amino, (C₃-C₇cycloalkylamino)C₀-C₄alkyl, or (C₃-C₇cycloalkyl)(C₁-C₄alkyl)aminoC₀-C₄alkyl.

9. A compound or salt of claim 7, wherein

R₁₅ is oxo, cyano, hydroxyC₁-C₄alkyl, aminoC₁-C₄alkyl, acetyl, (mono- or di-C₁-C₂alkylamino)C₁-C₄alkyl, cyclopropyl substituted with amino, or (C₃-C₇cycloalkylamino)C₀-C₄alkyl; and R₁₆ is 0 or 1 substituent chosen from hydroxy, amino, chloro, and methyl.

10. A compound or salt of claim 1, wherein R₇ is

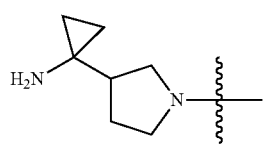 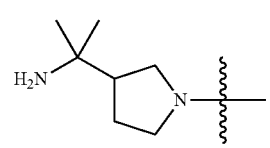

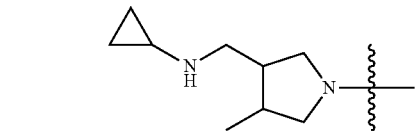

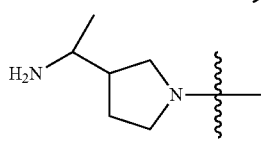 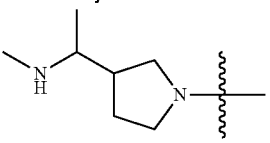

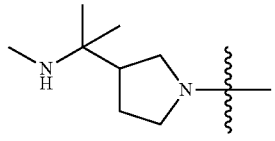 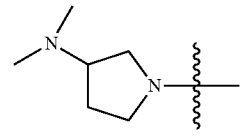

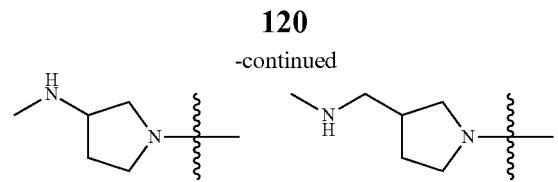

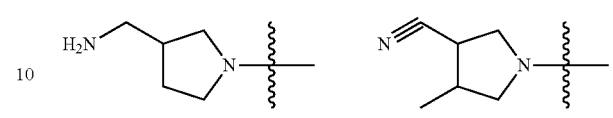

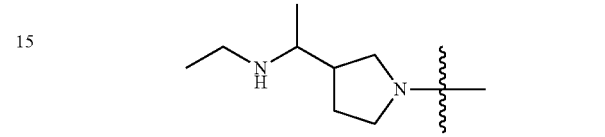

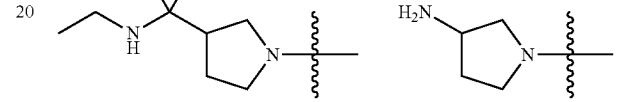

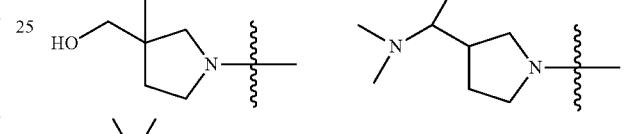

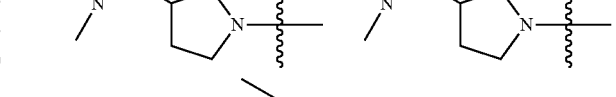

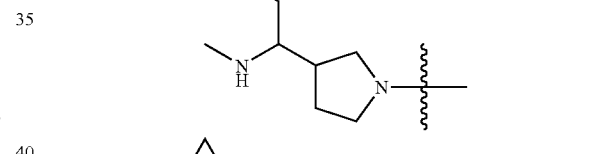

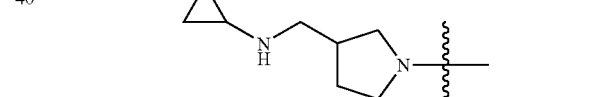

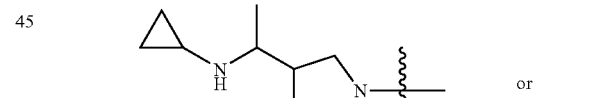

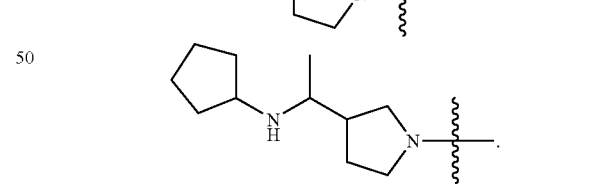

11. A compound or salt of claim 1, wherein R₇ is

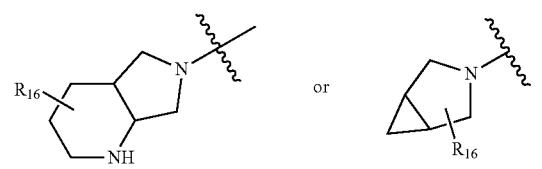 or 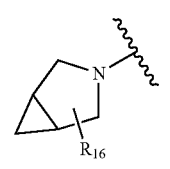

wherein

R$_{16}$ is 0 or 1 or more substituents chosen from amino, hydroxy, chloro, fluoro, methyl, methoxy, trifluoromethyl, and trifluoromethoxy.

12. A compound or salt of claim 1, wherein the compound is 9-cyclopropyl-6-fluoro-8-methoxy-7-(piperazin-1-yl)isothiazolo[5,4-b]quinoline-3,4(2H,9H)-dione;

9-cyclopropyl-7-(3-(dimethylamino)pyrrolidin-1-yl)-6-fluoro-8-methoxyisothiazolo[5,4-b]quinoline-3,4(2H,9H)-dione;

(R)-7-(3-(2-aminopropan-2-yl)pyrrolidin-1-yl)-9-cyclopropyl-6-fluoro-8-methoxyisothiazolo[5,4-b]quinoline-3,4(2H,9H)-dione;

(R)-7-(3-(1-aminocyclopropyl)pyrrolidin-1-yl)-9-cyclopropyl-6-fluoro-8-methoxyisothiazolo[5,4-b]quinoline-3,4(2H,9H)-dione;

7-(3-(2-aminopropan-2-yl)pyrrolidin-1-yl)-9-cyclopropyl-6-fluoro-8-methoxyisothiazolo[5,4-b]quinoline-3,4(2H,9H)-dione;

(S)-7-(3-(2-aminopropan-2-yl)pyrrolidin-1-yl)-9-cyclopropyl-6-fluoro-8-methoxyisothiazolo[5,4-b]quinoline-3,4(2H,9H)-dione;

(S)-7-(3-(aminomethyl)pyrrolidin-1-yl)-9-cyclopropyl-6-fluoro-8-methoxyisothiazolo[5,4-b]quinoline-3,4(2H,9H)-dione;

7-(3-(aminomethyl)pyrrolidin-1-yl)-9-cyclopropyl-6-fluoro-8-methoxyisothiazolo[5,4-b]quinoline-3,4(2H,9H)-dione;

(R)-7-(3-(aminomethyl)pyrrolidin-1-yl)-9-cyclopropyl-6-fluoro-8-methoxyisothiazolo[5,4-b]quinoline-3,4(2H,9H)-dione;

(R)-7-(3-(1-aminoethyl)pyrrolidin-1-yl)-9-cyclopropyl-6-fluoro-8-methoxyisothiazolo[5,4-b]quinoline-3,4(2H,9H)-dione;

(R)-9-cyclopropyl-6-fluoro-8-methoxy-7-(3-(1-(methylamino)ethyl)pyrrolidin-1-yl)isothiazolo[5,4-b]quinoline-3,4(2H,9H)-dione;

(R)-9-cyclopropyl-6-fluoro-8-methoxy-7-(3-(2-(methylamino)propan-2-yl)pyrrolidin-1-yl)isothiazolo[5,4-b]quinoline-3,4(2H,9H)-dione;

(R)-9-cyclopropyl-7-(3-(1-(ethylamino)ethyl)pyrrolidin-1-yl)-6-fluoro-8-methoxyisothiazolo[5,4-b]quinoline-3,4(2H,9H)-dione;

(R)-9-cyclopropyl-7-(3-(1-(dimethylamino)ethyl)pyrrolidin-1-yl)-6-fluoro-8-methoxyisothiazolo[5,4-b]quinoline-3,4(2H,9H)-dione;

(R)-9-cyclopropyl-7-(3-(2-(dimethylamino)propan-2-yl)pyrrolidin-1-yl)-6-fluoro-8-methoxyisothiazolo[5,4-b]quinoline-3,4(2H,9H)-dione;

(S)-9-cyclopropyl-7-(3-((dimethylamino)methyl)pyrrolidin-1-yl)-6-fluoro-8-methoxyisothiazolo[5,4-b]quinoline-3,4(2H,9H)-dione;

(S)-9-cyclopropyl-6-fluoro-8-methoxy-7-(3-((methylamino)methyl)pyrrolidin-1-yl)isothiazolo[5,4-b]quinoline-3,4(2H,9H)-dione;

(S)-9-cyclopropyl-7-(3-((cyclopropylamino)methyl)pyrrolidin-1-yl)-6-fluoro-8-methoxyisothiazolo[5,4-b]quinoline-3,4(2H,9H)-dione;

(R)-9-cyclopropyl-7-(3-(2-(ethylamino)propan-2-yl)pyrrolidin-1-yl)-6-fluoro-8-methoxyisothiazolo[5,4-b]quinoline-3,4(2H,9H)-dione;

(R)-7-(3-(aminomethyl)pyrrolidin-1-yl)-9-cyclopropyl-8-methoxyisothiazolo[5,4-b]quinoline-3,4(2H,9H)-dione;

9-cyclopropyl-6-fluoro-8-methoxy-7-((R)-3-((S)-1-(methylamino)propyl)pyrrolidin-1-yl)isothiazolo[5,4-b]quinoline-3,4(2H,9H)-dione;

9-cyclopropyl-6-fluoro-8-methoxy-7-((R)-3-((R)-1-(methylamino)propyl)pyrrolidin-1-yl)isothiazolo[5,4-b]quinoline-3,4(2H,9H)-dione;

(R)-9-cyclopropyl-7-(3-(1-(cyclopropylamino)ethyl)pyrrolidin-1-yl)-6-fluoro-8-methoxyisothiazolo[5,4-b]quinoline-3,4(2H,9H)-dione;

(S)-9-cyclopropyl-7-(3-(1-(cyclopropylamino)ethyl)pyrrolidin-1-yl)-6-fluoro-8-methoxyisothiazolo[5,4-b]quinoline-3,4(2H,9H)-dione;

7-(3-(aminomethyl)-4-methylpyrrolidin-1-yl)-9-cyclopropyl-6-fluoro-8-methoxyisothiazolo[5,4-b]quinoline-3,4(2H,9H)-dione;

(R)-7-(3-aminopyrrolidin-1-yl)-9-cyclopropyl-6-fluoro-8-methoxyisothiazolo[5,4-b]quinoline-3,4(2H,9H)-dione;

(R)-9-cyclopropyl-6-fluoro-8-methoxy-7-(3-(methylamino)pyrrolidin-1-yl)isothiazolo[5,4-b]quinoline-3,4(2H,9H)-dione;

1-(9-cyclopropyl-6-fluoro-8-methoxy-3,4-dioxo-2,3,4,9-tetrahydroisothiazolo[5,4-b]quinolin-7-yl)-4-methylpyrrolidine-3-carbonitrile;

(R)-9-cyclopropyl-8-methoxy-7-(3-(1-(methylamino)ethyl)pyrrolidin-1-yl)isothiazolo[5,4-b]quinoline-3,4(2H,9H)-dione;

7-(3-(aminomethyl)azetidin-1-yl)-9-cyclopropyl-6-fluoro-8-methoxyisothiazolo[5,4-b]quinoline-3,4(2H,9H)-dione;

7-(3-aminoazetidin-1-yl)-9-cyclopropyl-6-fluoro-8-methoxyisothiazolo[5,4-b]quinoline-3,4(2H,9H)-dione;

9-cyclopropyl-7-(3-(ethylamino)azetidin-1-yl)-6-fluoro-8-methoxyisothiazolo[5,4-b]quinoline-3,4(2H,9H)-dione;

9-cyclopropyl-6-fluoro-8-methoxy-7-((R)-3-((R)-1-(methylamino)ethyl)pyrrolidin-1-yl)isothiazolo[5,4-b]quinoline-3,4(2H,9H)-dione;

9-cyclopropyl-6-fluoro-8-methoxy-7-((R)-3-((S)-1-(methylamino)ethyl)pyrrolidin-1-yl)isothiazolo[5,4-b]quinoline-3,4(2H,9H)-dione;

7-(3-amino-3-(hydroxymethyl)pyrrolidin-1-yl)-9-cyclopropyl-6-fluoro-8-methoxyisothiazolo[5,4-b]quinoline-3,4(2H,9H)-dione;

(R)-9-cyclopropyl-6-fluoro-7-(3-(1-(isopropylamino)ethyl)pyrrolidin-1-yl)-8-methoxyisothiazolo[5,4-b]quinoline-3,4(2H,9H)-dione; or (R)-7-(3-(1-(cyclopentylamino)ethyl)pyrrolidin-1-yl)-9-cyclopropyl-6-fluoro-8-methoxyisothiazolo[5,4-b]quinoline-3,4(2H,9H)-dione.

13. A pharmaceutical composition comprising a compound or salt of claim 1, together with a pharmaceutically acceptable carrier, diluent, or excipient.

14. A pharmaceutical composition of claim 13, wherein the composition is formulated as an injectable fluid, an aerosol, a cream, a gel, a pill, a capsule, a tablet, a syrup, a transdermal patch, or an ophthalmic solution.

15. A compound or salt of claim 12, wherein the compound is (R)-7-(3-(2-aminopropan-2-yl)pyrrolidin-1-yl)-9-cyclopropyl-6-fluoro-8-methoxyisothiazolo[5,4-b]quinoline-3,4 (2H,9H)-dione.

16. A compound or salt of claim 12, wherein the compound is (R)-7-(3-(1-aminocyclopropyl)pyrrolidin-1-yl)-9-cyclopropyl-6-fluoro-8-methoxyisothiazolo[5,4-b]quinoline-3,4 (2H,9H)-dione.

17. A compound or salt of claim 12, wherein the compound is 7-(3-(2-aminopropan-2-yl)pyrrolidin-1-yl)-9-cyclopropyl-6-fluoro-8-methoxyisothiazolo[5,4-b]quinoline-3,4(2H, 9H)-dione.

18. A compound or salt of claim 12, wherein the compound is (R)-9-cyclopropyl-7-(3-(2-(ethylamino)propan-2-yl)pyrrolidin-1-yl)-6-fluoro-8-methoxyisothiazolo[5,4-b]quinoline-3,4(2H,9H)-dione.

19. A package comprising the pharmaceutical composition of claim 13 in a container and further comprising instructions for using the composition to treat a patient suffering from a microorganism infection.

20. A package of claim 19 wherein the instructions are instructions for using the composition to treat a patient suffering from a bacterial infection.

21. A method for treating or preventing a bacterial or protozoal infection comprising administering to a patient in need thereof a therapeutically effective amount of a compound or salt of claim 1.

22. The method of claim 21, wherein the infection is an *S. Aureus* infection and the patient is a human patient.

\* \* \* \* \*